(12) United States Patent
Mach et al.

(10) Patent No.: US 7,227,057 B2
(45) Date of Patent: Jun. 5, 2007

(54) PLANT CENTROMERE COMPOSITIONS

(75) Inventors: Jennifer Mach, Chicago, IL (US); Helge Zieler, Chicago, IL (US); James Jin, Chicago, IL (US); Kevin Keith, Chicago, IL (US); Gregory Copenhaver, Chapel Hill, NC (US); Daphne Preuss, Chicago, IL (US)

(73) Assignees: Chromatin, Inc., Chicago, IL (US); The University of Chicago, Chicago, IL (US)

( * ) Notice: Subject to any disclaimer, the term of this patent is extended or adjusted under 35 U.S.C. 154(b) by 44 days.

(21) Appl. No.: 11/049,537

(22) Filed: Feb. 2, 2005

(65) Prior Publication Data

US 2005/0241015 A1    Oct. 27, 2005

Related U.S. Application Data

(63) Continuation of application No. 10/170,912, filed on Jun. 12, 2002, now Pat. No. 7,119,250, which is a continuation-in-part of application No. 09/553,231, filed on Apr. 19, 2000, now Pat. No. 6,900,012, which is a continuation of application No. 09/090,051, filed on Jun. 3, 1998, now Pat. No. 6,156,953, said application No. 10/170,912 is a continuation-in-part of application No. 09/531,120, filed on Mar. 17, 2000, now Pat. No. 6,972,197.

(60) Provisional application No. 60/172,493, filed on Dec. 16, 1999, provisional application No. 60/154,603, filed on Sep. 17, 1999, provisional application No. 60/153,584, filed on Sep. 13, 1999, provisional application No. 60/134,770, filed on May 18, 1999, provisional application No. 60/127,409, filed on Apr. 1, 1999, provisional application No. 60/125,219, filed on Mar. 18, 1999, provisional application No. 60/073,741, filed on Feb. 5, 1998, provisional application No. 60/048,451, filed on Jun. 3, 1997.

(51) Int. Cl.
*C12N 15/82* (2006.01)
*C12N 15/87* (2006.01)
*C12N 5/10* (2006.01)
*C12N 5/04* (2006.01)
*A01H 5/10* (2006.01)
*A01H 5/00* (2006.01)

(52) U.S. Cl. .................... 800/312; 435/468; 435/419; 435/490; 435/320.1; 435/415; 800/278; 536/23.1; 536/24.2

(58) Field of Classification Search ..................... None
See application file for complete search history.

(56) References Cited

U.S. PATENT DOCUMENTS

| | | |
|---|---|---|
| 4,889,806 A | 12/1989 | Olson et al. |
| 5,015,580 A * | 5/1991 | Christou et al. ............ 800/267 |
| 5,270,201 A | 12/1993 | Richards et al. |
| 5,288,625 A | 2/1994 | Hadlaczky |
| 5,316,931 A | 5/1994 | Donson et al. |
| 5,491,076 A | 2/1996 | Carrington et al. |
| 5,530,187 A | 6/1996 | Lamb et al. |
| 5,589,379 A | 12/1996 | Kridl et al. |
| 5,650,303 A | 7/1997 | Kridl et al. |
| 5,695,967 A | 12/1997 | Van Bokkelen et al. |
| 5,712,134 A | 1/1998 | Hadlaczky |
| 5,721,118 A | 2/1998 | Scheffler |
| 5,733,744 A | 3/1998 | Hamilton |
| 5,766,885 A | 6/1998 | Carrington et al. |
| 5,866,793 A | 2/1999 | Baga et al. |
| 5,869,294 A | 2/1999 | Harrington et al. |
| 5,877,402 A | 3/1999 | Maliga et al. |
| 5,891,625 A | 4/1999 | Buchardt et al. |
| 5,891,691 A | 4/1999 | Hadlaczky |
| 5,925,808 A | 7/1999 | Oliver et al. |
| 5,977,439 A | 11/1999 | Hamilton |
| 5,977,441 A | 11/1999 | Oliver et al. |
| 6,025,155 A * | 2/2000 | Hadlaczky et al. ........ 435/69.1 |
| 6,077,697 A | 6/2000 | Hadlaczky et al. |
| 6,127,171 A | 10/2000 | Slilaty et al. |
| 6,156,953 A | 12/2000 | Preuss et al. |
| 6,162,963 A | 12/2000 | Kucherlapati et al. |
| 6,265,211 B1 | 7/2001 | Choo et al. |
| 6,277,608 B1 | 8/2001 | Hartley et al. |
| 6,277,632 B1 | 8/2001 | Harney |
| 6,291,243 B1 | 9/2001 | Fogarty et al. |
| 6,337,431 B1 | 1/2002 | Tricoli et al. |
| 6,348,353 B1 | 2/2002 | Harrington et al. |
| 6,365,377 B1 | 4/2002 | Patten et al. |
| 6,369,296 B1 | 4/2002 | Ratcliff et al. |
| 6,376,234 B1 | 4/2002 | Grimsley et al. |
| 6,376,745 B1 | 4/2002 | Atabekov et al. |
| 6,388,168 B1 | 5/2002 | Maliga et al. |
| 6,391,639 B1 | 5/2002 | Schenk et al. |

(Continued)

FOREIGN PATENT DOCUMENTS

EP        0320500        6/1989

(Continued)

OTHER PUBLICATIONS

Avramova 2002 Plant Physiology 129:40-49.*

(Continued)

*Primary Examiner*—David T. Fox
*Assistant Examiner*—Brent T Page
(74) *Attorney, Agent, or Firm*—Marshall, Gerstein & Borun LLP

(57) ABSTRACT

The present invention provides for the nucleic acid sequences of plant centromeres. This will permit construction of stably inherited recombinant DNA constructs and minichromosomes which can serve as vectors for the construction of transgenic plant and animal cells.

7 Claims, 55 Drawing Sheets

U.S. PATENT DOCUMENTS

| | | |
|---|---|---|
| 6,455,315 B1 | 9/2002 | Baszczynski et al. |
| 6,472,586 B1 | 10/2002 | Maliga et al. |
| 6,475,798 B2 | 11/2002 | Fogarty et al. |
| 6,495,318 B2 | 12/2002 | Harney |
| 6,514,693 B1 | 2/2003 | Lansdorp |
| 6,573,427 B1 | 6/2003 | Atabekov et al. |
| 2001/0008025 A1 | 7/2001 | Hadlaczky et al. |
| 2002/0028513 A1 | 3/2002 | Fogarty et al. |
| 2002/0034814 A1 | 3/2002 | Atabekov et al. |
| 2002/0059660 A1 | 5/2002 | Tricoli et al. |
| 2002/0072097 A1 | 6/2002 | Delcardayre et al. |
| 2002/0076811 A1 | 6/2002 | Okazaki et al. |
| 2002/0094574 A1 | 7/2002 | Hartley et al. |
| 2002/0108146 A1 | 8/2002 | Pang et al. |
| 2002/0111930 A1 | 8/2002 | Battles |
| 2002/0123053 A1 | 9/2002 | Luo et al. |
| 2002/0123145 A1 | 9/2002 | Ow |
| 2002/0128457 A1 | 9/2002 | Anderson et al. |
| 2002/0132348 A1 | 9/2002 | Bradshaw et al. |
| 2002/0151058 A1 | 10/2002 | Perkins et al. |
| 2002/0155530 A1 | 10/2002 | Szybalski et al. |
| 2002/0160410 A1 | 10/2002 | Hadlaczky et al. |
| 2002/0160970 A1 | 10/2002 | Hadlaczky et al. |
| 2002/0172997 A1 | 11/2002 | Hartley et al. |
| 2002/0174453 A1 | 11/2002 | Daniell et al. |
| 2002/0192819 A1 | 12/2002 | Hartley et al. |
| 2003/0003435 A1 | 1/2003 | DeJong et al. |
| 2003/0003466 A1 | 1/2003 | Harrington et al. |
| 2003/0022204 A1 | 1/2003 | Landsorp |
| 2003/0032186 A1 | 2/2003 | Jorgensen et al. |
| 2003/0033617 A1 | 2/2003 | Hadlaczky et al. |
| 2003/0041353 A1 | 2/2003 | Daniell et al. |
| 2003/0049665 A1 | 3/2003 | Szybalski et al. |
| 2003/0064509 A1 | 4/2003 | Marynen et al. |
| 2003/0077804 A1 | 4/2003 | Byrd et al. |
| 2003/0083293 A1 | 5/2003 | Hadlaczky et al. |
| 2003/0084482 A1 | 5/2003 | Hall et al. |
| 2003/0088081 A1 | 5/2003 | Maliga et al. |
| 2003/0097678 A1 | 5/2003 | Kushinov et al. |
| 2003/0101480 A1 | 5/2003 | Hadlaczky et al. |
| 2003/0108914 A1 | 6/2003 | Hadlaczky |

FOREIGN PATENT DOCUMENTS

| | | |
|---|---|---|
| EP | 0338266 | 10/1989 |
| EP | 053133 | 8/1991 |
| EP | 0442174 | 8/1991 |
| EP | 0552829 | 7/1993 |
| EP | 0712272 | 5/1996 |
| EP | 0959134 | 11/1999 |
| WO | WO 89/09219 | 5/1989 |
| WO | WO 91/02066 | 2/1991 |
| WO | WO 91/13994 | 9/1991 |
| WO | WO 92/07080 | 4/1992 |
| WO | WO 93/05165 | 3/1993 |
| WO | WO 95/02319 | 1/1995 |
| WO | WO 95/12669 | 5/1995 |
| WO | WO 96/40965 | 12/1996 |
| WO | WO 97/06250 | 2/1997 |
| WO | WO 97/14026 | 4/1997 |
| WO | WO 97/40183 | 10/1997 |
| WO | WO 98/02562 | 1/1998 |
| WO | WO 98/08964 | 3/1998 |
| WO | WO 98/37223 | 8/1998 |
| WO | WO 98/51790 | 11/1998 |
| WO | WO 98/54342 | 12/1998 |
| WO | WO 98/55637 | 12/1998 |
| WO | WO 99/21977 | 5/1999 |
| WO | WO 99/67374 | 12/1999 |
| WO | WO 00/06715 | 2/2000 |
| WO | WO 00/07431 | 2/2000 |
| WO | WO 00/40723 | 7/2000 |
| WO | WO 00/46350 | 8/2000 |
| WO | WO 00/52155 | 9/2000 |
| WO | WO 00/52183 | 9/2000 |
| WO | WO 00/75289 | 12/2000 |
| WO | WO 00/75299 | 12/2000 |
| WO | WO 00/78985 | 12/2000 |
| WO | WO 01/00858 | 1/2001 |
| WO | WO 01/05962 | 1/2001 |
| WO | WO 01/11020 | 2/2001 |
| WO | WO 01/20011 | 3/2001 |
| WO | WO 01/27241 | 4/2001 |
| WO | WO 01/29241 | 4/2001 |
| WO | WO 00/78976 | 8/2001 |
| WO | WO 01/59091 | 8/2001 |
| WO | WO 01/64024 | 9/2001 |
| WO | WO 01/77357 | 10/2001 |
| WO | WO 02/00842 | 1/2002 |
| WO | WO 02/04629 | 1/2002 |
| WO | WO 02/08409 | 1/2002 |
| WO | WO 02/29068 | 4/2002 |
| WO | WO 02/50288 | 6/2002 |
| WO | WO 02/057464 | 7/2002 |
| WO | WO 02/059296 | 8/2002 |
| WO | WO 02/059330 | 8/2002 |
| WO | WO 02/067655 | 9/2002 |
| WO | WO 02/072849 | 9/2002 |
| WO | WO 02/081710 | 10/2002 |
| WO | WO 02/086144 | 10/2002 |
| WO | WO 02/086146 | 10/2002 |
| WO | WO 02/096923 | 12/2002 |
| WO | WO 03/028014 | 4/2003 |

OTHER PUBLICATIONS

Ferl et al in Buchanin et al 2000 Biochemistry and Molecular Biology of Plants, American Society of Plant Physiologists, Rockville, MD 20855.*

Harrington et al 1997 Nature Genetics, 15:345-354 submitted by Applicant.*

Hall et al 2004 Current Opinion in Plant Biology 7:108-114.*

Bryant et al 2001 Journal of Experimental Botany 52:193-202.*

Abdullah et al., "Efficient Plant Regeneration from Rice Protoplasts through Somatic Embryogenesis," *BioTechnology* 4: 1087-1090 (1986).

Abel et al., "Delay of Disease Development in Transgenic Plants that Express the Tobacco Mosaic Virus Coat Protein Gene," *Science* 232: 738-743 (1986).

Alfenito et al., "Molecular Characterization of a Maize B Chromosome Centric Sequence," *Genetics 135*: 589-597 (1993).

Alonso-Blanco et al., "Development of AFLP Based Linkage Map of L*er*, Col and Cvi *Arabidopsis thaliana* Ecotypes and Construction of a L*er*/Cvi Recombinant Inbred Line Population," *The Plant Journal* 14: 259-271 (1998).

Ananiev et al., "Chromosome-specific Molecular Organization of Maize (*Zea mays* L.) Centromeric Regions," *Proc. Natl. Acad. Sci. USA 95*: 13073-13078 (1998).

Ananiev et al., "A Knob-Associated Tandem Repeat in Maize Capable of Forming Fold-back DNA Segments: Are Chromosome Knobs Megatransposons?," *Proc. Natl. Acad. Sci. USA. 95*: 10785-10790 (1998).

Ananiev et al., "Complex Structure of Knob DNA on Maize Chromosome 9: Retrotransposon Invasion into Heterochromatin," *Genetics 149*: 2025-2037 (1998).

Ananiev et al., "Complex Structure of Knobs and Centromeric Regions in Maize Chromosomes," *Tsitol Genet.* 34: 11-5 (2000).

Aragon-Alcaide et al., "A Cereal Centromeric Sequence," *Chromosoma 105*: 261-8 (1996).

Araki et al., "Site-specific Recominanse, R, Encoded by Yeast Plasmid pSR1," *J. Mol. Biol.* 225: 25-37 (1992).

Areshchenkova et al., "Long Tomato Microsatellites are Predominantly Associated with Centromeric Regions," *Genome 42*: 536-44 (1999).

Armstrong et al., "Physical Mapping of DNA Repetitive Sequences to Mitotic and Meiotic Chromosomes of *Brassica oleracea* var. *alboglabra* by Fluorescence in situ Hybridization," *Heredity 81*: 666-673 (1998).

Barki-Golan et al., "Studies on Growth Inhibition by Lectins of Penicillia and Aspergilli," *Arch. Microbiol.* 116: 119-124 (1978).

Baum et al., "The Centromeric K-Type Repeat and the Central Core are Together Sufficient to Establish a Functional *Schizosaccharomyces pombe* Centromere," *Molecular Biology of the Cell 5*: 747-761 (1994).

Bell et al., "Assignment of 30 Microsatellite Loci to the Linkage Map of *Arabidopsis*," *Genomics 19*: 137-144 (1994).

Bernal et al., "Changes in Soluble Carbohydrates During Seed Storage," *Plant Physiol. 98*: 1207-1210 (1992).

Berzal-Herranz et al., "In Vitro Selection of Active Hairpin Ribozymes by Sequential RNA-Catalyzed Cleavage and Ligation Reactions," *Genes & Development 6*: 129-134 (1992).

Bevan et al., "Clearing a Path Through the Jungle: Progress in *Arabidopsis* Genomics," *BioEssays 21*: 110-120 (1999).

Bevan et al., "Structure and Transcription of the Nopaline Synthase Gene Region of T-DNA," *Nucleic Acids Research 11*: 369-385 (1983).

Birchler, "Do These Sequences Make CENs Yet?" *Genome Research 7*: 1035-1037 (1997).

Blackman et al., "Maturation Proteins and Sugars in Dessiccation Tolerance of Developing Soybean Seeds," *Plant Physiol 100*: 225-230 (1992).

Bloom, "The Centromere Frontier: Kinetochore Components, Microtubule-Based Motility, and the CEN-Value Paradox," *Cell 73*: 621-624 (1993).

Bol et al., "Plant Pathogenesis-related Proteins Induced by Virus Infection," *Annu. Rev. Phytopath. 28*: 113-138 (1990).

Bowler et al., "Superoxide Dismutase and Stress Tolerance," *Annu. Rev. Plant Physiol. Plant Mol. Biol.* 43: 83-116 (1992).

Brandes et al., "Multiple Repetitive DNA Sequences in the Paracentromeric Regions of *Arabidopsis thaliana* L..," *Chromosome Res. 5*: 238-46 (1997).

Branson et al., "Potential for Utilizing Resistance from Relatives of Cultivated Crops," *Proceedings North Central Branch Entomological Society of America 27*: 9195 (1972).

Brisson et al., "Expression of a Bacterial Gene in Plants by Using a Viral Vector," *Nature 310*: 511-516 (1984).

Broach et al., "Transformation in Yeast: Development of a Hybrid Cloning Vector and Isolation of the CAN1 Gene," *Gene 8*: 121-133 (1979).

Broekaert et al., "A Chitin-Binding Lectin from Stinging Nettle Rhizomes with Antifungal Properties," *Science 245*: 1100-1102 (1989).

Buchowicz, J., "Nuclear Extrachromosomal DNA of Higher Plants," *Acta Biochim Pol. 44*: 13-19 (1977).

Burke et al., "Cloning of Large Segments of Exogenous DNA into Yeast by Means of Artificial Chromosome Vectors," *Science 236*: 806-812 (1987).

Bytebier et al., "T-DNA Organization in Tumor Cultures and Transgenic Plants of the Monocotyledon *Asparagus officinalis*," *Proc. Natl. Acad. Sci. USA 84*: 5345-5349 (1987).

Callis et al., "Introns Increase Gene Expression in Cultured Maize Cells," *Genes & Development 1*: 1183-1200 (1987).

Cambareri et al., "Structure of the Chromosome VII Centromere Region in *Neurospora crassa*: Degenerate Transposons and Simple Repeats," *Molecular and Cellular Biology 18*: 5465-5477 (1998).

Campbell, "The Production and Characterization of Rodent and Human Hybridomas," *Laboratory Techniques in Biochemistry and Molecular Biology 13*: 75-83 (1984).

Capecchi, "High Efficiency Transformation by Direct Microinjection of DNA into Cultured Mammalian Cells," *Cell 22*: 479-488 (1980).

Carbon et al., "Centromere Structure and Function in Budding and Fission Yeasts," *The New Biologist 2*: 10-19 (1990).

Carbon et al., "Structural and Functional Analysis of a Yeast Centromere (CEN3)," *J. Cell Sci. Suppl. 1*, 43-58 (1984).

Carbon et al., *Recombinant Molecules: Impact on Science and Society*, Raven Press: 335-378 (1977).

Carpenter et al., "On the Control of the Distribution of Meiotic Exchange in *Drosophila melanogaster*," *Genetics 101*: 81-89 (1982).

Cech et al., "In Vitro Splicing of the Ribosomal RNA Precursor of Tetrahymena: Involvement of a Guanosine Nucleotide in the Excision of the Intervening Sequence," *Cell 27*: 487-496 (1981).

Cepko et al., "Construction and Applications of a Highly Transmissible Murine Retrovirus Shuttle Vector," *Cell 37*: 1053-1062 (1984).

Chandler et al., "Two Regulatory Genes of the Maize Anthocyanin Pathway are Homologous: Isolation of B Utilizing R Genomic Sequences," *The Plant Cell 1*: 1175-1183 (1989).

Chang et al., "Restriction Fragment Length Polymorphism Linkage Map for *Arabidopsis thaliana*," *Proc. Natl. Acad. Sci USA 85*: 6856-6860 (1988).

Charlesworth et al., "The Evolution of Restricted Recombination and the Accumulation of Repeated DNA Sequences," *Genetics 112*: 947-962 (1986).

Charlesworth et al., "The Evolutionary Dynamics of Repetitive DNA in Eukaryotes," *Nature 371*: 215-220 (1994).

Cheng et al., "Functional Rice Centromeres are Marked by a Satellite Repeat and a Centromere-Specific Retrotransposon," *Plant Cell. 14*: 1691-1704 (2002).

Choi et al., "Construction and Characterization of a Bacterial Artificial Chromosome Library of *Arabidopsis thaliana*," *Plant Molecular Biology Reporter 13*: 124-129 (1995).

Choo, "Turning on the Centromere," *Nature Genetics 18*: 3-4 (1998).

Choo, "Why Is the Centromere So Cold?"*Genome Research 8*: 81-82 (1998).

Chowrira et al., "In Vitro and In Vivo Comparison of Hammerhead, Hairpin, and Hepatitis Delta Virus Self-processing Ribozyme Cassettes," *The Journal of Biological Chemistry 269*: 25856-25864 (1994).

Christou et al., "Stable Transformation of Soybean Callus by DNA-Coated Gold Particles," *Plant Physiol. 87*: 671-674 (1988).

Chu et al., "Separation of Large DNA Molecules by Contour-Clamped Homogenous Electric Fields," *Science 234*: 1582-1585 (1986).

Chye et al., "Characterization of *TSCL*, A Nonviral Retroposon from *Arabidopsis thaliana*," *Plant Molecular Biology 35*: 893-904 (1997).

Clapp, "Somatic Gene Therapy into Hemotopoietic Cells," *Clinics of Perinatology 20*: 155-168 (1993).

Clarke et al., "Centromeres: Proteins, Protein Complexes, and Repeated Domains at Centromeres of Simple Eukaryotes," *Genetics and Development 8*: 212-218 (1998).

Clarke et al., "Analysis of Centromeric DNA in the Fission Yeast *Schizosaccharomyces pombe*," *Proc. Natl. Acad. Sci. USA 83*: 8253-8257 (1986).

Clarke et al., "Isolation of a Yeast Centromere and Construction of Functional Small Circular Chromosomes," *Nature 287*: 504-509 (1980).

Cohen et al., "Construction of Biologically Functional Bacterial Plasmids In Vitro," *Proc. Nat. Acad. Sci. USA 70*: 3240-3244 (1973).

Conkling et al., "Isolation of Transcriptionally Regulated Root-Specific Genes from Tobacco," *Current Opinion Plant Physiol. 93*: 1203-1211 (1990).

Copenhaver, et al., "Centromeres in the Genomic Era: Unraveling Paradoxes," *Plant Biology 2*: 104-108 (1999).

Copenhaver et al., "Assaying Genome-wide Recombination and Centromere Functions with *Arabidopsis* tetrads," *Proc. Natl. Acad. Sci. USA*, 95: 247-252 (1998).

Copenhaver et al., "Tetrad Analysis in Higher Plants: A Budding Technology," *Plant Physiol.*, 124: 7-16 (2000).

Copenhaver et al., "RFLP and Physical Mapping with an rDNA-specific Endonuclease Reveals that Nucleolus Organizer Regions of *Arabidopsis thaliana* Adjoin the Telomeres on Chromosomes 2 and 4," *Plant Journal 9*: 259-276 (1996).

Copenhaver et al., "Genetic Definition and Sequence Analysis of *Arabidopsis* Centromeres," *Science 286*: 2468-2474 (1999).

Copenhaver et al., "Two-dimensional RFLP analyses Reveal Megabase-sized Clusters of rRNA Gene Variants in *Arabidopsis*

*thaliana*, Suggesting Local Spreading of Variants as the Mode for Gene Homogenization During Concerted Evolution," *The Plant Journal 9*: 273-282 (1996).
Copenhaver et al., "Use of RFLPs Larger than 100 kbp to Map Position and Internal Organization of the Nucleolus Organizer Region on Chromosome 2 in *Arabidopsis thaliana*," *Plant Journal 7*: 273-286 (1995).
Copenhaver et al.,"Assaying Genomic-Wide Recombination and Centromere Functions with *Arabidopsis* Tetrads," *Proc. Natl. Acad. Sci. USA 95*: 247-52 (1998).
Copenhaver, "Using *Arabidopsis* to Understand Centromere Function: Progress and Prospects," *Chromosome Res. 2993*: 11: 255-62 (2003).
Coxson et al., "Pulse Release of Sugars and Polyols from Canopy Bryophytes in Tropical Montane Rain Forest (Guadeloupe, French West Indies)," *Biotropica 24*: 121-133 (1992).
Creusot et al., "The CIC Library: A Large Insert YAC Library for Genome Mapping in *Arabidopsis thaliana*," *The Plant Journal 8*: 763-770 (1995).
Cristou et al., "Stable Transformation of Soybean Callus by DNA-Coated Gold Particles,"*Plant Physiol. 87*: 671-674 (1988).
Cuozzo et al., "Viral Protection in Transgenic Tobacco Plants Expressing the Cucumber Mosaic Virus Coat Protein or Its Antisense RNA," *Bio Technology 6*: 549-557 (1988).
Curiel et al., "High-efficiency Gene Transfer Mediated by Adenovirus Coupled to DNA-polylysine Complexes," *Hum. Gen. Ther. 3*: 147-154 (1992).
Curiel et al., "Adenovirus Enhancement of Transferrin-Polylysine-Mediated Gene Delivery," *Proc. Natl. Acad. Sci. USA 88*: 8850-8854 (1991).
Cutler et al. , "Winter Flounder Antifreeze Protein Improves the Cold Hardiness of Plant Tissues," *J. Plant Physiol. 135*: 351-354 (1989).
Czapla et al., "Effect of Plant Lectins on the Larval Development of European Corn Borer (*Lepidoptera: Pyralidae*) and Southern Corn Rootworm (*Coleoptera: Chrysomelidae*)," *J. Econ Entomol 83*: 2480-2485 (1990).
Davies et al., "Leaf Senescence in a Nonyellowing Mutant of *Festuca pratensis*," *Plant Physiol. 93*: 588-595 (1990).
Dellaporta et al., "Molecular Cloning of the Maize *R-nj* Allele by Transposon Tagging with *Ac"*: *Chromosome Structure and Function: Impact of New Concepts*, 18th *Stadler Genetics Symposium 11*: 263-282 (1988).
Dennis et al., "Knob Heterochromatin Homology in Maize and Its Relatives," *J. Mol. Evol. 20*: 341-350 (1984).
Depicker et al., "A Negative Selection Scheme for Tobacco Protoplast-Derived Cells Expressing the T-DNA Gene 2," *Plant Cell Reports 7*: 63-66 (1988).
Di Laurenzio et al., "The SCARECROW Gene Regulates an Asymmetric Cell Division that Is Essential for Generating the Radial Organization of the *Arabidopsis* Root," *Cell*, 86: 423-433 (1996).
Discussion with David Baltimore as Moderator, "Recombinant Molecules: Impact on Science and Society": 337-352, New York, 1977.
Donahue et al., "The Nucleotide Sequence of the *HIS4* Region of Yeast," *Gene. 18*: 47-59 (1982).
Dong et al., "Rice (*Oryza Sativa*) Centromeric Regions Consist Of Complex DNA," *Proc. Natl. Acad. Sci. USA 95*: 8135-40 (1998).
Dure III et al., "Common Amino Acid Sequence Domains Among the LEA Proteins of Higher Plants," *Plant Molecular Biology 12*: 475-486 (1989).
duSart et al., "A Functional Neo-centromere Formed Through Activation of a Latent Human Centromere and Consisting of Non-alpha Satellite DNA," *Nature Genetics 16*: 144-153 (1997).
Earnshaw et al., "Proteins of the Inner and Outer Centromere of Mitotic Chromosomes," *Genome 31*: 541-552 (1989).
Earnshaw et al., "When is a Centromere Not a Kinetochore?" *Journal of Cell Science 99*: 1-4 (1991).
Ebert et al., "Identification of an Essential Upstream Element in the Nopaline Synthase Promoter by Stable and Transient Assays," *Proc. Natl. Acad. Sci. USA 84*: 5745-5749 (1987).
Ecker, "PFGE and YAC Analysis of the *Arabidopsis* Genome," *Methods I*: 186-194 (1990).

Eglitis et al., "Retroviral Vectors for Introduction of Genes into Mammalian Cells," *BioTechniques 6*: 608-614 (1988).
Eglitis et al.,"Retroviral-mediated Gene Transfer into Hemapoietic Cells," *Avd. Exp. Med. Biol. 241*: 19-27 (1988).
Enomoto et al., "Mapping of the *pin* Locus Coding for a Site-Specific Recombinase that Causes Flagellar-Phase Variation in *Escherichia coli* K-12," *Journal of Bacteriology 156*: 663-668 (1983).
Erdmann et al., "Glycosylglycerol Accumulation During Salt Acclimination of Two Unicellular Cyanobacteria," *Journal of General Microbiology 138*: 363-368 (1992).
Ferrin et al., "Selective Cleavage of Human DNA: RecA-Assisted Restriction Endonuclease (RARE) Cleavage," *Science 254*: 1494-1497 (1991).
Fitzpatrick, "Pleiotropic Gene Found in Barley Plant" *Gen. Engineering News* 13(5): 1, 22 (1993).
Fleig. et al., "Functional Selection for the Centromere DNA from Yeast Chromosome VIII," *Nuc. Acids. Res 23*: 922-924 (1995).
Forster et al., "Self-Cleavage of Plus and Minus RNAs of a Virusoid and a Structural Model for the Active Sites," *Cell 49*: 211-220 (1987).
Fraley et al., "The SEV Sysem: A New Disarmed TI Plasmid Vector System for Plant Transformation," *BioTechnology 3*: 629-635 (1985).
Fransz et al., "Cytogenetics for the Model System *Arabidopsis thaliana*," *The Plant Journal 13*: 867-876 (1998).
Fransz et al., "Integrated Cytogenetic Map of Chromosome Arm 4S Of *A. thaliana*: Structural Organization of Heterochromatic Knob and Centromere Region," *Cell. 100*: 367-76 (2000).
Frary et al., "Molecular Mapping of the Centromeres of Tomato Chromosomes 7 and 9," *Mol Gen Genet.*, 250: 295-304 (1996).
Fromm et al., "Expression of Genes Transferred into Monocot and Dicot Plant Cells by Electroporation," *Proc. Nat. Acad. Sci. USA 82*: 5824-5828 (1985).
Fromm et al., "Stable Transformation of Maize After Gene Transfer by Electroporation," *Nature 319*: 791-793 (1986).
Fujimara et al, "Regeneration of Rice Plants from Protoplasts," *Plant Tissue Culture Letters 2*: 74 (1985).
Fukui et al.., "Physical Arrangement of Retrotransposon-Related Repeats in Centromeric Regions of Wheat," *Plant Cell Physiology*, 42: 189-96 (2004).
Fynan et al., "DNA Vaccines: Protective Immunizations by Parenteral, Mucosal, and Gene-Gun Inoculations," *Proc. Nat. Acad. Sci. USA 90*: 11478-11482 (1993).
Gatehouse et al., "Effect of Seed Lectins from *Phaseolus vulgaris* on the Development of Larvae of *Callosobruchus maculatus*; Mechanism of Toxicity," *J. Sci. Food. Agric. 35*: 373-380 (1984).
Gefter et al., "A Simple Method for Polyethylene Glycol-promoted Hybridization of Mouse Myelome Cells," *Somatic Cell Genet. 3*: 231-236 (1977).
Gerlach et al., "Construction of a Plant Disease Resistance Gene from the Satellite RNA of Tobacco Ringspot Virus," *Nature 328*: 802-805 (1987).
Gindullis et al., "The Large-Scale Organization of the Centromeric Region in Beta Species," *Genome Res. 11*: 253-65 (2001).
Gindullis, et al., "Construction and Characterization of A BAC Library for the Molecular Dissection of a Single Wild Beet Centromere and Sugar Beet (*Beta Vulfaris*)," *Genome Analysis*, 44: 846-55 (2001).
Giordano et al., "Identification by Denaturing High-Performance Liquid Chromatography of Numerous Polymorphisms in a Candidate Region for Multiple Sclerosis Susceptibility," *Genomics*, 56: 247-253 (1999).
Goding, *Monoclonal Antibodies: Principles and Practice*, Academic Press, Orlando, Florida, 60-74 (1986).
Golic et al., "The FLP Recombinase of Yeast Catalyzes Site-Specific Recombinatioin in the *Drosophila* Genome" *Cell 59*: 499-509 (1989).
Goring et al., "Transformation of a Partial Nopaline Synthase Gene into Tobacco Suppresses the Expression of a Resident Wild-type Gene," *Proc. Natl. Acad. Aci. USA* 88, 1770-1774 (1991).
Graham et al., "Transformation of Rat Cells by DNA of Human Adenovirus 5," *Virology 54*: 536-539 (1973).

Grellet et al., "Organization and Evolution of a Higher Plant Alphoid-like Satellite DNA Sequence," *J. Mol. Biol.* 187: 495-507(1986).

Grill et al., "Construction and Characterization of a Yeast Artificial Chromosome Library of *Arabidopsis* Which Is Suitable for Chromosome Walking," *Mol. Gen. Genet.* 226: 484-490 (1991).

Guerrero et al., "Turgo-Responsive Gene Transcription and RNA Levels Increase Rapidly When Pea Shoots Are Wilted. Sequence and Expression of Three Inducible Genes," *Plant Molecular Biology* 15: 11-26 (1990).

Gupta et al., "Increased Resistance to Oxidative Stress in Transgenic Plants that Overexpress Chloroplastic Cu/Zn Superoxide Dismutase," *Proc. Natl. Acad. Sci. USA* 90: 1629-1633 (1993).

Gutierrez-Marcos et al., "Three Members of a Novel Small Gene-Family from *Arabidopsis thaliana* Able to Complement Functionally an *Escherichia coli* Mutant Defective in PAPS Reducatase Activity Encode Proteins with a Thioredoxin-like Domain and "APS Reductase" Activity," *Proc. Natl. Acad. Sci USA* 93: 13377-133824 (1996).

Haaf et al., "Integration of Human Satellite DNA into Simian Chromosomes: Centromere Protein Binding and Disruption of Normal Chromosome Segregation," *Cell* 70: 681-696 (1992).

Hadlaczky et al., "Centromere Formation in Mouse Cells Cotransformed with Human DNA and a Dominant Marker Gene," *Proc. Natl. Acad. Sci., USA* 88: 8106-8110 (1991).

Hauge et al., "Mapping the *Arabidopsis* Genome," *Symp. Society for Experimental Biology*, 45: 45-56 (1991).

Hall, et al., "The Rapidly Evolving Field Of Plant Centromeres," Department of Molecular Genetics and Cell Biology, The University of Chicago, Chicago, Illinois 60637, USA, *Curr. Opin Plant Biol.* 7108-14 (2002).

Hamilton et al., "Stable Transfer of Intact High Molecular Weight DNA into Plant Chromosomes," *Proc. Natl. Acad. Sci. USA* 93: 9975-9979(1996).

Hamilton, "A Binary BAC System for Plant Transformation with High-Molecular-Weight DNA," *Gene* 4: 200: 107-116 (1997).

Hammock et al., "Expression and Effects of the Juvenile Hormone Esterase in a Baculovirus Vector," *Nature* 344: 458-463 (1990).

Harrington et al., "Formation of *de novo* Centromeres and Construction of First-generation Human Artificial Microchromosomes," *Nature Genetics* 15: 345-354 (1997).

Harrison et al., "Centromeric Repetitive DNA Sequences in the Genus *Brassica*," *Theor. Appl. Genet.*, 90: 157-165 (1995).

Haseloff et al., "Removal of a Cryptic Intron and Subcellular Localization of Green Fluorescent Protein Are Required to Mark Transgenic *Arabidopsis* Plants Brightly," *Proc. Natl. Acad. Sci. USA* 94: 2122-2127 (1997).

Hegemann et al., "The Ceontromere of Budding Yeast," *BioEssays* 15: 451-460 (1998).

Heller et al., "Mini-Chromosomes Derived from the Human Y Chromosome by Telomere Directed Chromosome Breakage," *Proc. Natl. Acad. Sci. USA* 93: 7125-7130 (1996).

Hemenway et al., "Analysis of the Mechanism of Protection in Transgenic Plants Expressing the Potato Virus X Coat Protein or its Antisense RNA," *The EMBO Journal* 7: 1273-1280 (1988).

Heslop-Harrison et al., "Polymorphisms and Genomic Organization of Repetitive DNA from Centromeric Regions of *Arabidopsis* Chromosomes," *Plant Cell.* 11: 31-42 (1999).

Hilder et al., "A Novel Mechanism of Insect Resistance Engineered into Tobacco," *Nature* 330: 160-163 (1987).

Hinchee et al., "Production of Transgenic Soybean Plants Using *Agrobacterium*-Mediated DNA Transfer," *BioTechnology* 6: 915-922 (1988).

Hoess et al., "P1 Site-Specific Recombination: Nucleotide Sequence of the Recombining Sites," *Proc. Nat. Acad. Sci. USA* 79: 3398-3402 (1982).

Houben et al., "DNA and Proteins of Plant Centromeres," *Current Opinion in Plant Biology* 6: 554-560 (2003).

Hsiao et al., "High-Frequency Transformation of Yeast by Plasmids Containing the Cloned Yeast ARG4 Gene," *Proc. Nat. Acad. Sci. USA* 76: 3829-3833 (1979).

Hudakova et al., : Sequence Organization of Barley Centromeres, *Nucleic Acids Resources*, 29: 5029-35 (2001).

Hudspeth et al., "Structure and Expression of the Maize Gene Encoding the Phosphoenolpyruvate Carboxylase Isozyme Involved in $C_4$ Photosynthesis," *Plant Molecular Biology* 12: 579-589 (1989).

Hwang et al., "Identification and Map Position of YAC Clones Comprising One-third of the *Arabidopsis* genome," *The Plant Journal* 1: 367-374 (1991).

Ikeda, et al., "Genetic Studies of Avermectin Biosynthesis in *Streptomyces avermitilis,*" *Journal of Bacteriology* 16: 5615-5621 (1987).

Ikeno, et al., "Construction of YAC-based Mammalian Artificial Chromosomes," *Nature Biotechnology* 16: 431-439 (1998).

Ikuta et al., "The Alpha-Amylase Gene as a Marker for Gene Cloning: Direct Screening of Recombinant Clones," *BioTechnology* 8: 241-242 (1990).

Inohara et al., "Two Genes, *atp*C1 and *atp*C2, for the Subunit of *Arabidopsis thaliana* Chloroplast ATP Synthase," *The Journal of Biological Chemistry* 266: 7333-7338 (1991).

Jiang et al., "A Conserved Repetitive DNA Element Located in the Centromeres of Cereal Chromosomes," *Proc Natl Acad Sci USA.*, 93: 4210-4213 (1996).

Jiang et al., "A Molecular View of Plant Centromeres," *Trends in Plant Science* 8: 570-575 (2003).

Jin et al., Maize-Centromeres: Organization and Functional Adaptation in the Genetic Background of Oat, Department of Horticulture, University of Wisconsin-Madison, Madison, Wisconsin 53706, USA, *Plant Cell.* 16: 57-81 (2004).

Johnston et al., "Gene Gun Transfection of Animal Cells and Genetic Immunization," *Methods in Cell Biology* 43: 353-363 (1994).

Jones et al., "T-DNA Structure and Gene Expression in Petunia Plants Transformed by *Agrobacterium tumafaciens C*58 Derivatives," *Mol. Gen. Genet.* 207: 478-485 (1987).

Jones et al:, "High Level Expression of Introduced Chimaeric Genes in Regenerated Transformed Plants," *The EMBO Journal* 4: 2411-2418 (1985).

Jorgensen et al., "T-DNA is Organized Predominantly in Inverted Repeat Structures in Plants Transformed with *Agrobacterium tumafaciens* C58 Derivatives," *Mol. Gen. Genet.* 207: 471-477 (1987).

Jouanin et al., "Localization and Restriction Maps of Replication Origin Regions of the Plasmids of *Agrobacterium rhizogenes* Strain $A_{43}$," *Mol. Gen. Genet.* 201: 370-374 (1985).

Joyce, "RNA Evolution and the Origins of Life," *Nature* 338: 217-224 (1989).

Karpen, "Position-effect Variegation and the New Biology of Heterochromatin," *Current Opinion in Genetics and Development* 4: 281-291 (1994).

Karsten et. al., "Polyol Content of Bostrychia and Stictosiphonia (Rhodomelaceae, Rhodophyta) from Field and Culture;" *Botanica Marina* 35: 11-19 (1992).

Kaasen et al., "Molecular Cloning and Physical Mapping of the otsBA Genes, Which Encode the Osmoregulatory Trehalose Pathway of *Escherichia coli*: Evidence that Transcription Is Activated by KatF (AppR)," *Journal of Bacteriology* 174: 889-898 (1992).

Kaszás et al., "Misdivision Analysis of Centromere Structure in Maize," *The EMBO Journal* 15: 5246-5255 (1996).

Kato et al., "Foreign DNA Introduced by Calcium Phosphate is Integrated into Repetitive DNA Elements of the Mouse L Cell Genome," *Molecular and Cellular Biology* 6: 1787-1795 (1986).

Katz et al., "Cloning and Expression of the Tyrosinase Gene from *Streptomyces antibioticus* in *Streptomyces lividans,*" *Journal of General Microbiology* 129: 2703-2714 (1983).

Kim et al., "Three-Dimensional Model of the Active Site of the Self-Splicing rRNA Precursor of Tetrahymena," *Proc. Nat. Acad. Sci. USA* 84: 8788-8792 (1987).

Kishii, et al., "A Tandem Repetitive Sequence Located in the Centromeric Region of Common Wheat (*Triticum Aestivum*) Chromosomes," *Chromosome Resources*, 9: 417-28 (2001).

Klee et al., "Vectors for Transformation of Higher Plants," *BioTechnology* 3: 637-642 (1985).

Klein et al., "High-Velocity Microprojectiles for Delivering Nucleic Acids into Living Cells," *Nature* 327: 70-73 (1987).

Klein et al., "Stable Genetic Transformation of Intact Nicotiana Cells by the Particle Bombardment Process," *Proc. Nat. Acad. Sci. USA* 85: 8502-8505 (1988).

Kohler et al., "Continous Cultures of Fused Cells Secreting Antibody of Predefined Specificity," *Nature* 256: 495-497 (1975).

Kohler et al., "Derivation of Specific Antibody-Producing Tissue Culture and Tumor Lines by Cell Fusion," *Eur. J. Immunol.* 6: 511-519 (1976).

Kolchinsky et al., "A Major Satellite DNA of Soybean is a 92-base Pairs Tandem Repeat" *Theor. Appl. Genet.* 90: 621-626 (1995).

Konieczny et al., "A Superfamily of *Arabidopsis thaliana* Retrotransposons," *Genetics* 127: 801-809 (1991).

Konieczny et al., "A Procedure for Mapping *Arabidopsis* Mutations Using Co-dominant Ectotype-specific PCR-based Markers," *The Plant Journal* 4: 403-310 (1993).

Koorneef et al., "Trisomics in *Arabidopsis thaliana* and the Location of Linkage Groups," *Genetica* 61: 41-46 (1983).

Koorneef ,"Linkage Map of *Arabidopsis thaliana* (2n=10)," In S.J. O'Brien, ed., *Genetic Maps 1987: A Compilation of Linkage and Restriction Maps of Genetically Studied Organisms*, 742-745 (1987).

Koorneef, "The Use of Telotrisomics for Centromere Mapping in *Arabidopsis thaliana* (L.) Heynh.," *Genetica* 62: 33-40 (1983).

Koster et al., "Sugars and Desiccation Tolerance in Seeds," *Plant Physiol.* 88: 829-832 (1988).

Kotani et al., "Structural Analysis and Complete Physical Map of *Arabidopsis thaliana* Chromosome 5 Including Centromeric Telomeric Regions," *DNA Research* 6: 381-386 (1999).

Kuhn et al., "Clustered tRNA Genes in *Schizosaccharomyces pombe* Centromeric DNA Sequence Repeats," *Proc. Nat. Acad. Sci. USA* 88: 1306-1310 (1991).

Kumekawa et al., "The Size and Sequence Organization of the Centromeric Region of *Arabiodpsis thaliana* Chromosome 5," *DNA Resources*, 7: 315-21 (2000).

Kurata et al.,, "Rice Genome Organization: The Centromere and Genome Interactions," *Ann Bot* 90: 427-35 (2002).

Kyte et al., "A Simple Method for Displaying the Hydropathic Character of a Protein," *J. Mol. Biol.* 157: 105-132 (1982).

Lakshmikumarin et al., "Isolation and Characterization of a Highly Repetitive DNA of *Brassica campestris*," *Plant Molecular Biology* 14: 447-448 (1990).

Lawton et al., "Expression of a Soybean—conclycinin Gene under the Control of the Cauliflower Mosaic Virus 35S and 19S Promoters in Transformed Petunia Tissues," *Plant Molecular Biology* 9: 315-324 (1987).

Lechner et al., "A 240 kd Multisubunit Protein Complex, CBF3, is a Major Component of the Budding Yeast Centromere," *Cell* 64: 717-725 (1991).

Lee et al., "Use of Cloned *mtl* Genes of *Escherichia coli* to Introduce *mtl* Deletion Mutations into the Chromosome," *Journal of Bacteriology* 153: 685-692 (1983).

Levings III, "The Texas Cytoplasm of Maize: Cytoplasmic Male Sterility and Disease Susceptibility," *Science* 250: 942-947 (1990).

Li et al., "Direct Electrophoretic Detection of the Allelic State of Single DNA Molecules in Human Sperm by Using the Polymerase Chain Reaction," *Proc. Natl. Acad. Sci. USA* 87: 4580-4584 (1990).

Li et al., "CUE1: A Mesophyll Cell-Specific Positive Regulator of Light-Controlled Gene Expression in *Arabidopsis*," *The Plant Cell* 7: 1599-1610 (1995).

Lieber et al., "Selection of Efficient Cleavage Sites in Target RNAs by Using a Ribozyme Expression Library," *Molecular and Cellular Biology* 15: 540-551 (1995).

Lin et al., "Sequence and Analysis of Chromosome 2 of the Plant *Arabidopsis thaliana*," *Nature* 402: 761-768 (1999).

Liu, Y.G., et al., "Complementation of Plant Mutants with Large Genomic DNA Fragments by a Transformation-Competent Artificial Chromosome Vector Accelerates Positional Cloning," *Proc. Natl. Acad. Sci. USA* 96: 6635-6640 (1999).

Lohe et al., "Return of the H-word (heterochromatin)," *Current Opinion in Genetics and Development* 5: 746-755 (1995).

Loomis et al., "Cyroprotective Capacity of End Products of Anaerobic Metabolism," *The Journal of Experimental Zoology* 252: 9-15 (1989).

Lorz et al., "Gene Transfer to Cereal Cells Mediated by Protoplast Transformation," *Mol. Gen. Genet.* 199: 178-182 (1985).

Louis, "Corrected Sequence for the Right Telomere of *Saccharomyces cerevisiae* Chromosome III," *Yeast* 10: 271-274 (1994).

Lu et al., "High Efficiency Retroviral Mediated Gene Transduction into Single Isolated Immature and Replatable $CD34^{3+}$ Hemotopoietic Stem/Progenitor Cells from Human Umbilical Cord Blood," *J. Ex. Med.* 178: 2089-2096 (1993).

Lugo et al., "Changes in Soluble Carbohydrates during Seed Storage," *Plant Physiol.* 98: 1207-1210 (1992).

Maeser et al., "The Gin Recombinase of Phase Mu Can Catalyse Site-Specific Recombination in Plant Protoplasts," *Mol. Gen. Genet* 230: 170-176 (1991).

Mahtani et al., "Physical and Genetic Mapping of the Human X Chromosome Centromere: Repression of Recombination," *Genome Research* 8: 100-110 (1998).

Maloy, S.R., Experimental Techniques in Bacterial Genetics , Jones and Bartlett, *Ann. N.Y. Acad. Sci.* 646 (1991).

Maluszynska et al., "Localization of Tandemly Repeated DNA Sequences in *Arabidopsis thaliana*," *The Plant Journal* 1: 159-166 (1991).

Maluszynska et al., Molecular Cytogenetics of the Genus *Arabidopsis*: In situ Localization of rDNA Sites, Chromosome Numbers and Diversity in Centromeric Heterochromatin,: *Annals of Botany* 71: 479-484 (1993).

Marcotte et al., "Regulation of a Wheat Promoter by Abscisic Acid in Rice Protoplasts" *Nature* 335: 454 (1988).

Mariani et al., "Induction of Male Sterility in Plants by a Chimaeric Ribonuclease Gene," *Nature* 357: 737-741 (1990).

Marra et al., "A Map for Sequence Analysis of the *Arabidopsis thaliana* Genome," *Nature Genetics* 22: 265-270 (1999).

Martinex-Zapater et al., "A Highly Repeated DNA Sequence in *Arabidopsis thaliana,"* *Mol. Gen. Genet* 204: 417-423 (1986).

Matsuura et al., "The *sre* Gene (ORF459) Encodes a Site-Specific Recombinase Responsible for Integration of the R4 Phage Genome," *Journal of Baceteriology* 178: 3374-3376 (1996).

McCabe et al., "Stable Transformation of Soybean (*Glycine Max*) by Particle Acceleration," *BioTechnology* 6: 924-926 (1988).

Miller et al., "Retrotransposon-Related DNA Sequences in the Centromeres of Grass Chromosomes," *Genetics* 150: 1615-23 (1998).

Mortimer et al., "Genetic Mapping in *Saccharomyces cerevisiae*," Department of Biophysics and Medical Physics and Donner Laboratory, University of California at Berkeley: 11-26 (1981).

Mozo et al., "A Complete BAC-based Physical Map of the *Arabidopsis thaliana* Genome," *Nature Genetics* 22: 271-275 (1999).

Mozo et al., "Construction and Characterization of the IGF *Arabidopsis* BAC Library," *Mol. Gen. Genet.* 258: 562-570 (1998).

Mundy et al. "Abscisic Acid and Water-stress Induce the Expression of a Novel Rice Gene," *The EMBO Journal* 7: 2279-2286 (1988).

Murakami et al., "The Bialaphos Biosynthetic Genes of *Streptomyces hygroscopicus*: Molecular Cloning and Characterization of the Gene Cluster," *Mol. Gen. Genet.* 205: 42-50 (1986).

Murata et al., "Physical Mapping of the 5S Ribosomal RNA Genes in *Arabidopsis thaliana* by Multi-Color Fluorescence in situ Hybridization with Cosmid Clones," *The Plant Journal* 12: 31-37 (1997).

Murata et al., "Centromeric Repetitive Sequences In *Arabiidopsis thaliana,"* *Jpn J Genet.* 69: 361-370 (1994).

Murdock et al., "Biological Efects of Plant Lectins on the Cowpea Weevil," *Phytochemistry* 29: 85-89 (1990).

Murphy et al., "Localization of Centromere Function in a Drosophila Minichromosome," *Cell* 82: 599-609 (1995).

Murray et al., "Construction of Artificial Chromosomes in Yeast," *Nature* 305: 189-193(1983).

Mysore et al., "An *Arabidopsis* Histone H2A Mutant is Deficient in *Agrobacterium* T-DNA Integration," *Proc. Natl. Acad, Sci USA* 97: 948-953 (2000).

Mysore et al., "*Arabidopsis* Ecotypes and Mutants That Are Recalcritant to *Agrobacterium* Root Transformation Are Susceptible to Germ-line Transformation," *The Plant Journal 21*: 9-16 (2000).

Nagaki et al., "Molecular and Cytological Analysis of Large Tracks of Centrometic DNA Reveal the Structure and Evolutionary Dynamics of Maize Centromeres," *Genetics 163*: 759-70 (2003).

Nagaki et al., "Sequencing of a Rice Centromere Uncovers Active Genes", *Nature Genet. 36*: 138-145 (2004).

Nakamura et al., "Construction of an 800-KB Contig in the Near-Centromeric Region of the Rice Blast Resistance Gene *Pi-ta2* Using a Highly Representative Rice BAC Library," *Mol Gen Genet. 254*: 611-620 (1997).

Napoli et al., "Introduction of a Chimeric Chalcone Synthase Gene into Petunia Results in Reversible Co-Suppression of Homologous Genes *in trans*," *The Plant Cell 2*: 279-298 (1990).

Negrutiu, et al. "Plant Protoplasts as Genetic Tool: Selectable Markers for Developmental Studies," *Int. J. Dev. Biol. 36*: 73-84 (1992).

Nester et al., "A Molecular and Physiological Analysis," *Ann. Rev. Plant Physiol. 35*: 387-413 (1984).

Nester et al., "Crown Gall: A Molecular and Physiological Analysis," *Ann Rev. Plant Physiol 35*: 387-413(1984).

Nicklas, "The Forces That Move Chromosomes in Mitosis," *Ann. Rev. Biophys. Biophys. Chem. 17*: 431-449 (1988).

Nonomura et al., "Organization Of The 1.9-KB Repeat Unit RCE1 in the Centromeric Region of Rice Chromosomes," *Mol Gen Genet. 261*: 1-10 (1999).

Nonomura, et al., "The Centromere Composition Of Multiple Repetitive Sequences on Rice," *Chromosome 5*, 110: 284-91 (2001).

Noutoshi et al., "Designing of Plant Artificial Chromosome (PAC) by Using the Chlorella Smallest Chromosome as a Model System," *Nucleic Acids Symp. Ser. 37*: 143-4 (1997).

Nussbaum et al., "Construction and Propagation of a Defective Simian Virus 40 Genome Bearing an Operator from Bacteriophage," *Proc. Nat. Acad. Sci. USA 73*: 1068-1072 (1976).

Odell et al., "Identification of DNA Sequences Required for Activity of the Cauliflower.Mosaic Virus 35S Promoter," *Nature 313*: 810-812 (1985).

Ohmori et al., "Nucleotide Sequence of the Region Required for Maintenance of Colicin E1 Plasmid," *Mol. Gen. Genet. 176*: 161-170 (1979).

Omirulleh et al., "Activity of a Chimeric Promoter with the Doubled CaMV 35S Enhancer Element in Protoplast-derived Cells and Transgenic Plants in Maize," *Plant Molecular Biology 21*: 415-428 (1993).

Ow et al., "Transient and Stable Expression of the Firefly Luciferase Gene in Plant Cells and Transgenic Plants," *Science 234*: 856-859 (1986).

Page et al., "Characterization of a Maize Chromosome 4 Centromeric Sequence: Evidence for an Evolutionary Relationship with the B Chromosome Centromere," *Genetics 159*: 291-301 (2001).

Palukaitis et al., "Characterization of a Viroid Associated with Avocado Sunblotch Disease," *Virology 99*: 145-151 (1979).

Peacock et al., "Highly Repeated DNA Sequence Limited to Knob Heterochromatin in Maize," *Proc. Nat. Acad. Sci. USA 78*: 4490-4494 (1981).

Pelissier et al., "DNA Regions Flanking the Major *Arabidopsis thaliana* Satellite Are Principally Enriched in *Athila* Retroelement Sequences," *Genetica 97*: 141-151 (1996).

Pelissier et al., "*Athila*, A New Retroelement from *Arabidopsis thaliana.*," *Plant Mol. Biol. 29*: 441-552 (1995).

Perkins, "The Detection of Linkage in Tetrad Analysis," *Genetics 38*: 187-197 (1953).

Perlak et al., "Modification of the Coding Sequence Enhances Plant Expression of Insect Control Protein Genes," *Proc. Natl. Acad. Sci USA 88*: 3324-3328 (1991).

Perriman et al., "Extended Target-Site Specificity for a Hammerhead Ribozyme," *Gene 113*: 157-163 (1992).

Peterson et al., "Production of Transgenic Mice with Yeast Artificial Chromosomes," *TIG 13*: 61-66 (1997).

Phi-Van et al., "The Chicken Lysozyme 5' Matrix Attachment Region Increases Transcription from a Heterologous Promoter in Heterologous Cells and Dampens Position Effects on the Expression of Transfected Genes," *Molecular and Cellular Biology 10*: 2302-2307 (1990).

Piatowski et al., "Characterization of Five Abscisic Acid-Responsive cDNA Clones Isolated from the Dessication-Tolerant Plant *Craterostigma plantagineum* and Their Relationship to Other Water-Stress Genes," *Plant Physiol. 94*: 1682-1688 (1990).

Potrykus et al., "Direct Gene Transfer to Cells of a Graminaceous Monocot," *Mol. Gen. Genet. 199*: 183-188 (1985).

Prasher et al., "Cloning and Expression of the cDNA Coding for Aequorin, A Bioluminescent Calcium-binding Protein," *Biochem Biophys. Res. Commun 126*: 1259-1268 (1985).

Presting et al., "A *Ty3/gypsy* Retrotransposon-Like Sequence Localizes to the Centromeric Regions of Cereal Chromosomes," *Plant J. 16*: 721-8 (1998).

Preuss et al., "Tetrad Analysis Possible in *Arabidopsis* with Mutation of the QUARTET (QRT) Genes," *Science 264*: 1458-1460 (1994).

Price et al., "Systematic Relationships of *Arabidopsis*: A Molecular and Morphological Perspective," in Somerville, C. and Meyerowitz, E. (eds.), *Arabidopsis*, Cold Spring Harbor Press, New York (1995) pp. 7-19.

Prody et al., "Autolytic Processing of Dimeric Plant Virus Satellite RNA," *Science 231*: 1557-80 (1986).

Puechberty, J., "Genetic and Physical Analyses of the Centromeric and Pericentromeric Regions of Human Chromosome 5: Recombination Across 5cen," *Genomics 56*: 274-87 (1999).

Rathore et al., "Use of *bar* as a Selectable Marker Gene and for the Production of Herbicide-Resistant Rice Plants from Protoplasts," *Plant Molecular Biology 21*: 871-884 (1993).

Rattner et al., "The Structure of the Mammalian Centromere," *BioEssays 13*: 51-56 (1991).

Ravatn et al., "Int-B13, An Unusual Site-Specific Recombinase of the Bacteriophage P4 Integrase Family, Is Responsible for Chromosomal Insertion of the 105-Kilobase *clc* Element of *Pseudomonas* sp. Strain B13," *Journal of Bacteriology 180*: 5505-5514.

Reed et al., "Carbohydrate Accumulation and Osmotic Stress in Cyanobacteria," *J. Gen. Microbiology 130*: 1-4 (1984).

Reichel et al., "Enhanced Green Fluorescence by the Expression of an *Aequorea victoria* Green Fluorescent Protein Mutant in Mono- and Dicotyledonous Plant Cells," *Proc. Nat. Acad. Sci. USA 93*: 5888-5893 (1996).

Reinhold-Hurek et al., "Self-splicing Introns in tRNA Genes of Widely Divergent Bacteria," *Nature 357*: 173-176 (1990).

Rensburg et al., "Proline Accumulation as Drought-tolerance Selection Criterion: Its Relationship to Membrane Integrity and Chloroplast Ultrastructure in *Nicotiana tabacum* L.," *J. Plant Physiol. 141*: 188-194 (1993).

Richards et al., "The Centomere Region of *Arabidopsis thaliana* Chromosome 1 Contains Telomere-Similar Sequences," *Nucleic Acids Research 19*: 3351-3357 (1991).

Richards et al., "Isolation of a Higher Eukaryotic Telomere from *Arabidopsis thaliana*," *Cell 53*: 127-136 (1988).

Richards et al., "Plant Centromeres: Structure And Control," *Curr Opin Plant Biol.1*: 130-135 (1998).

Rieder, "The Formation, Structure, and Composition of the Mammalian Kinetochore and Kinetochore Fiber," New York State Department of Health, Division of Laboratories and Research, *Intl. Rev. Cytol.79*: 1-58 (1982).

Rogers et al., "Improved Vectors for Plant Transformation: Expression Cassette Vectors and New Selectable Markers," *Methods in Enzymology 153*: 253-277.

Rosenberg et al., "RFLP Subtraction": A Method for Making Libraries of Polymorphic Markers, *Proc. Natl. Acad. Sci. USA 91*: 6113-6117 (1994).

Rosenfeld, "Human artificial chromosomes get real," *Nature Genetics 15*: 333-335 (1997).

Round et al., "*Arabidopsis thaliana* Centromere Regions: Genetic Map Positions and Repetitive DNA Structure," *Genome Research 7*: 1045-1053 (1997).

Sasnauskas et al., "Molecular Cloning and Analysis of Autonomous Replicating Sequence of *Candida maltosa*," *Yeast* 8: 253-259 (1992).

Sauer, "Functional Expression of the *cre-lox* Site-Specific Recombination System in the Yeast *Saccharomyces cerevisiae*," *Molecular and Cellular Biology* 7: 2087-2096 (1987).

Schmidt et al., "Analysis of Clones Carrying Repeated DNA Sequences in Two YAC Libraries of *Arabidopsis thaliana* DNA," *The Plant Journal* 5: 735-744 (1994).

Schmidt et al., "Physical Map and Organization of *Arabidopsis thaliana* Chromosome 4," *Science*, 270: 480-483 (1995).

Schwartz et al., "New Techniques for Purifying Large DNAs and Studying Their Properties and Packaging," Department of Human Genetics and Development, Columbia University: 189-195.

Schwartz et al., "New Techniques for Purifying Large DNAs and Studying Their Properties and Packaging ," *Symp. Quant. Biol.* 47: 195-198 Cold Spring Harbor (1982).

Schweizer et al., "Species-specific sequences for identification of somatic hybrids between *Lycopersicon esculentim* and *Solanum acaule*," *Theor. Appl. Genet* 75: 679-684 (1988).

Sears et al., "Cytogenic Studies in *Arabidopsis thaliana*," Department of Genetics, University of Missouri, *Can. J. Genet. Cytol.* 12: 217-223 (1970).

Shagan et al., "Nucleotide Sequence of an *Arabidopsis thaliana* Turgor-Responsive cDNA Clone Encoding TMP-A, a Transmembrane Protein Containing the Major Intrinsic Protein Motif," *Plant Physiol.* 101: 1397-1398 (1993).

Sheen et al., "Green-flourescent Protein as a New Vital Marker in Plant Cells," *The Plant Journal* 8: 777-784 (1985).

Simoens et a.l, "Characterization of Highly Repetitive Sequences of *Arabidopsis thaliana*," *Nucleic Acids Research* 16: 6753-6766 (1988).

Singh et al., "Centromere Mapping and Orientation of the Molecular Linkage Mao of Rice (*Oryza Sativa L.*)," *Proc Natl Acad Sci USA*. 93: 6163-6168 (1996).

Smith et al., "Expression of Truncated Tomato Polygalacturonase Gene Inhibits Expression of the Endogenous Gene in Transgenic Plants," *Mol. Gen. Genet.* 224: 447-481 (1990).

Smithies et al., "Insertion of DNA Sequences into the Human Chromosomal—Globin Locus by Homologous Recombination," *Nature* 317: 230-234 (1985).

Smyth, "New *Arabidopsis* Mutations that Result in All Four Products of Meiosis Being Held Together as a Tetrad of Fused Pollen Grains May Facilitate Genetic Mapping and Lead to New Insights into Pollen Biology," *Current Biology* 4: 851-853 (1994).

Somerville et al., "Plant Functional Genomics," *Science* 285: 380-383 (1999).

Spielmann et al., "T-DNA Structure in Transgenic Tobacco Plants with Multiple Independent Integration Sites," *Mol. Gen. Genet.* 205: 34-43 (1986).

Stalker et al., "Herbicide Resistance in Transgenic Plants Expressing a Bacterial Detoxification Gene," *Science* 242: 419-423 (1988).

Steifel et al., Herbicide Resistance in Transgenic Plants Expressing a Bacterial Detoxification Gene,: *Nature* 341: 343 (1989).

Stinchomb et al., "Isolation and Characterisation of a Yeast Chromosomal Replicator," *Nature* 282: 39-43 (1979).

Stougaard, "Substrate-Dependent Negative Selection in Plants.Using a Bacterial Cytosine Deaminase Gene," *The Plant Journal* 3: 755-761 (1993).

Sullivan et al., "Isolation and Characterization of a Maize Chlorophyll a/b Binding protein Gene that Produces High Levels of mRNA in the Dark," *Mol. Gen. Genet.* 215: 431-440 (1980).

Sun et al., "Human Artificial Episomal Chromosomes for Cloning Large DNA Fragments in Human Cells," *Nature Genetics* 8: 33-41 (1994).

Sun et al., "Molecular Structure of a Functional Drosophila Centromere," *Cell* 91: 1007-1019 (1997).

Sutcliffe, "Nucleotide Sequence of the Ampicillin Resistance Gene of *Escherichia coli* Plasmid pBR322," *Proc. Natl Acad. Sci USA* 75: 3737-3741 (1978).

Symington et al., "Meiotic Recombination Within the Centromere of a Yeast Chromosome," *Cell* 52: 237-240 (1988).

Symons, "Avocado Sunblotch Viroid: Primary Sequence and Proposed Secondary Structure," *Nucleic Acids Research* 9: 6527-6537 (1981).

Symons, "Small Catalytic RNAs," *Annu. Rev. Biochem 61*: 641-671 (1992).

Tarczynski et al., "Expression of a Bacerial mtID Gene in Transgenic Tobacco Leads to Production and Accumulation of Mannitol," *Proc. Nat. Acad. Sci. USA* 89: 2600-2604 (1992).

Tarczynski et al., "Stress Protection of Transgenic Tobacco by Production of the Osmolyte Mannitol," *Science* 259: 508-510 (1993).

Tavoletti et al., "Half Tetrad Analysis in Alfalfa Using Multiple Restriction Fragment Length Polymorphism Markers," *Proc. Natl. Acad. Sci. Online* 93: 10918-10922 (1996).

Thillet et al., "Site-directed Mutagenesis of Mouse Dihydrofolate Reductase. Mutants with Increased Resistance to Methotrexate and Trimethoprim," *J. Biol. Chem* 263: 12500-12508 (1988).

Thomas et al., "High-Frequency Targeting of Genes to Specific Sites in the Mammalian Genome," *Cell* 44: 419-428 (1986).

Thomas et al., "Viable Molecular Hybrids of Bacteriophage Lambda and Eukaryotic DNA," *Proc. Nat. Acad. Sci. USA* 71: 4579 (1974).

Thompson et al., "Identification and Distribution of Seven Classes of Middle-Repetitive DNA in the *Arabidopsis thaliana* Genome," *Nucleic Acids Research* 24: 3017-3022 (1996).

Thompson et al., "Decreased Expression of BRCA1 Accelerates Growth and Is Often Present During Sporadic Breast Cancer Progression," *Nature Genet.* 9: 444-450 (1995).

Thompson et al., "A Novel Repetitive Sequence Associated with the Centrometric Regions of *Arabidopsis thaliana* Chromosomes," *Mol Gen Genet* 253: 247-252, (1996).

Tian et al., "Expression of the Green Fluorescent Protein Gene in Conifer Tissues," *Plant Cell Reports* 16: 267-271 (1997).

Tominaga, "The Site-specific Recombinase Encoded by pinD in *Shigella dysenteriae* is due to the presence of a defective Mu prophase," *Microbiol.* 143: 2057-2063 (1997).

Toriyama et al., "Haploid and Diploid Plant Regeneration from Protoplasts of Another Callus in Rice," *Theor Appl. Genet.* 73: 16-19 (1986).

Tsay et al., "Identification of a Mobile Endogenous Transposon in *Arabidopsis thaliana*," *Science* 260: 342-344 (1993).

Tugal et al., "*Arabidopsis* 22-Kilodalton Peroxisomal Membrane Protein, Nucleotide Sequence Analysis and Biochemical Characterization," *Plant Physiology* 120: 309-320 (1999).

Twell et al., "Promoter Analysis of Genes that Are Coordinately Expressed During Pollen-Specific Enhancer Sequences and Shared Regulatory Elements," *Genes Dev.* 5: 496-507 (1991).

Twell et al., "Transient Expression of Chimeric Genes Delivered Pollen by Microprojectile Bombardment," *Plant Physiol.* 91: 1270-1274 (1989).

Tyler-Smith et al., "Localization of DNA Sequences Required for Human Centromere Function Through an Analysis of Rearranged Y Chromosomes," *Nature Genetics* 5: 368-375 (1993).

Tyler-Smith et al., "Mammalian Chromosome Structure," *Current Opin. Genetic Dev.* 3: 390-397 (1993).

Uchimiya et al., "Expression of a Foreign Gene in Callus Derived from DNA-treated Protoplasts of Rice," *Mol. Gen. Genet.* 204: 204 (1986).

Vahedian et al., "Genomic Organization and Evolution of the Soybean SB92 Satellite Sequence," *Plant Molecular Biology* 29: 857-862 (1995).

Valvekens et al., "*Agrobacterium tumefaciens*-Mediated Transformation of *Arabidopsis thaliana* Root Explants by Using Kanamycin Selection," *Proc. Natl. Acad. Sci. USA* 85: 5536-5540 (1988).

Van der Krol et al., "Flavonoid Genes in Petunia: Addition of a Limited Number of Gene Copies May Lead to a Suppression of Gene Expression," *Plant Cell* 2: 291-299 (1990).

Van't Hof et al., "The Size and Number of Replicon Families of Chromosomal DNA of *Arabidopsis thaliana*," *Chromosoma* 68: 269-285 (1978).

Vasil et al., "Herbicide Resistant Fertile Transgenic Wheat Plants Obtained by Microprojectile Bombardment of Regenerable Embryogenic Callus," *BioTechnology* 10: 667-674 (1992).

Vasil, "Progress in the Regeneration and Genetic Manipulation of Cereal Crops," *BioTechnology 6*: 397-402 (1988).

Vernon et al., "A Novel Methyl Transferase Induced by Osmotic Stress in the Faculative Halophyte *Mesembryanthemum crystallinum*," *The EMBO Journal 11*: 2077-2085 (1992).

Voytas et al., "A Copia-Like Transposable Element Family in *Arabidopsis thaliana*," *Nature 336*: 242-244 (1988).

Wagner et al., "Coupling of Adenovirus to Transferrin-Polylysine/DNA Complexes Greatly Enhances Receptor-Mediated Gene Delivery and Expression of Transfected Genes," *Proc. Natl. Acad. Sci. USA*, 89: 6099-6103(1992).

Walker et al., "DNA Sequences Required for Anaerobic Expression of the Maize Alcohol Dehydrogenase 1 Gene," *Proc. Nat. Acad. Sci. USA 84*: 6624-6628 (1987).

Wang et al., "Characterization of cis-Acting Elements Regulating Transcription from the Promoter of a Constitutively Active Rice Actin Gene," *Molecular and Cellular Biology*: 3399-3406 (1992).

Wang et al., "Structural Analysis and Complete Physical Map of *Arabidopsis thaliana* Chromosome 5 Including Centromeric and Telomeric Regions," *DNA Res. 6*: 381-386 (1999).

Weide et al., "Paracentromeric Sequences on Tomato Chromosome 6 Show Homology to Human Satellite III and to the Mammalian CENP-B Binding Box," *Mol. Gen. Genet. 259*: 190-197 (1998).

Wensink et al., A System for Mapping DNA Sequences in the Chromosomes of *Drosophila melanogaster*: , *Cell 3*: 315-325 (1974).

Westhof, Michel., Modeling of the Three-dimensional Architecture of Group I Catalytic Introns Based on Comparative Sequence Analysis,: *J. Mol. Biol. 216*: 585-610 (1990).

Wevrick et al. "Partial Deletion of Alpha Satellite DNA Associated with Reduced Amounts of the Centromere Protein CENP-B in a Mitotically Stable Human Chromosome Rearrangement," *Molecular and Cellular Biology 102*: 6374-6380 (1990).

Whitehouse et al., "Mapping Chromosome Centromeres by the Analysis of Unordered Tetrads," *Nature 4205*: 893 (1950).

Wigler et al., "Transfer of Purified Herpes Virus Thymidine Kinase Gene to Cultured Mouse Cells," *Cell 1 1*: 223-232 (1977).

Willard, "Centromeres of mammalian chromosomes," *TIG 6*(12): 410-416 (1990).

Willard, "Centromeres: The Missing Link in the Development of Human Artificial Chromosomes," *Genetics & Development 8*: 219-225 (1998).

Wolter et al., "Chilling Sensitivity of *Arabidopsis thaliana* with Genetically Engineered Membrane Lipids," *The EMBO Journal 1 1*: 4685-4692 (1992).

Wong et al., "Electric Field Mediated Gene Transfer," *Biochim. Biophys. Res. Commun. 107*: 584-587 (1982).

Wright et al., "Multiple Non-LTR Retrotransposons in the Genome of *Arabidopsis thaliana*," *Genetics 142*: 569-578 (1996).

Wu et al., "Composition and Structure of the Centromeric Region of Rice Chromosome 8," *Plant Cell 16*: 967-76 (2004).

Xia et al., "Genomic Organization of the *canrep* Repetitive DNA in *Brassica juncea*," *Plant Molecular Biology 26*: 817-832 (1994).

Xia et al., Structure and Evolution of a Highly Repetitive DNA Sequence from *Brassica napus*, *Plant Molecular Biology 21*: 213-224 (1993).

Xiang, et al. "The Anti-*nptII* Gene," *Plant Phy*siol. 102: 287-293 (1993).

Xu et al., "Expression of a Late Embryogenesis Abundant Protein Gene, HVA1, from Barley Confers Tolerance to Water Deficit and Salt Stress in Transgenic Rice," *Plant Physiol.* 110: 249-257 (1996).

Yamada et al., "Plant Regeneration from Protoplast-derived Callus of Rice," *Plant Cell Rep. 4*: 85 (1986).

Yamaguchi-Shinozaki et al., "Molecular Cloning and Characterization of 9 cDNAs for Genes that Are Responsive to a Desiccation in *Arabidopsis thaliana*: Sequence Analysis of One cDNA Clone that Encodes a Putative Transmembrane Channel Protein," *Plant Cell Physiol. 33*: 217-224 (1992).

Yang et al., "Maize Sucrose Synthase-1 Promoter Directs Phloem Cell-specific Expression of Gus Gene in Transgenic Tobacco Plants," *Proc. Natl. Acad. Sci. USA 87*: 4144-4148 (1990).

Yen et al., "CENP-E, a Novel Human Centomere-Associated Protein Required for Progression from Metaphase to Anaphase," *The EMBO Journal 10*: 1245-1254 (1991).

Young et al., "Organization of Coding Sequences in *Drosophila melanogaster*," *J. Supramolecular Struct., SI*: 211 (1977).

Young et al., Eukaryotic Genetic Systems ICNUCLA Symposia on Molecular and Cellular Biology VII: 315-331 (1977).

Yuan et al., "Selection of Guide Sequences That Direct Efficient Cleavage of mRNA by Human Ribonuclease P," *Science 263*: 1269-1273 (1994).

Yuan et al., "Targeted cleavage of mRNA by human RNase P," *Proc. Natl. Acad. Sci. USA 89*: 8006-8010 (1992).

Zatloukal et al., "Transferinfection: A Highly Efficient Way to Express Gene Constructs in Eukaryotic Cells," *Ann. N.Y. Acad. Sci. 660*: 136-153.

Zentgraf, "Telomere-binding Proteins of *Arabidopsis thaliana*," *Plant Molecular Biology 27*: 467-475 (1995).

Zhang et al., "Molecular Cloning, Nucleotide Sequence, and Function of a Site-Specific Recombinase Encoded in the Major 'Pathogenicity Island' of *Salmonella typhi*," *Gene 202*: 139-146 (1997).

Zhang et al., "*Zea mays* B Chromosome Centromere Repeat Sequence Zea_mays_MBsC216 pMBsC216," (unpublished).

Zukowski et al., "Chromogenic Identification of Genetic Regulatory Signals in *Bacillus subtilis* Based on Expression of a Cloned *Pseudomonas* Gene," *Proc. Natl. Acad. Sci.*, USA 80: 1101-1105.

\* cited by examiner

AGCTTGATTTGGATACATAAAGTGGTGGAGAATCACCAGGAAGT
TGAATAAATCTCATAGGAGTTGGCATGAAGAAGTTATCCCACTT
TCAAATCAGGTGATTCCAGTTCCCAGTTTGGGAATAGCACAGC
TTCTTCGTCGTTCCAATCAAACCAGGATGAATCWCTTTGTRARA
AGCT

FIG. 1A

AGCTTGATTTTGATACATAAAGTAGTGGAGAATCAYTWGGAAGT
GGAATAAATCTCATAGGAGTTAGGATGAAGAAGCTATCMCACTT
TCAAATCAGGTGATCCCARTTTCCTGTTTGGAATATGACAAC
TTMTTTGTCATTCTAATCAAACCAGGAWGAATCGCBATGTAARA
AGCT

FIG. 1B

```
Chrbo1    AGCTTGATTTCGATACATAAAGTGTGGAGAATCACCAGGAAGTTGAATAAATCTCATAG
ChrBo2    AGCTTGATTTTGATACATAAAGTAGTGGAGAATCAYTWGGAAGTGGAATAAATCTCATAG
position  1........10........20........30........40........50........60

Chrbo1    GAGTTGGCATGAAGAAGTTATCCCACTTTCAAATCAGGTGATTCCAGTTTCCAGTTTGG
ChrBo2    GAGTTAGCATGAAGAAGCTATCMCACTTTCAAATCAGGTGATCCCARTTTCTGTTTGG
position  61........70........80........90.......100.......110.......120

Chrbo1    GAATAGCACACCTTCTTCGTTCCAATCAAACCAGGATGAATCWCTTTGTRARAAGCT
ChrBo2    GAATATGACAACTTMTTGTCATTCTAATCAAACCAGGAMGAATCGCBATGTAARAAGCT
position  121.......130.......140.......150.......160.......170.......180
```

AGCTTGATTTGGATACATAAAGTGGTGGAGAATCACCAGGAAGT
TGAATAAATCTCATAGGAGTTGGSATGAAGAAGTTATCCCACTT
TCAAATCAGGTGATTCCCAGTTTCCCAGTTTGGAATAGCACAGC
TTCTTCGTCGTTCCAATCAAACCAGGATGAATCACTTTGTRAGA
AGCT

FIG. 1E

AGCTTGATTTGATACATAAAGTARTGGAGAATCAYYAGGAAGT
KGAATAAATCTCATAGGAGTTAGGATGAAGAAGCTATCCCACTT
TCAAATCAGGTGATCCCCARTTTCCTGTTTGGAATAKGACACARC
TTCTTTGTCATTCTAATCAAACCAGGAWGAATCGCKATGTAARA
AGCT

```
ChrBo1     AGCTTGATTTGGATACATAAAGTGGTGGAGAATCACCAGGAAGTTGAATAAATCTCATAG
ChrBo2     AGCTTGATTTTGATACATAAAGTTGGAGAATCAYYAGGAAGTKGAATAAATCTCATAG
position   1.........10........20........30........40........50........60

ChrBo1     GAGTTGGSATGAAGAAGTTATCCCACTTTCAAATCAGGTGATTCCAGTTTCCAGTTTGG
ChrBo2     GAGTTAGGATGAAGAAGCTATCCCACTTTCAAATCAGGTGATCCCARTTTCCTGTTTGG
position   ........70........80........90........100.......110.......120

ChrBo1     GAATAGGACACAGCTTCTTCGTCGTTCCAATCAAACCAGGATGAATCACTTGTRAGAAGCT
ChrBo2     GAATAKGACARCTTCTTTGTCATTCTAATCAAACCAGGAWGAATCGCKATGTAARAAGCT
position   .......130.......140.......150.......160.......170.......180
```

FIG. 1F

AAATTCAAATGGTCATAACTTTTMACWCGGAKGTCCGATTCAGG
CGCATAATATATCGAGACGCTCGAATTGAACAAYGGAAGCTCT
CGAG

FIG. 2A

AAATTCAAACGACAATAACTTTTTACTCGGATGTCYCGATTGAGT
CCCGTAATATATCGAGACGCTCGAAATTGAATRYTGAAGCTCTG
AGC

FIG. 2B

```
ChrGm1     AAATTCAAATGGTCATAACTTTTMACWCGGAKGTCCGATTCAGGCGCATAATATATCGAG
ChrGm2     AAATTCAAACGACAATAACTTTTACTCGGATCYGATTGAGTCCGTAATATATCGAG
position   1........10........20........30........40........50........60

ChrGm1     ACGCTCGAAATTGAACAAYGGAAGCTCTCGAG 92
ChrGm2     ACGCTCGAAATTGAATRYT-GAAGCTCT-GAGC 91
position   ........70........80........90...
```

FIG. 2C

AAATTCAAATGGTCATAACTTTTMACWCGGAKGTCCGATTCAGG
CGCATAATATATCGAGACGCTCGAAATTGAACAAYGGAAGCTCT
CGAG

FIG. 2D

AAATTCAAACGACAATAACTTTTTACTCGGATGTCYGATTGAGT
CCCGTAATATATCGAGACGCTCGAAATTGAATRYTGAAGCTCTG
AGC

FIG. 2E

```
ChrGm1     AAATTCAAAYGKCATAAYTTTTMACWCGGAKGTCCGATTCAGGCGCATAATATATCGAG
ChrGm2     AAATTCAAAGACAATAACTTTTTACTCGGATGTCYGATTGAGTCCCGTAATATATCGAG
position   1........10........20........30........40........50........60
```

```
ChrGm1     ACGCTCGAAATTGAACAAYGGAAGCTCTCGAG 92
ChrGm2     ACGCTCGAAATTGAAATRYT-GAAGCTCT-GAGC 91
position   ........70........80........90...
```

FIG. 2F

CCATCACGGGTTTTCTGGGCCCRTTTTGGAAGGTCAAACGAGCCCC
GGAGCGAGCATACGCCCTCATTTGACGATTTTCGTGTGCTATTG
CACACCATTTTTTGGGTGATCGGGATTCCGACGTCAAAAATGCC
AAATTTGTTCGTGGACGTCCGTCAAGACGTTGTCTATGCATACG
GTTGG

FIG. 3A

CCATCACGGGTTTTCTGGGCCCRTTTTGGAAGGTCAAACGAGCCCC
GRAGCGAGCATACGCCCTCATTTGACGATTTTCGTGTGCTATTG
CACACCATTTTTTGGGTGATCGGATTCCGACGTCAAAAATGCC
AAATTTGTTCGTGGACGTCCGTCAAGACGTTGTCTATGCATACG
GTTGG

FIG. 3B

GGCCACACAACCCCCATTTTTGTCGAAAATAGCCATGAACGACC
ATTTCAATAATACYRAAGGCTAACACCTACGGATTTTTRACCA
AGAAATGGTCTCCACCAGAAATCCAAGAATGTGATCTATGGCAA
GGAAACATATGTGGGGTGAGGTGTAYGAGCCTCTGGTCGAYGAT
CAAT

FIG. 4A

GGCCACACAACCCCCATTTTTGTCGAAAATAGCCATGAAYGACC
ATTTCAATAATACCGAAGGCTAACACCTACGGATTTTGACCA
AGAAATGGTCTCCACCAGAAATCCAAGAATGTGATCTATGGCAA
GGAAACATATGTGGGGTGAGGTGTAYGAGCCTCTGGTCGATGAT
CAAT

FIG. 4B

GGTTCCGGTGGCAAAAACTCGTAGCTTTGTATGCACCCMGACAC
CCGTTTTCGGAATGGGTGACGTGYGACAACAGAAATTGCGMGAA
ACCACCCCAAACATGAGTTTTGKACCTAAAGTAGTGGATTGGGC
ATGTTCGTTGYGAAAAACGAAGAAAT

FIG. 4C

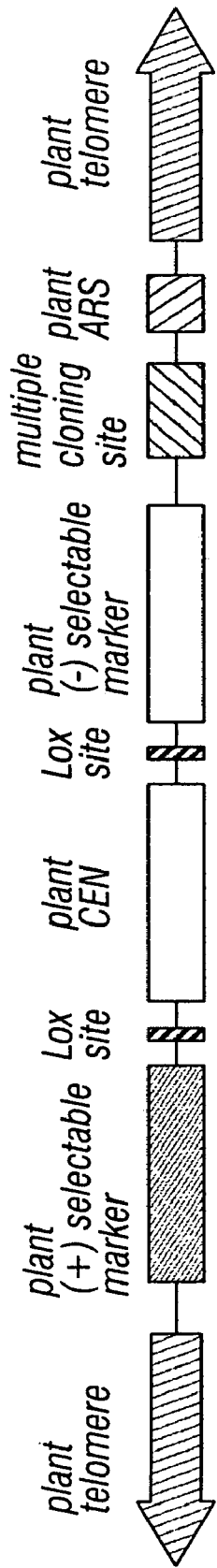
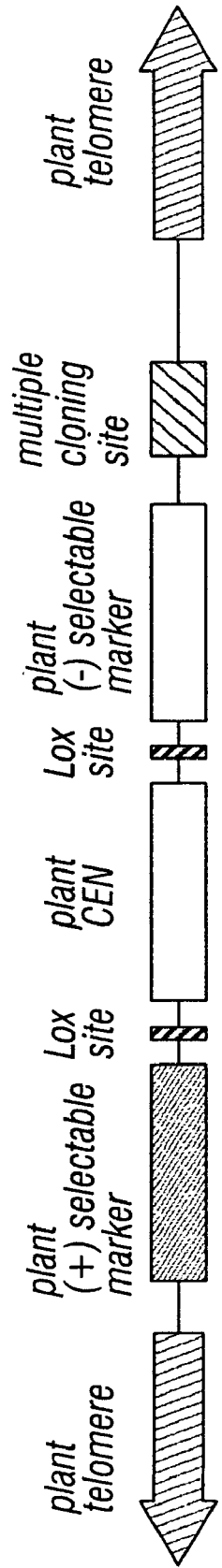
FIG. 7G
FIG. 7H

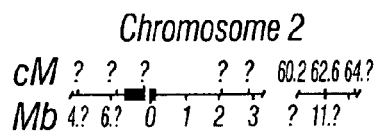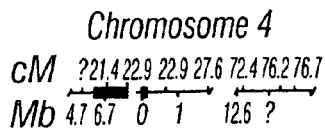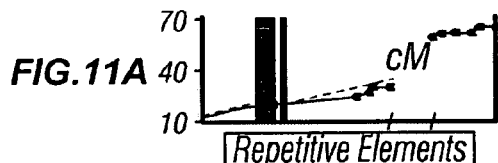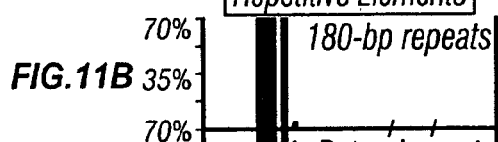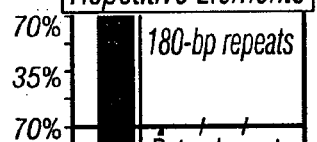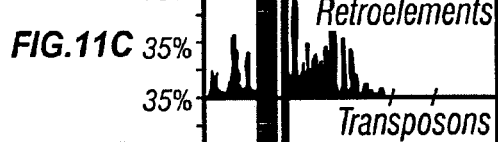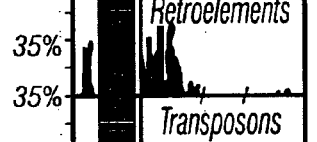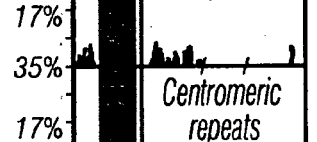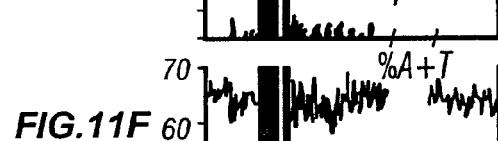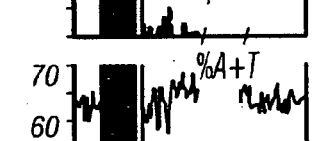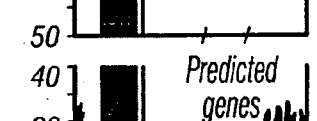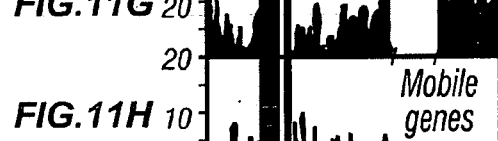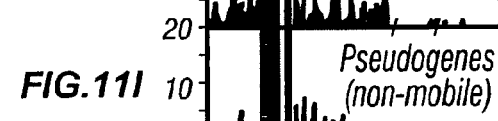

| Sequenced Clone | Marker name | Marker or Primer pair | Marker Location | marker properties, position |
|---|---|---|---|---|
| T13E11 | T13E11.01 | primer | 1755-2385 | Lan & Col |
| T13E11 | T13E11.30 | primer | 30628-31270 | Lan & Col |
| T13E11 | T13E11.48 | primer | 48187-48969 | Lan & Col |
| T13E11 | T13E11.63 | primer | 63886-64530 | Lan & Col |
| T13E11 | T13E11.78 | primer | 78190-78878 | Lan & Col |
| T13E11 | T13E11.93 | primer | 93907-94579 | Lan & Col |
| F27C21 | F27C21.18 | primer | 183383-190057 | Lan & Col |
| F27C21 | F27C21.02 | primer | 2570-3293 | Lan & Col |
| F9A16 | F9A16.71 | primer | 71978-72592 | Lan & Col |
| F9A16 | F9A16.53 | primer | 53253-53921 | Dom |
| F9A16 | F9A16.38 | primer | 37116-37733 | Dom |
| F9A16 | F9A16.22 | primer | 22166-22889 | Dom |
| F9A16 | F9A16.03 | primer | 3308-4091 | Lan & Col |
| T5M2 | mito border | marker | 17685 | Dom |
| T5E7 | T5E7.23 | primer | 109092-109688 | Lan & Col |
| T5E7 | T5E7.73 | primer | 73460-74120 | Lan & Col |
| T5E7 | T5E7.58 | primer | 57942-58583 | Lan & Col |
| T5E7 | T5E7.40 | primer | 40913-41537 | Lan & Col |
| T5E7 | mito border | marker | 13507 | Dom |
| T5E7 | T5E7.02 | primer | 2919-3585 | Lan & Col |

FIG. 14A-1A

| Forward Primer | Reverse Primer |
|---|---|
| AGCGCTGGGATGGGTTGGTTG | TTAATGCGGCAATGGCTGAACAAG |
| CAGGTTGCGGTTACTACATGGGTTTCAG | TATGCATGCGAGTTGGTGGAGGTAAAG |
| AACCCCCGTAAATTAAACCACAC | CGATACGGGCATGACTCCAG |
| ACGGCGGTTGAGAGGAGAAGC | CCCCAAACGCAGCAAGACAATC |
| AACAAAACAAATGCCAGGTCAGG | CTCCGGTCGCAAAGTTACATACAG |
| GTTACCCCGTCCTGAGATTGAG | TGGGGAGCAGGATTTGATGTG |
| CAGGCGATTGTCTTTTATAGGCTGTAAG | TTTTGCTGGAACGGAGGGAGTAC |
| ACAAAAGCCGAACTCGTGGAAG | TGCCTGGTTGATTATTGCTGAAAG |
| AATGCTTTTGCGACTCTTGTTTG | TTGTTATTTGGGTTTTGGGTTGG |
| CGCAGGCGGCTACTTGTTTG | GATGAATTGATCCGTTGTTTATGTCT |
| CAAGGCGGGAAAACAACTC | AATTATTTCAACGGCTCTTTACC |
| GTATTTAGCATTATGTTAGTCTGTTAGTGG | GCTCCTTGCGTATTCTTCACC |
| GATCCAGCAACCTTAGCCCTCCTTC | GATCCCTCAGTTCGAAATCAATCTTC |
| AAGGCATCAACGTTTGTGTG | CTACCAGGTAGGTGAAACG |
| ATTATTGGCTGCTGCACTTCTGTCAC | AGGGCCGGAGCTCGTATGGA |
| TCTCGGAGTAGGGCTTTGTTCTG | CGGTCGCCCTCGTTCTGTATCTG |
| AGGGGCTTACAAGAATGAAC | TCGCCAATGAAAGAGGGTAG |
| GTAGCCGGCTCAGTCTCATAACATC | CTAAATCCCGAAAACCCAAACCAC |
| CGAATTCCTTCAGATGATGC | TTGCCTTACCTATACCCGAC |
| AAATGGCAGAAGCAGAAGCAGGAATAG | TAATGCAAGGGTCTCGTAATGGAAATG |

FIG. 14A-2A

| | | | | |
|---|---|---|---|---|
| T12J2 | T12J2.01 | primer | 1373-1998 | Lan & Col |
| T12J2 | T12J2.19 | primer | 19369-20038 | Lan & Col |
| T12J2 | T12J2.37 | primer | 37750-38359 | Lan & Col |
| T12J2 | ATEDA59 | marker | 50592 | Lan & Col |
| T12J2 | T12J2.56 | primer | 56455-57533 | Lan & Col |
| T12J2 | T12J2.73 | primer | 73911-74556 | Lan & Col |
| T14C8 | T14C8.1 | primer | 8862-9544 | Lan & Col |
| T14C8 | T14C8.6 | primer | 10837-11485 | Lan & Col |
| T14C8 | T14C8.7 | primer | 45334-46016 | Lan & Col |
| T14C8 | T14C8.3 | primer | 46672-47283 | Lan & Col |
| T14C8 | T14C8.8 | primer | 48833-49538 | Lan & Col |
| T14C8 | T14C8.9 | primer | 71115-71878 | Lan & Col |
| T14C8 | T14C8.5 | primer | 73841-74456 | Lan & Col |
| T14C8 | T14C8.4 | primer | 75442-76122 | Lan & Col |
| F7B19 | F7B19.1 | primer | 108-757 | Lan & Col |
| F7B19 | F7B19.12 | primer | 13831 | Lan & Col |
| F7B19 | F7B19.27 | primer | 27033 | Lan & Col |
| F7B19 | F7B19.2 | primer | 30189-30791 | Lan & Col |
| F7B19 | F7B19.43 | primer | 43142 | Lan & Col |
| F7B19 | F7B19.3 | primer | 55446-56209 | Lan & Col |
| F7B19 | F7B19.59 | primer | 59771 | Lan & Col |
| F7B19 | F7B19.4 | primer | 70859-71492 | Lan & Col |
| F7B19 | F7B19.77 | primer | 77633 | Lan & Col |
| F7B19 | F7B19.95 | primer | 95351 | Lan & Col |

FIG. 14A-1B

```
GTGTGGCCTCGTGTGACCTGAC        AGTTTGCTTCGTTGCTTGCTTATTATG
CTGGCCCATCCCTTATCGGTTTAC      AGCGCAATCAAGCTATCCCTACATA
ACCTCCCCCACACTTAAACGACACTG    CTCAGAATCCCAAAACAGAGCCACAC
TGAATGCTATGAAAGATGGATGAAAC    AGACGGCTAGTGATTGGTGG
AATCGGGCTCGGTTGTGTAGAAAC      ATGGCGCAATCAAAAGCAATCC
ACTTGTAGGCCCTTTGATGTTCTG      TGCTTTGTGTTGCTTTGATTATTCTATTAG
ACGAACCCGACGACCACTG           ACGCCTTTGATTCCATTTCTTACC
GACGGGTTGAAAGAAGCACAG         AGAAGATGATGGCAAGTTACGAAGAG
CGACCATTCACGACCCATAC          AAGCCCATTCAAAAGAGTTAGGAGAG
ATAGCGTCAGCCCTCATTTCAG        ACCTTTTGCTTGTATTTCGTG
CAAATGGGCGAGGGGG              TGTGCAAGTCATGGGTAAGGAG
GGTGCGGGAGAACGATGAC           CCGGTTTCTGCGATATTTGGTTAG
TTCCGCGCCCAAAAGGTG            AGAGTCAAGCCAAGCAATAACAGG
AAGAAGGCTGGAATTGGTTGAG        GAGCGGAAGTAGATGCAGAATGTC
AAGGTCCGGCGGTGGTGAG           GGGTCGAGTGATGTGATTGAGTG
TAACGTCATCAGCGGGTAGGAAAC      TTACAAGCGAGAAAAGATGAGAAGC
CCCCGCTGAACTGACTACGAG         TCCGCCCACCGATAAGATACGAC
GCTCGTTGCGGTTGCTGTTC          CCGCGGTTGGCTGCTTTTAG
CAGGGAAAGTGGTTGGATTGATG       TGCCTCTTCCGGAACTGGTG
ATTTGTTGCCCATCGTCCTTC         TTATCAATGTATTTCCCTGTGTATC
TTGAAGAATGCGCATAGCCGTAG       TCTGGGATGAAGAGAAAGAGAACTGTC
AAAAACCGTGAGAGACCCATAAATG     TCCAAATCGCGAAAGTGACAG
ATAACCGAAGAAGCCGAGAAATC       ATCCGGAGACGAAAATGAACTTAG
TCGATTGCCAGCAGAGTCAGAAC       TGGGGGCTTGTAAGGAGGAGTAAC
```

FIG. 14A-2B

| | | | | |
|---|---|---|---|---|
| F7B19 | F7B19.5 | primer | 98977-99658 | Dom? |
| F7B19 | F7B19.6 | primer | 112337-113039 | Lan & Col |
| T15D9 | T15D9.3 | primer | 2985 | Lan & Col |
| T15D9 | T15D9.1 | primer | 12299-12914 | Lan & Col |
| T15D9 | T15D9.19 | MARKER | 18991 | LAST RECOMBINANT Col |
| T15D9 | T15D9.2 | primer | 37103-37728 | Lan & Col |
| T15D9 | T15D9.3a | primer | 52189-52811 | Col |
| T15D9 | T15D9.55 | primer | 55134 | Lan & Col |
| T15D9 | T15D9.73 | primer | 72993 | Lan & Col |
| T15D9 | T15D9.4 | primer | 73930-74552 | Lan & Col |
| T15D9 | T15D9.5 | primer | 86724-87494 | Lan & Col |
| T15D9 | T15D9.93 | primer | 93763 | Lan & Col |
| F7K9 | F7K9.3 | primer | 21647-22276 | Lan & Col |
| F7K9 | F7K9.2 | primer | 12216-12843 | Lan & Col |
| F7K9 | F7K9.1 | primer | 3590-4226 | Lan & Col |
| F12P23 | F12P23.3 | primer | 61772-62430 | Lan & Col |
| F12P23 | F12P23.5 | primer | 44870-45511 | Lan & Col |
| F12P23 | F12P23.4 | primer | 40880-41507 | Lan & Col |
| F12P23 | F12P23.2 | primer | 22431-23107 | Lan & Col |
| F12P23 | F12P23.1 | primer | 3352-4026 | Lan & Col |
| T4D8 | T4D8.5 | primer | 81647-82250 | Lan & Col |
| T4D8 | T4D8.3 | primer | 47146-47883 | Lan & Col |
| T4D8 | T4D8.2 | primer | 21848-22453 | Lan & Col |
| T4D8 | T4D8.1 | primer | 18915-19589 | Lan & Col |

*FIG. 14A-1C*

```
AGATGGGGTGCTATTCTTGTATG        GCGGTCGAGTGATTGCTGTAG
AGGGCGAAACTTTGAGAGCAC          TATCGGGTTTTGAAGAGGAAGG
AGCGTCGGCGGTGTGGAG             TCCTGGCAAATTGTCTTCTCGTTG
GCTCCCGCCATCTCCTCGTC           GAAGTCCCATGCCTATCCCTG
GAGCCCTTCTATGAGCCTACCTGTTC     AGAGATCCCCTGTTACTAAAGCCTATTCTG
ATGGGGTAATCGAATAGTGTGGTC       CCCTAGGGCATCCGTTTTTATCTC
CGGAGAAAGTTGGGGGTTAGTTG        GAGAGGTTTGGGTTGGGCTTGTAG
GCTGCGAACCCACACTTTGCTC         ATGTTATCGTCGCCGCGTTTTATG
AACCGGTTGATAGTAGACGAGATG       TCCGGGGTTGCGATAGAG
GTAAGACGGAGCCCCTGAAG           AACATGTTAAAGCCAATACCCTCTC
TCGGAAAGGCTAGAGATGGGTAACTG     ATTGGACTATATGGGCCTCGTGAC
TTTGCGGATATTCTAAAGGTGATG       TACTATTGCGCTGCTGTGTTGAGG
GGATGCAATGCCCGTTATGATG         TCGAGGGAGGATGCTGAGTATG
CAAAGCGGCCATCTCCCTTC           GCAATTCATACCGCCACATCTG
ACTATGCGTGGGTGGCTTTGTG         CAGGGGCATGCGGAATCTC
AGCGAGGTTATCTATCAGGGTTG        GATTAGGTCCGCTTCTCTTCCAGTTAG
CTTCATTTGCATCATCGTTATTAG       GGTGTGAAGTCTGAGGCTCCC
TACCCATGCCTTGACTGCTG           TTCTGAACGTGTGTGTTCTATTTG
TCGTCGAACTAATTGGTGGGAAC        TCGGGAAGAGTGCCTAAGAG
ACAATGGCAACAATGGGCTGATAG       TTCGGGTCGTTGTTCCTAAAG
CTCGGTCTGGTAATGTGAAGTGGT       ATACGTCGCGGGAGTTGAG
GCCCGTCTGCCATCTCTATC           CGCCTCCTTCACAGCCACAA
AAACTCGCCGCCCTCGTGTAAC         AGGATAAACCCATAGCTTGACCAG
CTCGTCTCATCCAAATCCGTCC         CAATATAACCCCGTCCCGTGAAG
```

FIG. 14A-2C

| Sequenced Clone | Marker name | Marker or Primer pair | Marker Location | marker properties, position |
|---|---|---|---|---|
| T5H22 | T5H22.00 | primer | 248-2654 | Lan & Col SSLP |
| T5H22 | T5H22.21 | primer | 21508-22868 | Col Dom |
| T5H22 | T5H22.41.3 | primer | 35072-35719 | Lan & Col |
| T5H22 | T5H22.41.4 | primer | 64404-65591 | Col Dom |
| T5H22 | T5H22.65 | primer | 65036-66470 | Lan & Col |
| T7M24 | T7M24.04 | primer | 4816-8214 | Lan & Col |
| T7M24 | T7M24.46 | primer | 46240-47868 | Col Dom |
| T25H8 | T25H8.01 | primer | 1889-2953 | Lan & Col |
| T25H8 | T25H8.17 | primer | 16846-17990 | Col Dom |
| T25H8 | T25H8.22.9 | primer | 22482-25074 | Ler & Col |
| T24M8 | T24M8.65 | primer | 65402-66309 | Lan & Col |
| T24M8 | T24M8.54 | primer | 53857-54655 | Col Dom |
| T24M8 | T24M8.43 | primer | 42439-43274 | Lan & Col |
| T24M8 | T24M8.22 | primer | 22640-23386 | Lan & Col |
| T24M8 | T24M8.09 | primer | 5961-8374 | Lan & Col |
| T24H24 | T24H24.82 | primer | 82814-82890 | Lan & Col |
| T24H24 | T24H24.66 | primer | 66082-66765 | Ler & Col |
| T24H24 | T24H24.48 | primer | 47836-48636 | Ler & Col |
| T24H24 | T24H24.11 | primer | 11212-11867 | Ler & Col |
| T27D20 | T27D20.77 | primer | 77681-78420 | Lan & Col |

FIG. 14B-1A

| Forward Primer | Reverse Primer |
|---|---|
| TTTGTTACCCCTTTGGCTCGGACTGG | AAGGGGACACGCACAAAAACGCTCTC |
| GTCGCCCTTGGTCTAGTAAATGG | CTGTTCGTCGCCTTCTGCTG |
| TTGCGAGAAACTTGCGAGGAACATC | TTAGAAAAGCATCGGGCACCAAAC |
| CTCCCTCGCATATTTGTGACTG | GTTGCCAAAGTTCTCTACGATTC |
| TCAACCTAAGGCAAATTTCTAAG | TTTAATGAAGGCCCAACACC |
| GTGCATGGCCTAAACAACAG | GTTCTCATAACGGGTCAGTCC |
| ATGTTATGTTTACGTCGGGGTTGTGTTG | TCTCGGCTCCGGATGCTATTTGTATTTTC |
| TGACGAAGAAGGGGGAAAAGTTG | TGACGTGGTGAAAGTAGGCTGTGAAG |
| ACTAAAGCCCCAACTGAAGAGGAAG | AAACCGCCACTACCGCCATAA |
| AATCGATCCGTCTTTCACCAAC | CTTCCCTGCAGCCGTTCTTC |
| CGGCATGACCAAACCCTAAACTC | AGGGGAAAGATGAAAGATGAAATAAG |
| TAATAAACCGCTCAGCCACCACTCTAAG | GGGCTGCTCCAATCTCGCTACAC |
| CTTAAATTGCCCGTGATGATGGTTG | GATGGAGTCGGCAAAAGATAGGATG |
| ACGAGAAGCGAAAACCGAAGATAG | CGAACCTAAACCAAACCTAAACTGAATC |
| GAGTTCTGGGTAATTTCCTCTCG | ATTCTTGCGTGTCCCTGGTGTAAC |
| AGACAGCCGGAAGCAATGGTGG | TCTCGCTGCTGGACATACTCACTCAC |
| GTTGAAGGACCGGAGTTGTTAGAC | TGTGGATCGGTTATTGGAGGG |
| CCCCCAGCCCATTGAGTGAGTAG | AGCGGCGGCCTTGAGAGTATC |
| GGCGGCGTAGTTATGTGTTGATTGAG | TACCACGGCCCCGAGATACTAAC |
| TCGCGCAAATGGGACACG | CGGGGAGGCTCGGAATC |

*FIG. 14B-2A*

| | | | | |
|---|---|---|---|---|
| T27D20 | T27D20.64 | primer | 64198-66686 | Ler & Col |
| T27D20 | T27D20.51 | primer | 51084-51783 | Lan & Col |
| T27D20 | T27D20.41 | primer | 41203-42770 | Lan & Col |
| T27D20 | T27D20.06 | marker | 6107-6887 | Col Dom |
| T19B17 | T19B17.96 | primer | 96402-97060 | Lan & Col |
| T19B17 | T19B17.77 | primer | 77318-78093 | Lan & Col |
| T19B17 | T19.B17.59 | primer | 59092-59808 | Lan & Col |
| T19B17 | T19B17.44 | primer | 44057-44788 | Col Dom |
| T19B17 | T19B17.30 | primer | 30680-31352 | Lan & Col |
| T19B17 | T19B17.11 | primer | 11260-12044 | Lan & Col |
| T26N6 | T26N6.12 | primer | 12724-13462 | Lan & Col |
| T26B6 | T26N6.27 | primer | 27839-28536 | Lan & Col |
| T26B6 | T26N6.42 | primer | 43996-44639 | Col only |
| T26B6 | T26N6.59 | primer | 59333-59938 | Col only |
| T26B6 | T26N6.74 | primer | 74460-75083 | Lan & Col |
| T26B6 | T26N6.93 | primer | 93352-93986 | Lan & Col |
| F4H6 | F4H6.44 | primer | 42567-43173 | Lan & Col |
| F4H6 | F4H6.60 | primer | 60209-60835 | Lan & Col |
| F4H6 | F4H6.82 | primer | 82859-83642 | Lan & Col |
| F4H6 | F4H6.100 | primer | 100331-101001 | Lan & Col |
| T19J18 | T19J18.12 | primer | 12781-13435 | Lan & Col |
| Y19J18 | T19J18.27 | primer | 28093-29954 | Lan & Col |
| T4B21 | T19J18.71 | primer | 6380-7009 | Lan & Col |
| T4B21 | T19J18.42 | primer | 20045-20648 | Lan & Col |

*FIG. 14B -1B*

```
ACCTGCGATAGAGTTGTGAGTTC            CTGCCTTTGCCGATAATAGTC
CCGCCGGCTTATGCTGAG                 GAAGAGAAATGCCCTGTGAGTCC
GTGATTCGCAGGACATTGAGTG             TACATTTTGCAGCCATTTGTG
TCGAATGGCTGAAAGAAAAGAATAAGAG       AAAACGGGTGGGCGGAGAATG
CGTCTCCGTGAGGTGGC                  ATTTCATAATTATTTGGCGTGTGC
CGAACCCATCCGAACTAAC                TGCCACAACAAACTCCACTATG
AGCGGTCAATGTTCTTCAATGTCGTAG        TATCGCGGCGGAGTCAGGAG
CTGCCCCGACCACCTTTCAAC              TTGCGGATTCGTTATGCTGTTCTC
ATCGCCGCCGTCTTCTTCAG               CAGGTTCAGCCCGTTCAACTATAATC
TCATTTGCGTCTAGAGGTGGAGTGC          GGGGTAGAAAGAAGCGAGAGGGATAG
CACGGCATTCATCAAACGAG               GTAGGATCCGGCTGAATAGTGGTGG
TCTTCCGATGACGACAACGACAC            ATTCTGCTGCTGCTGATTCCTG
GACGGCCTTTTCATTTCTCACACAG          TTTCATATTTGCTCATCTAACCCCTTC
GCCTCGAACCCTACACCTCCAC             AGTCGCCGTAGCAAATGAAACC
ATGGGGCCCTTTGACTACTGAG             TCCGGAGACGATTTGATGAC
TTCCCCGCATGCATTAGTTCTTGTG          TTGCCATCATCTTTCTGTGTTGTCTATC
GCAGACGCGAGGACACAGACAG             CAGCCTAAGCCCATTTGTTTTGAAG
GTTCCAACGCTAGCAAGGTCTG             AGGGGCCAACATGCACTACAAG
ACAAATCAGAGGCCCAAAGTCAATG          TGGGCCGAATAACAGCAAGTCC
ATCCAAACGCCCAAATGTCAAC             TTAAGTGCGGTGCGGTTCAAATAC
ATGCCCATAAAGAAAGCCCGTC             CGCCTATCTTCGTGTCTCGTC
CAGCGCTGTACAGTGGTCAAATG            CGTGGGTCAGGTGGGTCAGG
CATTACTTACCCGCTTCCGTCTTTATC        AATGTTAGTGCGAGTTTATGGTTGTGTC
TGTCGCCTTACTCCATTCGTTCAAC          CGGCCGCCTTCATGTATCTATCTC
```

*FIG. 14B-2B*

| | | | | |
|---|---|---|---|---|
| T4B21 | T4B21.20 | primer | 21757-22522 | SSLP polymorphic |
| T4B21 | T4B21.35 | primer | 37346-38074 | Lan & Col |
| T4B21 | T19J18.57 | primer | 38498-39157 | Lan & Col |
| T4B21 | T4B21.52 | marker | 54320-55077 | Lan & Col |
| T4B21 | T4B21.68 | primer | 69927-70543 | Lan & Col |
| T4B21 | T4B21.83 | primer | 85772-86299 | Lan & Col |
| T1J1 | T1J1.08 | primer | 8862-9483 | Lan & Col |
| T1J1 | T1J1.23 | primer | 23155-23843 | Lan & Col |
| T1J1 | T15D16 | marker | 38027 | CAPS |
| T1J1 | T1J1.39 | primer | 39177-40174 | Lan & Col |
| T1J1 | T1J1.50 | primer | 50248-50937 | Lan & Col |
| T32N4 | T32N4.09 | primer | 10175-11108 | Lan & Col |
| T32N4 | T32N4.24 | primer | 24917-25724 | Lan & Col |
| T32N4 | T32N4.45 | primer | 45840-46451 | Lan & Col |
| T32N4 | T32N4.46 | primer | 46637-47558 | Col Dom |
| T32N4 | T32N4.60 | primer | 60777-61645 | Lan & col |
| T32N4 | T32N4.66 | primer | 66497-67374 | Col Dom |
| T1J24 | T1J24.114 | primer | 114825-115648 | Lan & Col |
| T1J24 | T1J24.90 | primer | 90665-91646 | Lan & Col |
| T1J24 | T1J24.81 | primer | 80921-81638 | Col Dom |
| T1J24 | T1J24.79 | primer | 79569-80351 | Lan & Col |
| T1J24 | T1J24.61 | primer | 60440-61245 | Lan & Col |
| T1J24 | T1J24.51 | primer | 51061-51798 | Lan & Col |
| T1J24 | T1J24.27 | primer | 27855-28895 | Lan & Col |

*FIG. 14B -1C*

```
AATAGGCTTTTCCGGTGCTTCTC      AATTGATTTTGGGGTTTCTCTGTTC
GTGAAAGGAGCAGCAGGAACAGTG     ATTTATAGGCCAATGACCCAATCG
CTATCAAACGCAGTCAAAGAAAGG     AGAAGGTGAGCCAAAGAGATTAGTG
ATAGACAAAATTGGCAACACATACC    CACGCCACTCTTCATCTCCTTTC
TTGTCATTGGCGCTGCTCTATC       GCTTTCCCACCAATATCCTTTC
AAGCCCGCGATTTGGTTC           CGCTACGCATGGGTCTATTTG
TAGAGCGGTAACTTAACGAATGTGC    ATGTGGGGCCAAATAAATCAAAAC
TGGAGGGCTTGCATGTGAGAGTG      CAGAGCCGGATGAGAAAACAGAGC
AATCAATTGGTTTCTACTTTTTAG     AACTCCGACTGAAGGTATAGC
ACCGGCTCATTGGCTAAAAAGTTC     TTAAGGGTTGGGGTTCATCTGTCAC
AAGTCTGGGAAGAGGATGAGAACCC    ATAAAGTACGCCGCCCATCAATAG
GGCAGATACGGCGGGTCCATAC       TCTGAATCGCATCTCCTCGTGTAAAG
CGTGGGAGCTGCCGTAGAAG         GCCGTTGATGATGAAAATAGGGTG
CGCCCCTTCAGGTTAGTC           GTTTGCTCCCCTCCCAGTG
CTGGCGTACGAGAGTGCTTGTG       ATGACCCTGTGCTTTTGCTCCTC
CTCTCGGCGTTGCTTCTGG          GCCCGGCTGGTGCTATTC
AAAGAAGCGAAACAACATAACCATAG   GGAGACAAAGAAATCGGCAGAGTAG
CATGCCCGAATTACGACACCTC       GCGCCAAATCTCTAAACAACACTC
AATGAATGGGACGAAAACGAAACT     GCATCCCCGGTACTGGTGAG
AATCGCGACTTTGCCTTCC          TAAACTACTATCCCACCACCACTACC
GTGTATCGGGGCCATCTCAG         GCTCAACATGCCGCAATCT
CCCAAAGTATAAGCGCCCACCTA      TAAGCGCCTCACTTCACCATTG
TCCGGAAGGAGCCACATAAG         TCCCCAGACCTCTCGTTGAC
GGCCGGGAGTTGGTCATAAGG        TCAATTTCAATCCCCGCTGGTC
```

*FIG. 14B -2C*

| | | | | |
|---|---|---|---|---|
| T1J24 | T1J24.23 | primer | 23943-24800 | Lan & Col |
| T1J24 | T1H24.01 | primer | 683-1663 | Lan & Col |
| | | | unknown-unique seq | |
| F6H8 | F6H8.70 | primer | unknown | Lan & Col- |
| F6H8 | F6H8.51 | primer | unknown | Lan & Col- |
| F6H8 | F6H8.94 | primer | unknown | Lan & Col- |
| F6H8 | F6H8.114 | primer | unknown | Lan & Col- |
| F2112 | F2112.82 | primer | 82463-83233 | Lan & Col |
| F2112 | F2112.70 | primer | 70415-71220 | Lan & Col |
| F2112 | F2112.68 | primer | 68874-69938 | Lan & Col |
| F2112 | F2112.50 | primer | 50288-50891 | Lan & Col |
| F2112 | F2112.48 | primer | 48960-50345 | Col |
| F2112 | F2112.29 | primer | 29895-30702 | Lan & Col |
| F2112 | F2112.02 | primer | 2313-3098 | Lan & Col |
| F14G16 | F14G16.100 | primer | 3496-4174 | Lan & Col |
| F14G16 | F14G16.81 | primer | 22905-23604 | Lan & Col |
| F14G16 | F14G16.66 | primer | 37689-38299 | Lan & Col |
| F14G16 | F14G16.49 | primer | 54150-54777 | Lan & Col |
| F14G16 | F14G16.32 | primer | 8172-8825 | Lan & Col |
| F14G16 | F14G16.66 | primer | 9445-10055 | Lan & Col |
| F14G16 | F14G16.16 | primer | 24251-24873 | Lan & Col |
| F14G16 | F14G16.01 | primer | 39801-40577 | Lan & Col |
| F28D6 | F28D6.42 | primer | 42565-43225 | Lan & Col |
| F28D6 | F28D6.50k | MARKER | 50323 | Col Dom |

FIG. 14B-1D

```
TGGTCCGGGCATATTGTTTTCTTGTG      CGGCGCTGTCCCTGGTTCC
TTCCCCAAAAATCGTTCAGC            ACATCGCCTCTTCAACCCACTC
ACCCGAGAAGCCGATGACC             AAATTTGGGGAGTTTGATAAGTGTG
GCTAAGCCATCCAAGTTCTGAG          GTTTGAGTCTTTGGCTTTGTATGTTC
CGTGCAGGGGAGTGTCGTG             CAATTTCAATCCCCGCTGGTC
CGCGGCTGCCTTCATGTATCTATC        GCCCATTTGTCGCCTTATTCTATTC
TTTTTGGGGATAGGGATTGAGTGTG       TAAGCGGAAGGAGAGGTTTGAAGTTG
TGCTGGCCTTTGTCATCTATTTGTC       CCGCGGGGACTGCCTACTC
CCAGAGCCGGGAAAGCAATAC           TAGCCGGGGTGGTCTCGTCG
TGACTATAGGGCGGTTGTGGTAAG        TTGGCTTGGAGTTTGCGTCGTC
ACCTTTCTCCTCAACGCACCTCACC       AACCCCTTGGCATATAACTCCGACTC
GTGGGGTCGAGTGGTGTGGTAG          GGATCCCCTGTTACTTAAGCCTATTC
AAAATCCCTCCCGCGTCAACATC         CATCATCCAATCCCAAATACAAGTC
AAACTTTCGCCACTCTCCCTATTATG      ATTTGCGTAAGGCGTTGATGACTC
CGTCTTCATCGGCTTCGTTCAG          TGGGGAGCGGAGGATTCTTG
AGCGATTGTACCCCACCATTC           GCTCCGGCAATCTTCTTCCTCTC
ACTTTGGGCAATGAAGCGTATG          AACCCCTTAGGATTATTCGTAGTGTTC
TCTCGCAGTTGCAGAGATGGTG          TCCGCGAAGAGAAGAGAGTGATGG
AGCGATTGTACCCCCACCATTC          GCTCGGCAATCTTCTTCCCTCTC
TGGTGTATTTTTGCTTTGTTTCTCAGG     GTTGTTCCGCTATGGGGCTAAGG
GTGCGGAAATCTCTGGCTC             AATCACTCAACCGCGAAACTCTATC
ATCAACCCCCAAATCACCAGAAAC        AATCGCGGTTAGCCACTTCATC
CGGCTGGCTTTATTTATCTGAGTTG       TTCGGGAAGCCTGTGGAAG
```

*FIG. 14B-2D*

| F28D6 | F28D6.58 | primer | 58994-59869 | Col Dom |
| F28D6 | F28D6.76 | primer | 76571-77289 | Lan & col |
| F28D6 | F28D6.93 | primer | 93823-94512 | Lan & Col |
| F28D6 | F28D6.120 | primer | 7985-8702 | Lan & Col |

FIG. 14B-1E

```
ACCCCCGAGCTCAACTTCTTAGG         GGACGGGGAGATGGGGATTACC
AGAATAGGAGCTGGGAGGTCAAAC        ATACTTAGATGCAATGGGTGTGGTG
CCCCATCCTGCCGACATAAAG           TACTCCGCATCATCTTCCATCTCTTC
GAGGGGCGAGTAGTTGAATCTGC         CCTAAGCCCGAAACCAAGTGAG
```

FIG. 14B-2E

```
                            SEQUENCE LISTING

<160> NUMBER OF SEQ ID NOS: 13

<210> SEQ ID NO 1
<211> LENGTH: 180
<212> TYPE: DNA
<213> ORGANISM: Brassica oleracea

<400> SEQUENCE: 1
agcttgattt ggatacataa agtggtggag aatcaccagg aagttgaata aatctcatag      60
gagttggcat gaagaagtta tcccactttc aaatcaggtg attccagttt cccagtttgg     120
gaatagcaca gcttcttcgt cgttccaatc aaaccaggat gaatcwcttt gtraraagct    180

<210> SEQ ID NO 2
<211> LENGTH: 180
<212> TYPE: DNA
<213> ORGANISM: Brassica oleracea

<400> SEQUENCE: 2
agcttgattt tgatacataa agtagtggag aatcaytwgg aagtggaata aatctcatag      60
gagttaggat gaagaagcta tcmcactttc aaatcaggtg atcccartttt tcctgtttgg    120 gaatatgaca acttmtttgt cattctaatc aaaccaggaw gaatcgcbat gtaaraagct    180

<210> SEQ ID NO 3
<211> LENGTH: 180
<212> TYPE: DNA
<213> ORGANISM: Brassica oleracea

<400> SEQUENCE: 3
agcttgattt ggatacataa agtggtggag aatcaccagg aagttgaata aatctcatag      60
gagttggsat gaagaagtta tcccactttc aaatcaggtg attccagttt cccagtttgg     120
gaatagcaca gcttcttcgt cgttccaatc aaaccaggat gaatcacttt gtragaagct    180

<210> SEQ ID NO 4
<211> LENGTH: 180
<212> TYPE: DNA
<213> ORGANISM: Brassica oleracea

<400> SEQUENCE: 4
agcttgattt tgatacataa agtartggag aatcayyagg aagtkgaata aatctcatag      60
gagttaggat gaagaagcta tcccactttc aaatcaggtg atcccartttt tcctgtttgg    120 gaatakgaca rcttctttgt cattctaatc aaaccaggaw gaatcgckat gtaaraagct    180

<210> SEQ ID NO 5
<211> LENGTH: 92
<212> TYPE: DNA
<213> ORGANISM: Glycine max

<400> SEQUENCE: 5
aaattcaaat ggtcataact tttmacwcgg akgtccgatt caggcgcata atatatcgag      60
acgctcgaaa ttgaacaayg gaagctctcg ag                                    92
```

<210> SEQ ID NO 6
<211> LENGTH: 91
<212> TYPE: DNA
<213> ORGANISM: Glycine max

<400> SEQUENCE: 6
aaattcaaac gacaataact ttttactcgg atgtcygatt gagtcccgta atatatcgag    60
acgctcgaaa ttgaatrytg aagctctgag c    91

<210> SEQ ID NO 7
<211> LENGTH: 92
<212> TYPE: DNA
<213> ORGANISM: Glycine max

<400> SEQUENCE: 7
aaattcaaat ggtcataact tttmacwcgg akgtccgatt caggcgcata atatatcgag    60
acgctcgaaa ttgaacaayg gaagctctcg ag    92

<210> SEQ ID NO 8
<211> LENGTH: 91
<212> TYPE: DNA
<213> ORGANISM: Glycine max

<400> SEQUENCE: 8
aaattcaaac gacaataact ttttactcgg atgtcygatt gagtcccgta atatatcgag    60
acgctcgaaa ttgaatrytg aagctctgag c    91

<210> SEQ ID NO 9
<211> LENGTH: 181
<212> TYPE: DNA
<213> ORGANISM: Lycopersicon esculentum

<400> SEQUENCE: 9
ccatcacggg ttttctgggc crtttggaag gtcaaacgag ccccggagcg agcatacgcc    60
tcattttgac gattttcgtg tgctattgca caccattttt tgggtgatcg ggattccgac   120
gtcaaaaatg ccaaatttgt tcgtggacgt ccgtcaagac gttgtctatg catacggttg   180
g    181

<210> SEQ ID NO 10
<211> LENGTH: 181
<212> TYPE: DNA
<213> ORGANISM: Lycopersicon esculentum

<400> SEQUENCE: 10
ccatcacggg ttttctgggc crtttggaag gtcaaacgag ccccgragcg agcatacgcc    60
tcattttgac gattttcgtg tgctattgca caccattttt tgggtgatcg ggattccgac   120
gtcaaaaatg ccaaatttgt tcgtggacgt ccgtcaagac gttgtctatg catacggttg   180
g    181

<210> SEQ ID NO 11
<211> LENGTH: 180
<212> TYPE: DNA
<213> ORGANISM: Zea mays

<400> SEQUENCE: 11
ggccacacaa ccccccatttt tgtcgaaaat agccatgaac gaccattttc aataatacyr    60
aaggctaaca cctacggatt tttraccaag aaatggtctc caccagaaat ccaagaatgt   120

```
gatctatggc aaggaaacat atgtggggtg aggtgtayga gcctctggtc gaygatcaat        180

<210> SEQ ID NO 12
<211> LENGTH: 180
<212> TYPE: DNA
<213> ORGANISM: Zea mays

<400> SEQUENCE: 12
ggccacacaa cccccatttt tgtcgaaaat agccatgaay gaccattttc aataataccg         60
aaggctaaca cctacggatt tttgaccaag aaatggtctc caccagaaat ccaagaatgt        120
gatctatggc aaggaaacat atgtggggtg aggtgtayga gcctctggtc gatgatcaat        180

<210> SEQ ID NO 13
<211> LENGTH: 158
<212> TYPE: DNA
<213> ORGANISM: Zea mays

<400> SEQUENCE: 13
ggttccggtg gcaaaaactc gtagctttgt atgcacccmg acacccgttt tcggaatggg         60
tgacgtgyga caacagaaat tgcgmgaaac caccccaaac atgagttttg kacctaaagt        120
agtggattgg gcatgttcgt tgygaaaaac gaagaaat                                158
```

PLANT CENTROMERE COMPOSITIONS

This application is a continuation of U.S. patent application Ser. No. 10/170,912 filed Jun. 12, 2002 now U.S. Pat. No. 7,119,250, which is a continuation-in-part of U.S. patent application Ser. No. 09/553,231, filed Apr. 19, 2000 now U.S. Pat. No. 6,900,012, which is a continuation of U.S. patent application Ser. No. 09/090,051, filed Jun. 3, 1998, now U.S. Pat. No. 6,156,953 which claims the priority of U.S. Provisional Patent Application Ser. No. 60/048,451, filed Jun. 3, 1997; and U.S. Provisional Patent Application Ser. No. 60/073,741, filed Feb. 5, 1998, both of the disclosures of which are specifically incorporated herein by reference in their entirety. U.S. patent application Ser. No. 10/170,912 also is a continuation-in-part of U.S. patent application Ser. No. 09/531,120, filed Mar. 17, 2000 now U.S. Pat. No. 6,972,197, which claims the priority of U.S. Provisional Application Ser. No. 60/125,219, filed Mar. 18, 1999; U.S. Provisional Application Ser. No. 60/127,409, filed Apr. 1, 1999; U.S. Provisional Application Ser. No. 60/134,770, filed May 18, 1999; U.S. Provisional Application Ser. No. 60/153,584, filed Sep. 13, 1999, U.S. Provisional Application Ser. No. 60/154,603, filed Sep. 17, 1999 and U.S. Provisional Application Ser. No. 60/172,493, filed Dec. 16, 1999, each of which disclosures is specifically incorporated herein by reference in its entirety.

The government owns rights in the present invention pursuant to U.S. Department of Agriculture Grant No. 96-35304-3491 and Grant No. DE-FC05-920R22072 from the Consortium for Plant Biotechnology Research, National Science Foundation Grant No. 9872641, and Department of Energy Small Business Innovation Research Grants DE-FG02-01ER83163, DE-FG02-01ER83165, and DE-FG02-01ER83166.

BACKGROUND OF THE INVENTION

Two general approaches are used for introduction of new genetic information ("transformation") into cells. One approach is to introduce the new genetic information as part of another DNA molecule, referred to as an "episomal vector," or "minichromosome", which can be maintained as an independent unit (an episome) apart from the host chromosomal DNA molecule(s). Episomal vectors contain all the necessary DNA sequence elements required for DNA replication and maintenance of the vector within the cell. Many episomal vectors are available for use in bacterial cells (for example, see Maniatis et al., 1982). However, only a few episomal vectors that function in higher eukaryotic cells have been developed. Higher eukaryotic episomal vectors were primarily based on naturally occurring viruses. In higher plant systems gemini viruses are double-stranded DNA viruses that replicate through a double-stranded intermediate upon which an episomal vector could be based, although the gemini virus is limited to an approximately 800 bp insert. Although an episomal plant vector based on the Cauliflower Mosaic Virus has been developed, its capacity to carry new genetic information also is limited (Brisson et al., 1984).

The other general method of genetic transformation involves integration of introduced DNA sequences into the recipient cell's chromosomes, permitting the new information to be replicated and partitioned to the cell's progeny as a part of the natural chromosomes. The introduced DNA usually is broken and joined together in various combinations before it is integrated at random sites into the cell's chromosome (see, for example Wigler et al., 1977). Common problems with this procedure are the rearrangement of introduced DNA sequences and unpredictable levels of expression due to the location of the transgene in the genome or so called "position effect variation" (Shingo et al., 1986). Further, unlike episomal DNA, integrated DNA cannot normally be precisely removed. A more refined form of integrative transformation can be achieved by exploiting naturally occurring viruses that integrate into the host's chromosomes as part of their life cycle, such as retroviruses (see Cepko et al., 1984). In mouse, homologous integration has recently become common, although it is significantly more difficult to use in plants (Lam et al. 1996).

The most common genetic transformation method used in higher plants is based on the transfer of bacterial DNA into plant chromosomes that occurs during infection by the phytopathogenic soil bacterium *Agrobacterium* (see Nester et al., 1984). By substituting genes of interest for the naturally transferred bacterial sequences (called T-DNA), investigators have been able to introduce new DNA into plant cells. However, even this more "refined" integrative transformation system is limited in three major ways. First, DNA sequences introduced into plant cells using the *Agrobacterium* T-DNA system are frequently rearranged (see Jones et al., 1987). Second, the expression of the introduced DNA sequences varies between individual transformants (see Jones et al., 1985). This variability is presumably caused by rearranged sequences and the influence of surrounding sequences in the plant chromosome (i.e., position effects), as well as methylation of the transgene. A third drawback of the *Agrobacterium* T-DNA system is the reliance on a "gene addition" mechanism: the new genetic information is added to the genome (i.e., all the genetic information a cell possesses) but does not replace information already present in the genome.

One attractive alternative to commonly used methods of transformation is the use of an artificial chromosome. Artificial chromosomes are man-made linear or circular DNA molecules constructed from cis-acting DNA sequence elements that provide replication and partitioning of the constructed chromosomes (see Murray et al., 1983). Desired elements include: (1) Autonomous Replication Sequences (ARS) (these have properties of replication origins, which are the sites for initiation of DNA replication), (2) Centromeres (site of kinetochore assembly and responsible for proper distribution of replicated chromosomes at mitosis or meiosis), and (3) if the chromosome is linear, telomeres (specialized DNA structures at the ends of linear chromosomes that function to stabilize the ends and facilitate the complete replication of the extreme termini of the DNA molecule).

The essential chromosomal elements for construction of artificial chromosomes have been precisely characterized in lower eukaryotic species, and more recently in mouse and human. ARSs have been isolated from unicellular fungi, including *Saccharomyces cerevisiae* (brewer's yeast) and *Schizosaccharomyces pombe* (see Stinchcomb et al., 1979 and Hsiao et al., 1979). An ARS behaves like a replication origin allowing DNA molecules that contain the ARS to be replicated as an episome after introduction into the cell nuclei of these fungi. DNA molecules containing these sequences replicate, but in the absence of a centromere they are partitioned randomly into daughter cells.

Artificial chromosomes have been constructed in yeast using the three cloned essential chromosomal elements. Murray et al., 1983, disclose a cloning system based on the in vitro construction of linear DNA molecules that can be transformed into yeast, where they are maintained as artificial chromosomes. These yeast artificial chromosomes (YACs) contain cloned genes, origins of replication, centromeres and telomeres and are segregated in daughter cells with high fidelity when the YAC is at least 100 kB in length. Smaller CEN-containing vectors may be stably segregated, however, when in circular form.

None of the essential components identified in unicellular organisms, however, function in higher eukaryotic systems. For example, a yeast CEN sequence will not confer stable inheritance upon vectors transformed into higher eukaryotes. While such DNA fragments can be readily introduced, they do not stably exist as episomes in the host cell. This has seriously hampered efforts to produce artificial chromosomes in higher organisms.

In one case, a plant artificial chromosome was discussed (Richards et al., U.S. Pat. No. 5,270,201). However, this vector was based on plant telomeres, as a functional plant centromere was not disclosed. While telomeres are important in maintaining the stability of chromosomal termini, they do not encode the information needed to ensure stable inheritance of an artificial chromosome. It is well documented that centromere function is crucial for stable chromosomal inheritance in almost all eukaryotic organisms (reviewed in Nicklas 1988). For example, broken chromosomes that lack a centromere (acentric chromosomes) are rapidly lost from cell lines, while fragments that have a centromere are faithfully segregated. The centromere accomplishes this by attaching, via centromere binding proteins, to the spindle fibers during mitosis and meiosis, thus ensuring proper gene segregation during cell divisions.

In contrast to the detailed studies done in S. cerevisiae and S. pombe, less is known about the molecular structure of functional centromeric DNA of higher eukaryotes. Ultrastructural studies indicate that higher eukaryotic kinetochores, which are specialized complexes of proteins that form on the centromere during late prophase, are large structures (mammalian kinetochore plates are approximately 0.3 μm in diameter) which possess multiple microtubule attachment sites (reviewed in Rieder, 1982). It is therefore possible that the centromeric DNA regions of these organisms will be correspondingly large, although the minimal amount of DNA necessary for centromere function may be much smaller.

The above studies have been useful in elucidating the structure and function of centromeres. The extensive literature indicating both the necessity of centromeres for stable inheritance of chromosomes, and the non-functionality of yeast centromeres in higher organisms, demonstrate that cloning of a functional centromere from a higher eukaryote is a necessary first step in the production of artificial chromosomes suitable for use in higher plants and animals. The production of artificial chromosomes with centromeres which function in higher eukaryotes would overcome many of the problems associated with the prior art and represent a significant breakthrough in biotechnology research.

SUMMARY OF THE INVENTION

The present invention allows the isolation and identification of plant centromere DNA sequences from the total genomic DNA of an organism or fractions thereof. With centromere DNA sequences, it is possible to construct chromosomes having functional centromeres and carrying large number of genes. Genes for producing a vast set of products have been identified, but technologies used within the industry severely limit the delivery of these genes to plant cells. One or at most a few genes are typically inserted into random locations in the host chromosomes, which can irreversibly disrupt host gene functions while causing variable and uncontrolled expression of the introduced genes. The present invention makes it possible to overcome the technical limitations associated with gene delivery in crop species, thereby allowing for the ability to shorten the time required for crop development.

In one aspect, the invention provides a method to obtain a centromere DNA sequence from a selected organism, the method comprising the steps of preparing a sample of genomic DNA from a selected organism, obtaining a plurality of nucleic acid segments from the genomic DNA and screening the nucleic acid segments to identify one or more centromere nucleic acid sequences. In an embodiment, the method of obtaining the plurality of nucleic acid segments comprises contacting said genomic DNA with a restriction endonuclease and selecting nucleic acid segments containing repetitive DNA to obtain said plurality of nucleic acid segments. In another embodiment, the method of obtaining the plurality of nucleic acid segments comprises contacting said genomic DNA with a methylation sensitive restriction endonuclease and selecting nucleic acid segments exhibiting resistance to cleavage with said methylation sensitive restriction endonuclease to obtain said plurality of nucleic acid segments. In yet another embodiment, the method of obtaining the plurity of nucleic acid segments comprises contacting said genomic DNA with a restriction endonuclease or physically shearing said genomic DNA and selecting nucleic acid segments that anneal rapidly after denaturation to obtain said plurality of nucleic acid segments.

In another aspect, the invention provides a method for identifying a centromere nucleic acid sequence from a dataset of the genomic sequences of an organism. The method comprises the steps of (1) providing a first dataset consisting of the genomic sequences, or a representative fraction of genomic sequence, of the organism; (2) identifying and eliminating known non-centromeric repeat sequences from the first dataset by using the BLAST sequence comparison algorithm to create a second dataset; (3) comparing each sequence in the second dataset to itself by using the BLAST sequence comparison algorithm, obtaining a BLAST score for each pair of sequence compared, and collecting high score pairs to create a third dataset; (4) examining the BLAST score of each high score pair in the third dataset and eliminating the pairs having a score greater than $10^{-20}$ to create a fourth dataset; (5) eliminating the high score pairs in the fourth dataset having less than 80 bp or more than 250 bp to create a fifth dataset; (6) examining the nucleotide position of each high score pair in the fifth dataset and eliminating pairs having 100% identity as well as identical nucleotide positions to create a sixth dataset; (7) examining the nucleotide position of each high score pair in the sixth dataset and eliminating pairs having opposite orientation of the nucleotides to create a seventh dataset; (8) examining the nucleotide position of both sequences for each high score pair in the seventh dataset and eliminating sequences that are overlapping to create an eighth dataset; and (9) examining the nucleotide position of each sequence in the eighth dataset and eliminating sequences not having at least one neighboring sequence within 250 bp to create a ninth dataset; and (10) comparing each sequence in the ninth dataset to all other sequences in the ninth dataset by using the BLAST sequence comparison algorithm and selecting the most common sequence as a centromere sequence of the organism. In one embodiment, the known non-centromeric repeat sequence in the second step is a ribosomal DNA.

In another aspect, the invention provides a *Brassica oleracea* centromere comprising *Brassica oleracea* centromere DNA. In one embodiment, the *Brassica oleracea* centromere is defined as comprising n copies of a repeated nucleotide sequence, wherein n is at least 2. Potentially any number of repeat copies capable of physically being placed on the recombinant construct could be included on the construct, including about 5, 10, 15, 20, 30, 50, 75, 100, 150, 200, 300, 400, 500, 750, 1,000, 1,500, 2,000, 3,000, 5,000, 7,500, 10,000, 20,000, 30,000, 40,000, 50,000, 60,000, 70,000, 80,000, 90,000 and about 100,000, including all ranges in-between such copy numbers. In one embodiment, the repeated nucleotide sequence is isolated from *Brassica oleracea* given by SEQ ID NO:1, 2, 3, or 4.

In yet another aspect, the invention provides a *Glycine max* centromere comprising *glycine max* centromere DNA. In an embodiment, the *Glycine max* centromere is defined as comprising n copies of a repeated nucleotide sequence, wherein n is at least 2. Potentially any number of repeat copies capable of physically being placed on the recombinant construct could be included on the construct, including about 5, 10, 15, 20, 30, 50, 75, 100, 150, 200, 300, 400, 500, 750, 1,000, 1,500, 2,000, 3,000, 5,000, 7,500, 10,000, 20,000, 30,000, 40,000, 50,000, 60,000, 70,000, 80,000, 90,000 and about 100,000, including all ranges in-between such copy numbers. In one embodiment, the repeated nucleotide sequence is isolated from *Glycine max* given by SEQ ID NO:5, 6, 7, or 8.

In yet another aspect, the invention provides a *Lycopersicon esculentum* centromere comprising *Lycopersicon esculentum* centromere DNA. In an embodiment, the *Lycopersicon esculentum* centromere is defined as comprising n copies of a repeated nucleotide sequence, wherein n is at least 2. Potentially any number of repeat copies capable of physically being placed on the recombinant construct could be included on the construct, including about 5, 10, 15, 20, 30, 50, 75, 100, 150, 200, 300, 400, 500, 750, 1,000, 1,500, 2,000, 3,000, 5,000, 7,500, 10,000, 20,000, 30,000, 40,000, 50,000, 60,000, 70,000, 80,000, 90,000 and about 100,000, including all ranges in-between such copy numbers. In one embodiment, the repeated nucleotide sequence is isolated from *Lycopersicon esculentum* given by SEQ ID NO:9 or 10.

In yet another aspect, the invention provides a *Zea mays* centromere comprising *Zea mays* centromere DNA. In an embodiment, the centromere is defined as comprising n copies of a repeated nucleotide sequence, wherein n is at least 2. Potentially any number of repeat copies capable of physically being placed on the recombinant construct could be included on the construct, including about 5, 10, 15, 20, 30, 50, 75, 100, 150, 200, 300, 400, 500, 750, 1,000, 1,500, 2,000, 3,000, 5,000, 7,500, 10,000, 20,000, 30,000, 40,000, 50,000, 60,000, 70,000, 80,000, 90,000 and about 100,000, including all ranges in-between such copy numbers. In one embodiment, the repeated nucleotide sequence is isolated from *Zea mays* given by SEQ ID NO:11, 12 or 13.

In yet another aspect, the invention provides a recombinant DNA construct comprising a plant centromere sequence of the present invention. The recombinant DNA construct may additionally comprise any other desired sequences, for example, a telomere. Still further, one may wish to include a structural gene on the construct, or multiple genes. Examples of structural genes one may wish to use include a selectable or screenable marker gene, an antibiotic resistance gene, a ligand gene, an enzyme gene, a herbicide resistance gene, a nitrogen fixation gene, a plant pathogen defense gene, a plant stress-induced gene, a toxin gene, a receptor gene, a gene encoding an enzyme, a gene encoding an antibody, a gene encoding an antigen for a vaccine, a transcription factor, a cytoskeletal protein, a DNA-binding protein, a protease, an endonuclease, a lipid, a seed storage gene, an interleukin gene, a clotting factor gene, a cytokine gene, a growth factor gene and a biosynthetic gene for producing pharmaceutically active proteins, small molecules with medicinal properties, chemicals with industrial utility, nutraceuticals, carbohydrates, RNAs, lipids, fuels, dyes, pigments, vitamins, scents, flavors, vaccines, antibodies, and hormones. In one embodiment of the invention, the construct is capable of expressing the structural gene, for example, in a prokaryote or eukaryote, including a lower eukaryote, or a higher eukaryote such as a plant. Moreover, the recombinant construct could contain other useful non-coding sequences, including promoters, terminators, boundary elements that regulate gene expression, sequences that alter maintenance, inheritance, or stability of the construct, and sequences that allow subsequent modification of the composition of the construct.

In still yet another aspect, the invention provides a recombinant DNA construct comprising a plant centromere sequence of the present invention and which is capable of being maintained as a chromosome, wherein the chromosome is transmitted in dividing cells. The plant centromere may be from any plant or may be from any other source of DNA or may be partially or entirely synthetic in origin.

In yet another aspect, the invention provides a recombinant DNA construct comprising a plant centromere sequence of the present invention and which is a plasmid. The plasmid may contain any desired sequences, such as an origin of replication. The plasmid may also comprise a selection marker.

In still yet another aspect, the invention provides a minichromosome comprising a plant centromere sequence of the present invention and may also contain a telomere sequence. Any additional desired sequences may be added to the minichromosome, such as an autonomous replicating sequence and a structural gene such as those described above. The minichromosome may comprise any of the centromere compositions disclosed herein.

The minichromosome also may contain "negative" selectable markers which confer susceptibility to an antibiotic, herbicide or other agent, thereby allowing for selection against plants, plant cells or cells of any other organism of interest containing a minichromosome. The minichromosome also may include genes or other sequences which control the copy number of the minichromosome within a cell. One or more structural genes also may be included in the minichromosome. Specifically contemplated as being useful will be as many structural genes as may be inserted into the minichromosome.

In still yet another aspect, the invention provides a cell transformed with a recombinant DNA construct comprising a plant centromere sequence of the present invention. The cell may be of any type, including a prokaryotic cell or eukaryotic cell. Where the cell is a eukaryotic cell, the cell may be, for example, a yeast cell or a higher eukaryotic cell, such as plant cell. The plant cell may be from a dicotyledonous plant, such as tobacco, tomato, potato, soybean, canola, sunflower, alfalfa, cotton and *Arabidopsis*, or may be a monocotyledonous plant cell, such as wheat, maize, rye, rice, turfgrass, oat, barley, sorghum, millet, and sugarcane. In one embodiment of the invention, the plant centromere is a centromere chosen from the group consisting of *Brassica oleracea, Glycine max, Lycopersicon esculentum,* and *Zea mays* and the cell may be a cell chosen from one of the above species or any other species. The recombinant DNA construct may comprise additional sequences, such as a telomere, an autonomous replicating sequence (ARS), a structural gene or genes, or a selectable or screenable marker gene or genes, including as many of such sequences as may physically be placed on said recombinant DNA construct. In one embodiment of the invention, the cell is further defined as capable of expressing said structural gene. In another embodiment of the invention, a plant is provided comprising the aforementioned cells.

In still yet another aspect, the invention provides a method for preparing a transgenic plant cell. The method comprises the steps of contacting a starting plant cell with a recombinant DNA construct comprising a plant centromere sequence of the present invention, whereby the starting plant cell is transformed with the recombinant DNA construct.

In still yet another aspect, the invention provides a transgenic crop comprising a minichromosome, wherein the minichromosome comprises a plant centromere sequence of the present invention. The minichromosome may further comprise a telomere sequence, an autonomous replicating sequence or a structural gene, such as a selectable or screenable marker gene, an antibiotic resistance gene, a ligand gene, an enzyme gene, a herbicide resistance gene, a nitrogen fixation gene, a plant pathogen defense gene, a plant stress-induced gene, a toxin gene, a receptor gene, a gene encoding an enzyme, a gene encoding an antibody, a gene encoding an antigen for a vaccine, a transcription factor, a cytoskeletal protein, a DNA-binding protein, a protease, an endonuclease, a lipid, a seed storage gene, an interleukin gene, a clotting factor gene, a cytokine gene, a growth factor gene and a biosynthetic gene for producing pharmaceutically active proteins, small molecules with medicinal properties, chemicals with industrial utility, nutraceuticals, carbohydrates, RNAs, lipids, fuels, dyes, pigments, vitamins, scents, flavors, vaccines, antibodies, and hormones. The transgenic crop may be any type of crop, such as a dicotyledonous plant, for example, tobacco, tomato, potato, pea, carrot, cauliflower, broccoli, soybean, canola, sunflower, alfalfa, cotton and *Arabidopsis*, or may be a monocotyledonous plant, such as wheat, maize, rye, rice, turfgrass, oat, barley, sorghum, millet, and sugarcane.

In still yet another aspect, the invention provides a method for preparing a transgenic crop tissue. The method comprises the steps of contacting a starting crop tissue with a recombinant DNA construct comprising a plant centromere sequence of the present invention, whereby the starting crop tissue is transformed with the recombinant DNA construct.

In still yet another aspect, the invention provides a method for preparing a transgenic crop seed. The method comprises the steps of contacting a starting crop, crop tissue, or crop cell, with a recombinant DNA construct comprising a plant centromere sequence of the present invention, whereby the starting crop, crop tissue, or crop cell is transformed with the recombinant DNA construct. These transformed crops, crop tissues, or crop cells are allowed to develop into mature crops, using standard agricultural techniques. Transgenic seed is then collected from these crops.

In still yet another aspect, the invention provides a method for preparing an extract of a transgenic crop, crop tissue, crop seed, or crop cell. The method comprises the steps of contacting a starting crop, crop tissue, or crop cell with a recombinant DNA construct comprising a plant centromere sequence of the present invention, whereby the starting crop cell is transformed with the recombinant DNA construct. The resulting transgenic crop, crop tissue, crop seed, or crop cell is then extracted and processed to yield the desirable product. One preferred desirbale product is a food product. Another preferred desirable product is a pharmaceutical product. Yet another preferred desirable product is a chemical product.

Additional features and advantages of the present invention are described in, and will be apparent from, the following Detailed Description of the Invention and the figures.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIG. 1A–F Consensus sequences of repeats from *Brassica oleracea* FIG. 1A is the consensus sequence of ChrBo1. This consensus was assembled from 33 sequences collected by the inventors. The length of this repeat is 180±0.86 base pairs and A and T compose 60% of the consensus. FIG. 1B is the consensus sequence of ChrBo2. This consensus was assembled from 7 sequences collected by the inventors. The length of this repeat is 180±0.45 base pairs and A and T compose 63% of the consensus. FIG. 1C is a comparison of the consensus sequences of ChrBo1 and ChrBo2. The two repeats (ChrBo1 and ChrBo2) were alligned to each other using the ClustalX program (ClustalX is a free multiple sequence alignment program for Windows. Those sites with significant differences between the two sequences (Chi-squared, $P<0.05$) are highlighted. FIG. 1D is a revised consensus sequence of ChrBo1. This consensus was assembled from 33 DNA sequences collected by the inventors and 18 sequences from Genbank, identified by the assession numbers:

Figure 5:
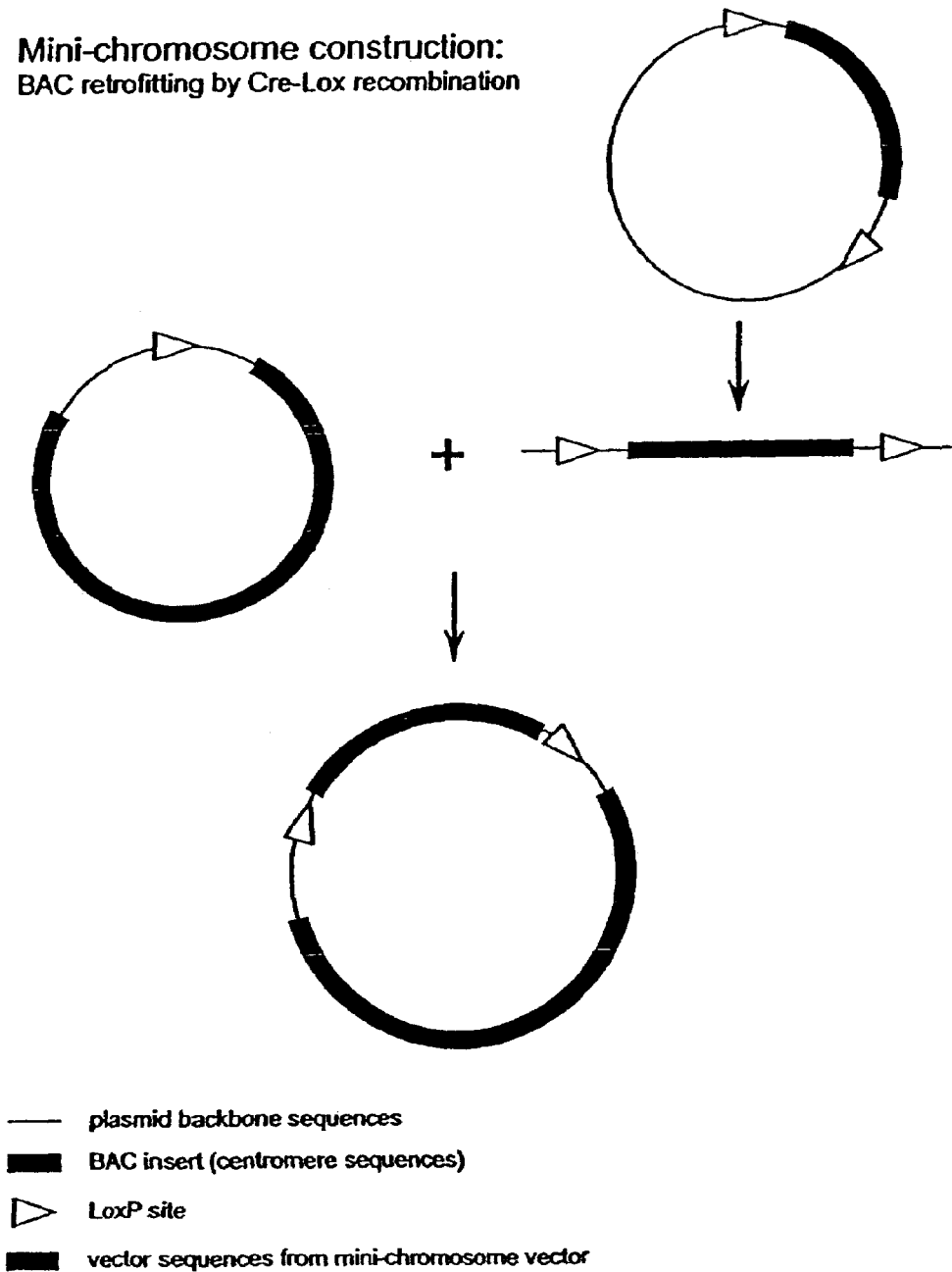

| M30962 | M30963 | M31436 | M31435 |
| M31438 | M31434 | M31439 | M31437 |
| X68786 | X12736 | X07519 | X16589 |
| X15291 | X68783 | X68784 | X61583 |
| AJ228348 | Z22947 | | |

FIG. 1E is a revised consensus sequence of ChrBo2. This consensus was assembled from 7 DNA sequences collected by the inventors and 5 sequences from Genbank, identified by the accession numbers AJ228347, M30962, X12736, X61583, and X68785. FIG. 1F is a comparison of the revised consensus sequences of ChrBo1 and ChrBo2, aligned as for FIG. 1C.

FIGS. 2A–F Consensus sequences of repeats from *Glycine max*. FIG. 2A is a consensus sequence of ChrGm1. This consensus was assembled from 32 sequences collected by the inventors. The length of this repeat is 92 0.79 base pairs and A and T compose 63% of the consensus. FIG. 2B is a consensus sequence of ChrGm2. This consensus was assembled from 21 sequences collected by the inventors. The length of this repeat is 91 048 base pairs and A and T compose 62% of the consensus. FIG. 2C is a comparison of the consensus sequences of ChrGm1 and ChrGm2. The two repeats (ChrGm1 and ChrGm2) were aligned to each other using the ClustalX program (ClustalX is a free multiple sequence alignment program for Windows. Those sites with significant differences between the two sequences (Chi-squared, $P<0.05$) are highlighted. FIG. 2D is a revised consensus sequence of ChrGm1. This consensus was assembled from 32 DNA sequences collected by the inventors and 1 sequence from Genbank, identified by the accession number Z26334. FIG. 2E is a revised consensus sequence of ChrGm2. This consensus was assembled from 21 DNA sequences collected by the inventors and 13 sequences from Genbank, identified by the accession numbers AF297983, AF297984, and AF297985. FIG. 2F is a comparison of the revised consensus sequences of ChrGm1 and ChrGm2, aligned as for FIG. 2C.

FIGS. 3A–B Consensus sequences of repeats from *Lycopersicon esculentum*. FIG. 3A is a consensus sequence of ChrLe1. This consensus was assembled from 42 sequences collected by the inventors. The length of this repeat is 181 0.61 base pairs and A and T compose 50% of the consensus. FIG. 3B is a revised consensus sequence of ChrLe1. This consensus was assembled from 32 sequences collected by the inventors and 2 Genbank sequences identified by the accession numbers X87233 and AY007367.

FIGS. 4A–C Consensus sequences of repeats from *Zea mays*. FIG. 4A is a consensus sequence of ChrZm1. This consensus was assembled from 38 sequences collected by the inventors. The length of this repeat is 180 1.15 base pairs and A and T compose 56% of the consensus. FIG. 4B is a revised consensus sequence of ChrZm1. This consensus was assembled from 38 sequences collected by the inventors and 26 sequences from Genbank, identified by the accession numbers:

| M32521 | M32522 | M32523 | M32524 | M32525 | M32526 |
| M32527 | M32528 | M32529 | M32530 | M32531 | M32532 |
| M32533 | M32534 | M325375 | M32536 | M32537 | M32538 |
| M35408 | AF030934 | AF030935 | AF030936 | AF030937 | AF030938 |
| AF030939 | AF030940 | | | | |

FIG. 4C is a consensus sequence of ChrZm2. This consensus was assembled from 6 sequences collected from Genbank identified by the accession numbers:

| AF078918 | AF078919 | AF078920 |
| AF0789121 | AF078922 | AF078923 |

The length of this repeat is 158 1.6 base pairs and A and T compose 53% of the consensus.

Figure 6:
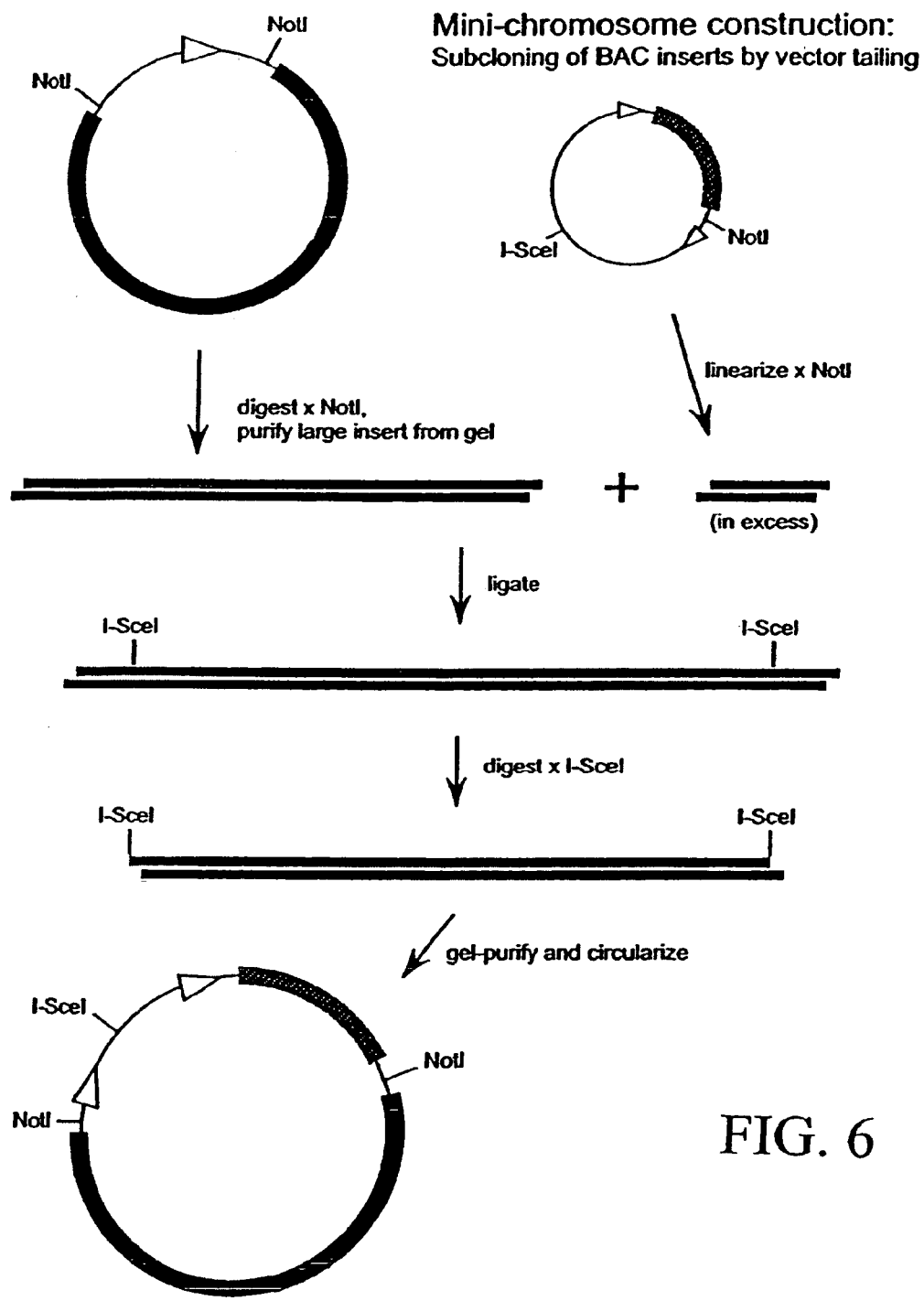

FIG. 5 Minichromosome containing centromere sequences as well as minichromosome vector sequences FIG. 6 Minichromosome construct formed by minichromosome vector tailing method.

Figure 7A:
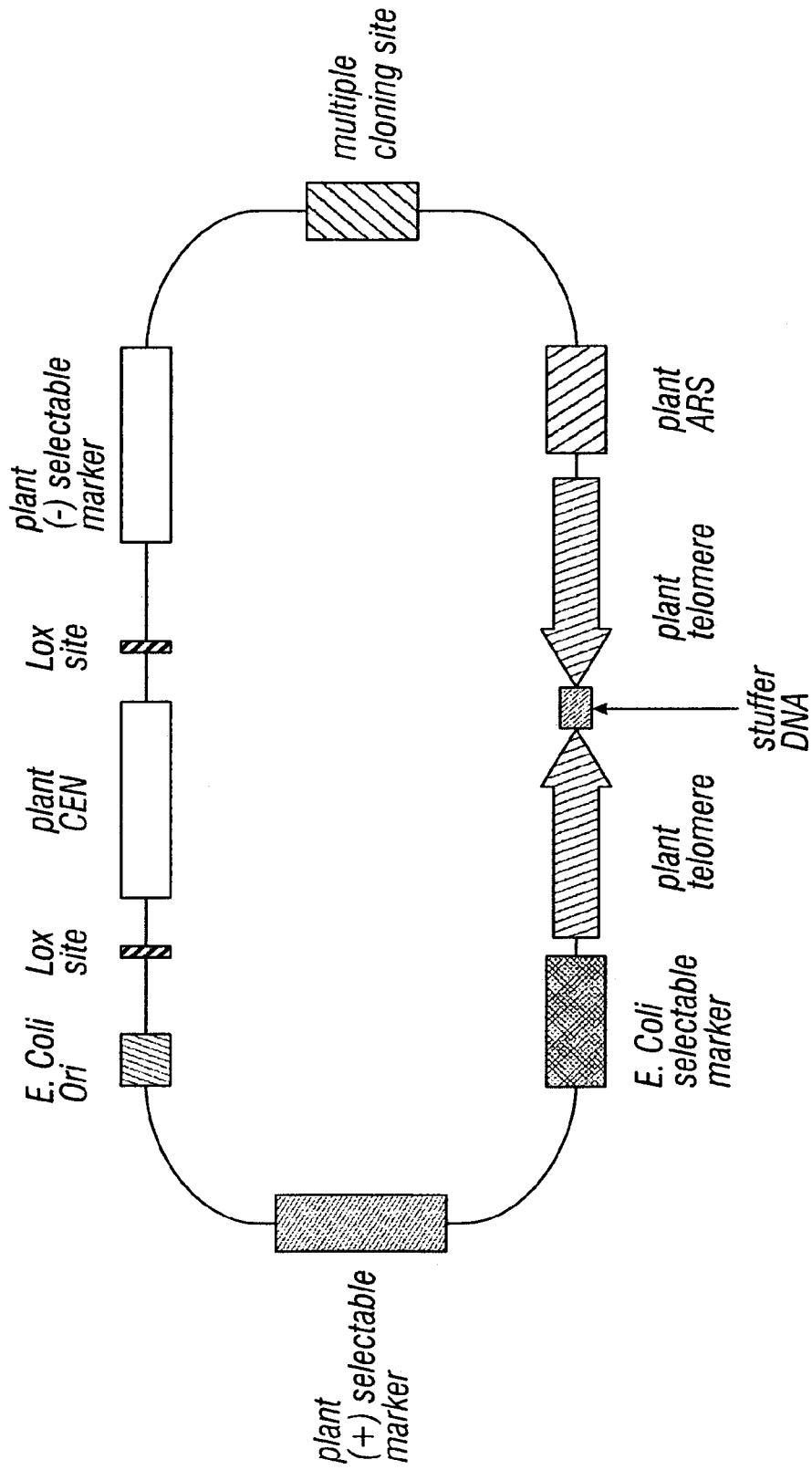
Figure 7B:
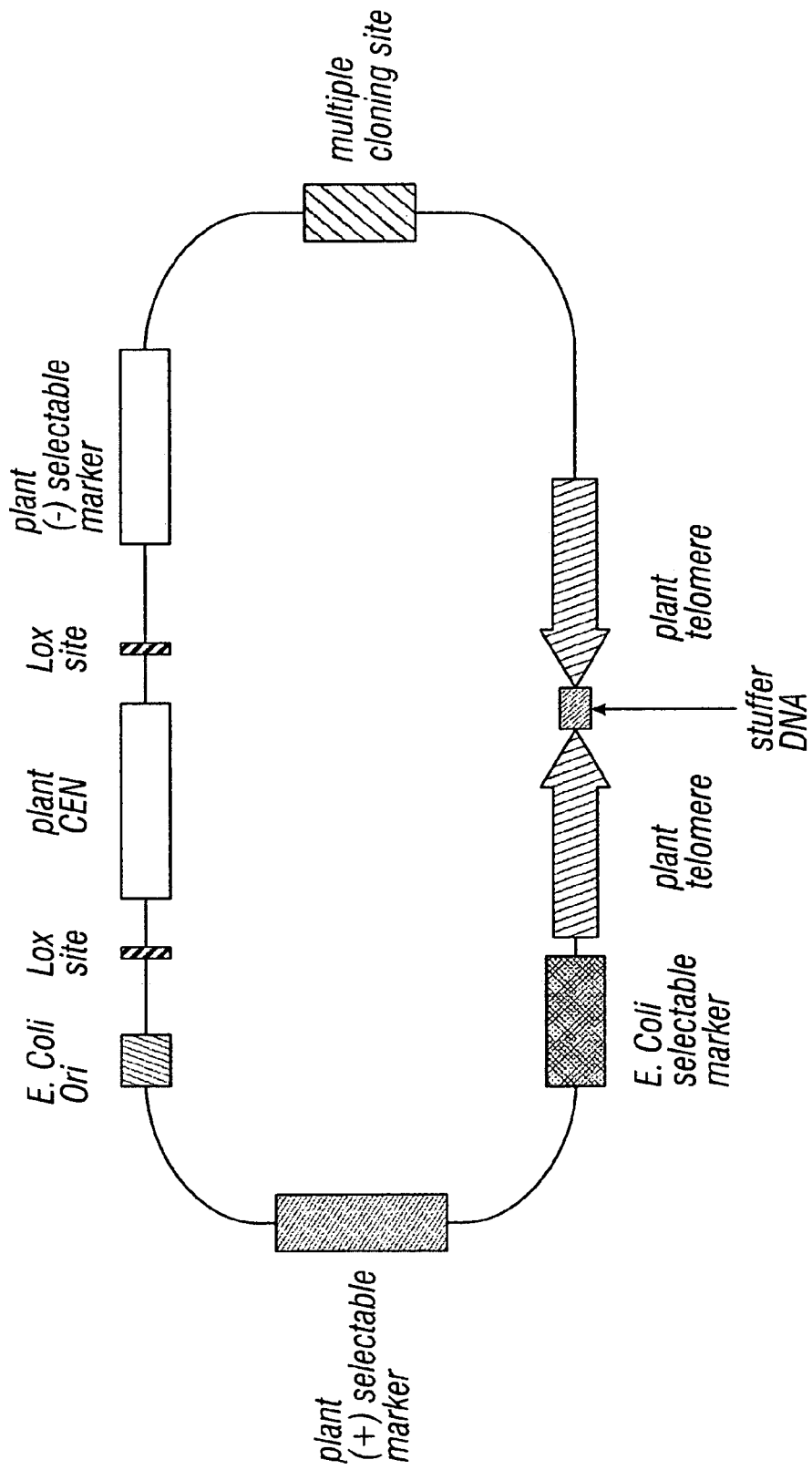
Figure 7C:
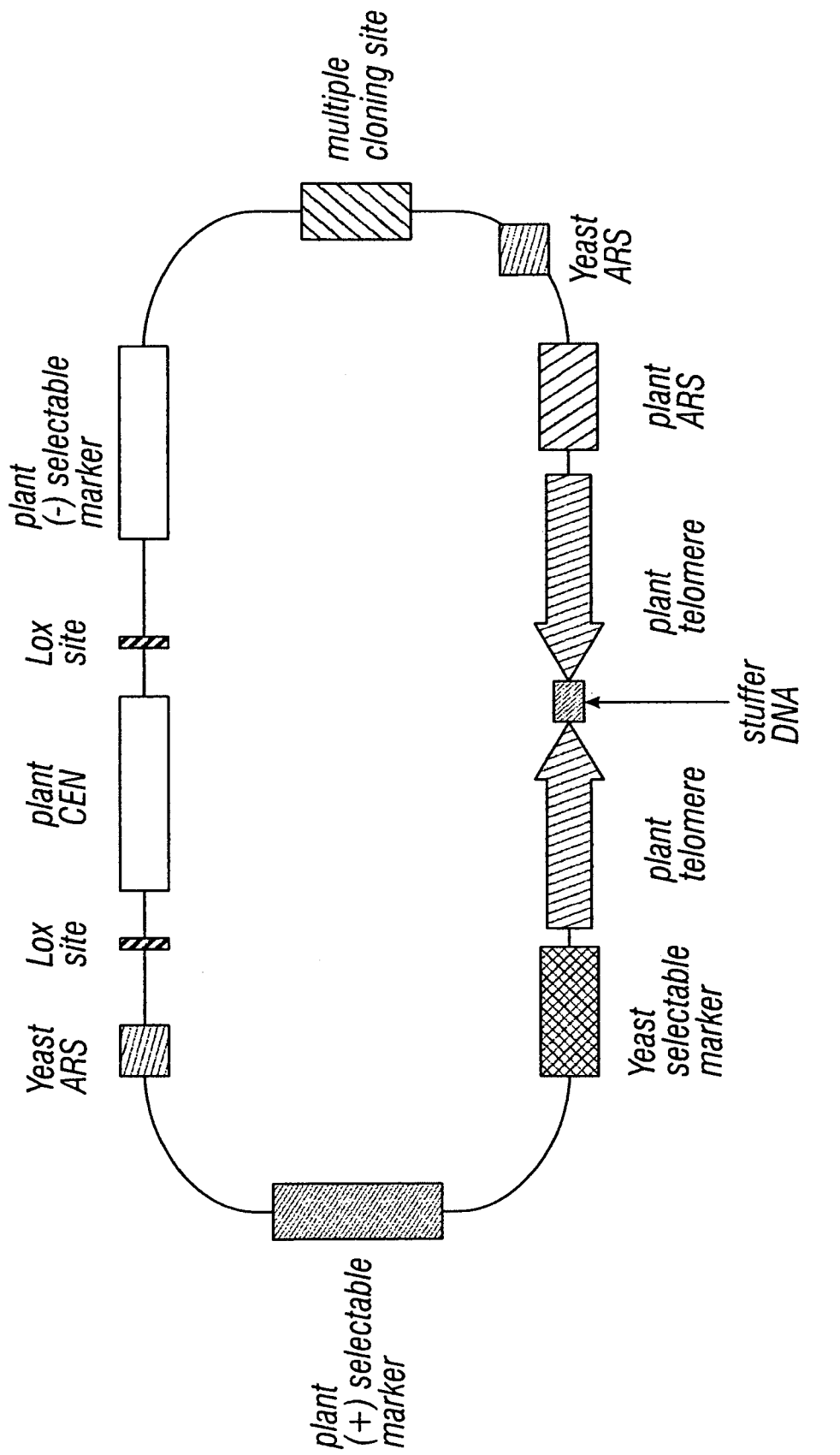
Figure 7D:
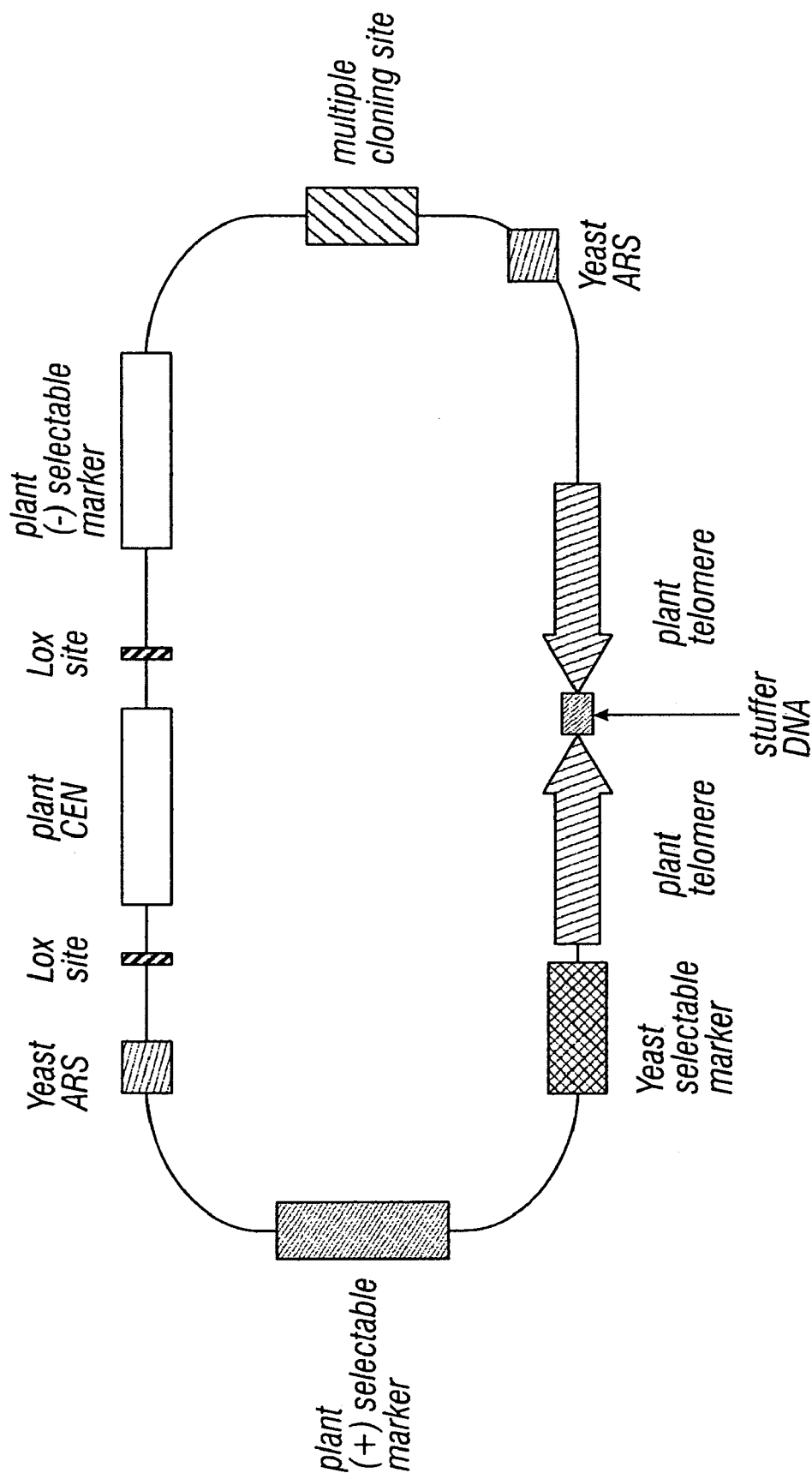
Figure 7E:
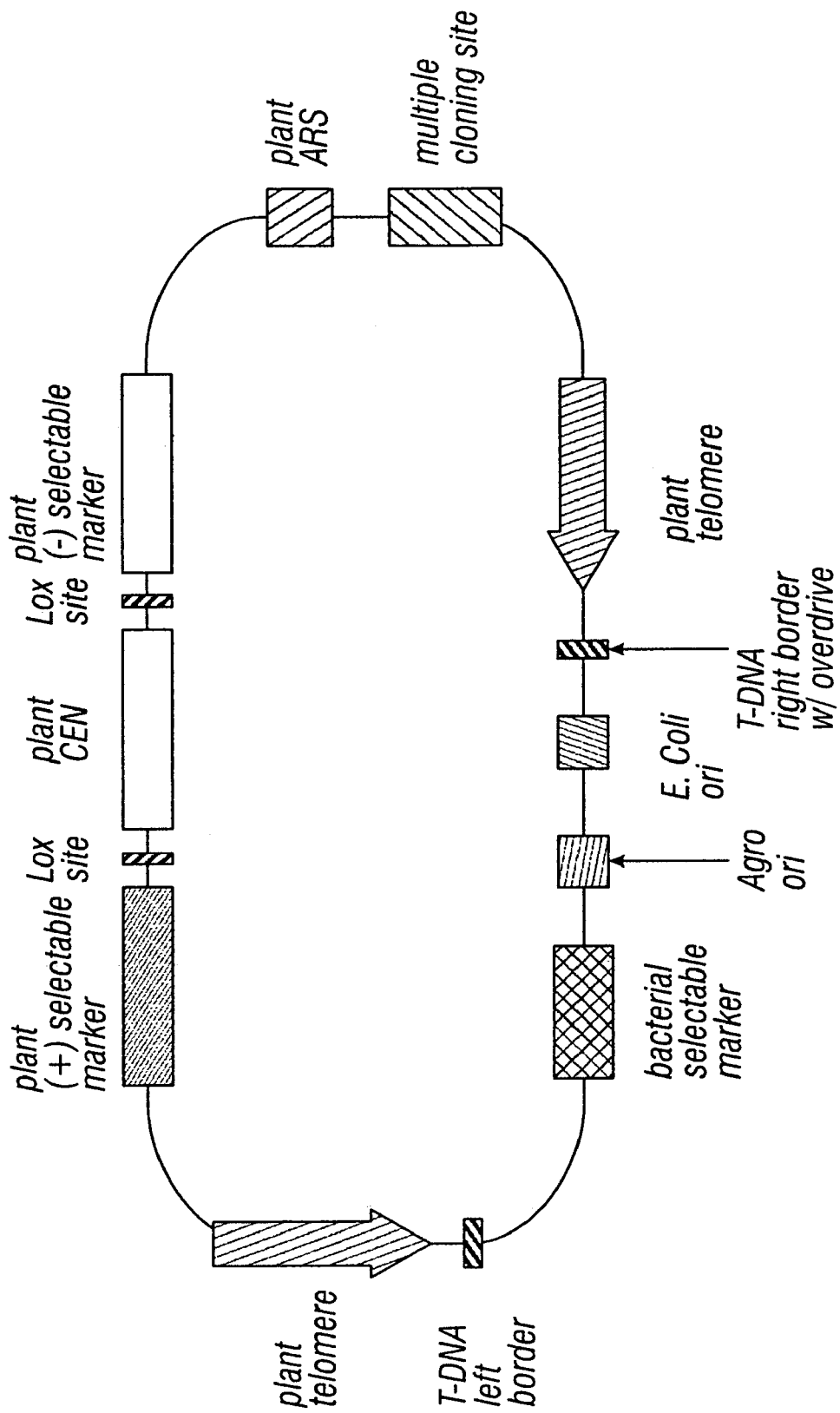
Figure 7F:
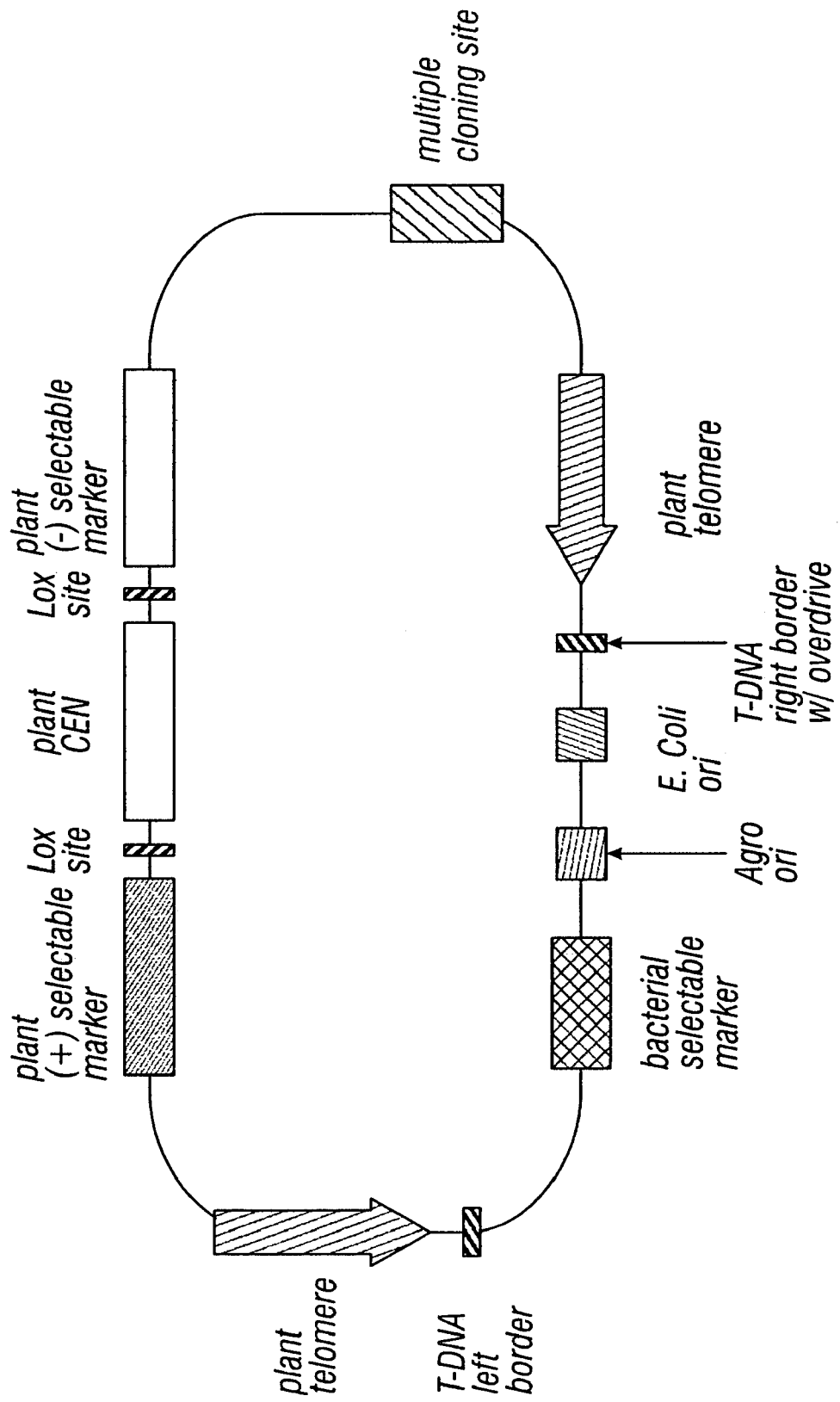
Figure 71:
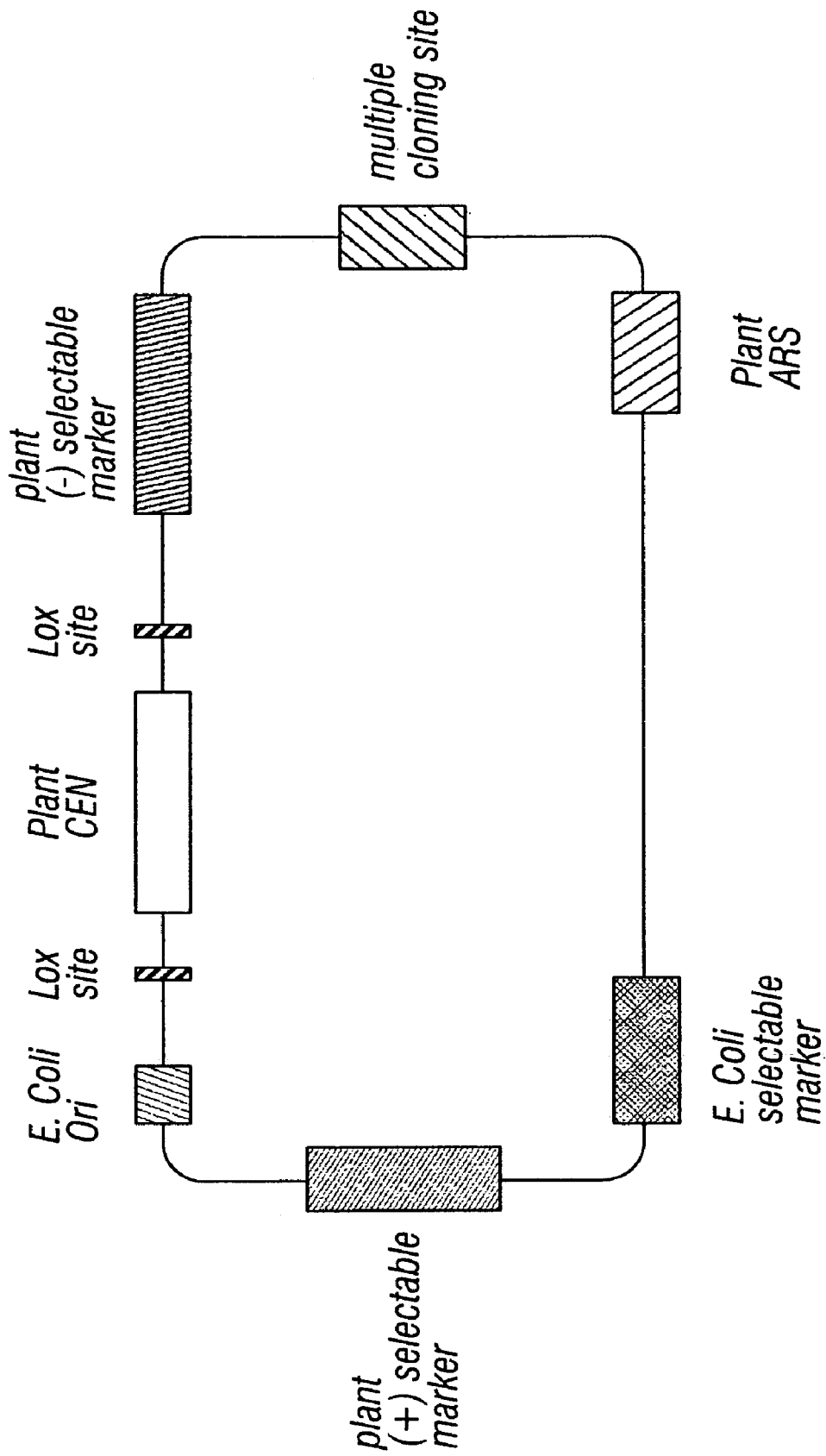
Figure 7J:
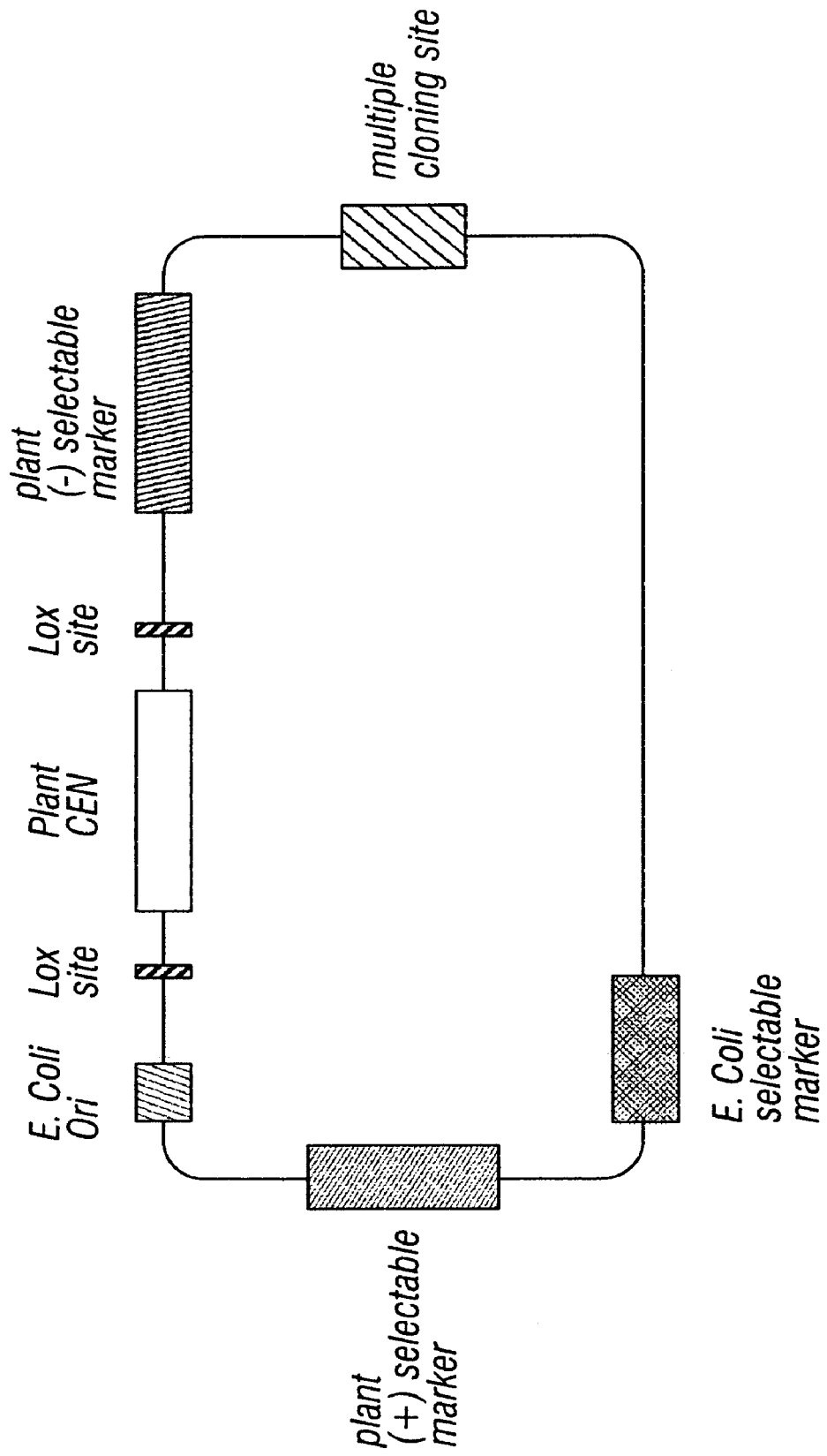
Figure 7K:
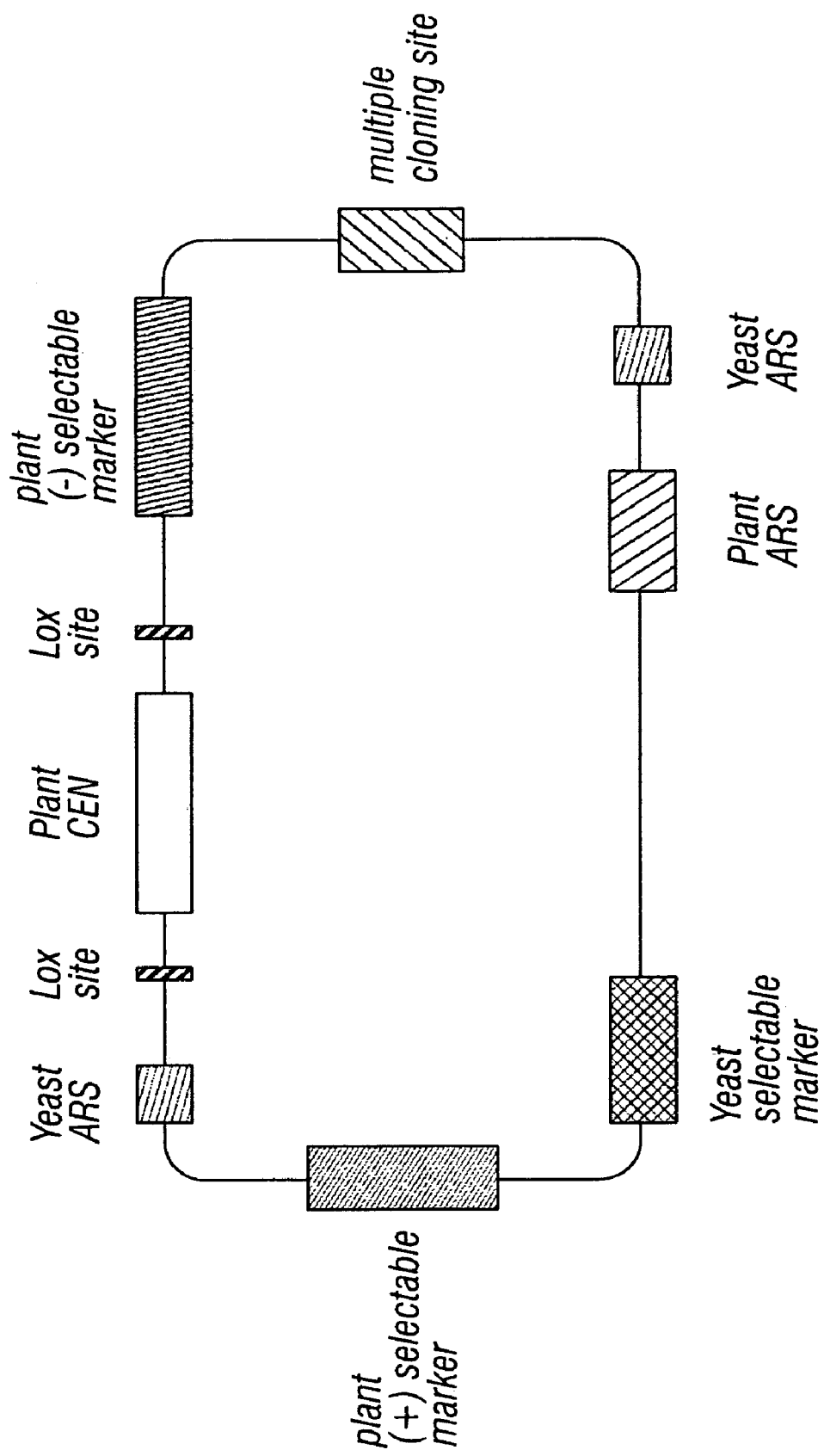
Figure 7L:
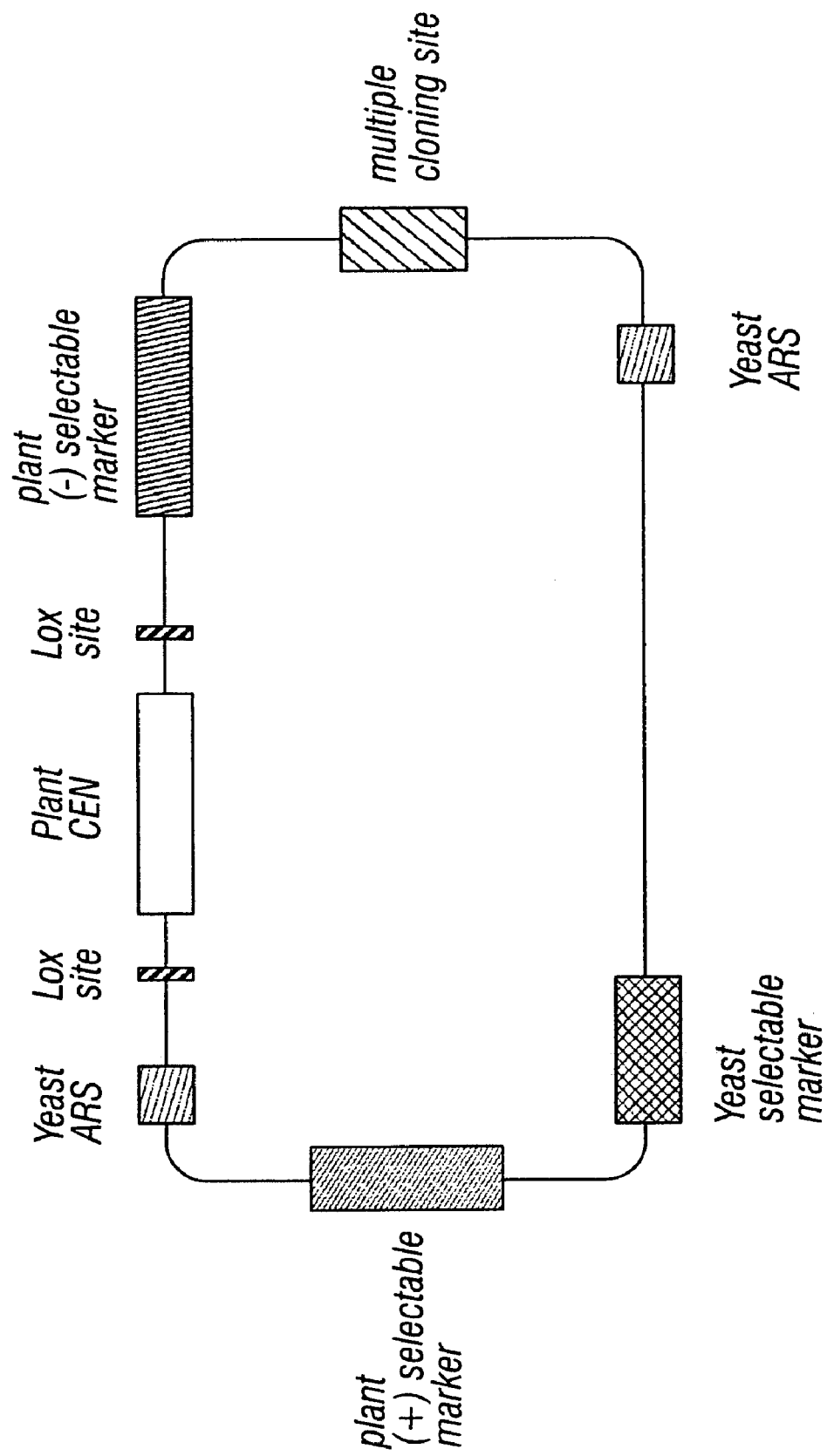
Figure 7M:
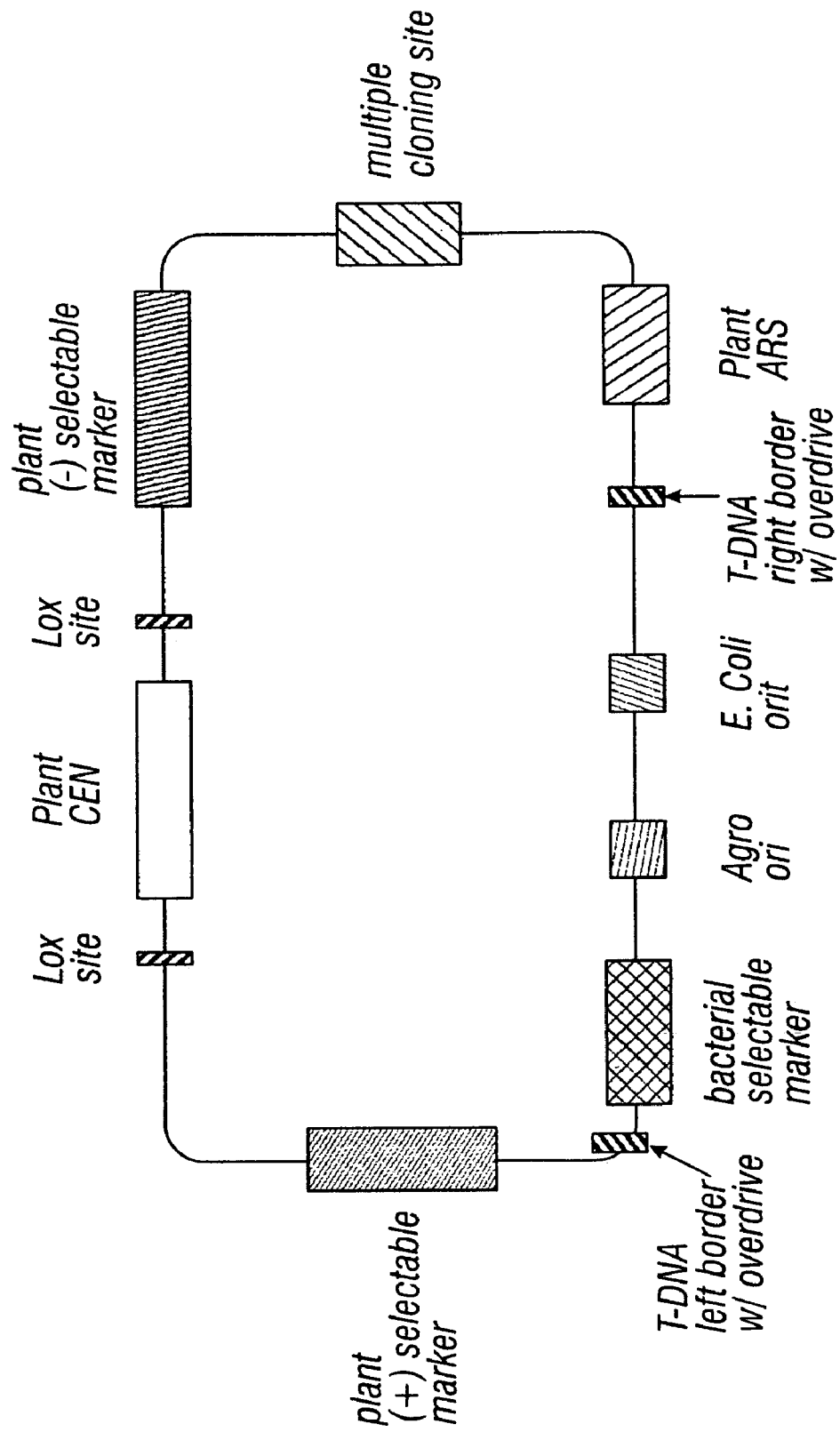
Figure 7N:
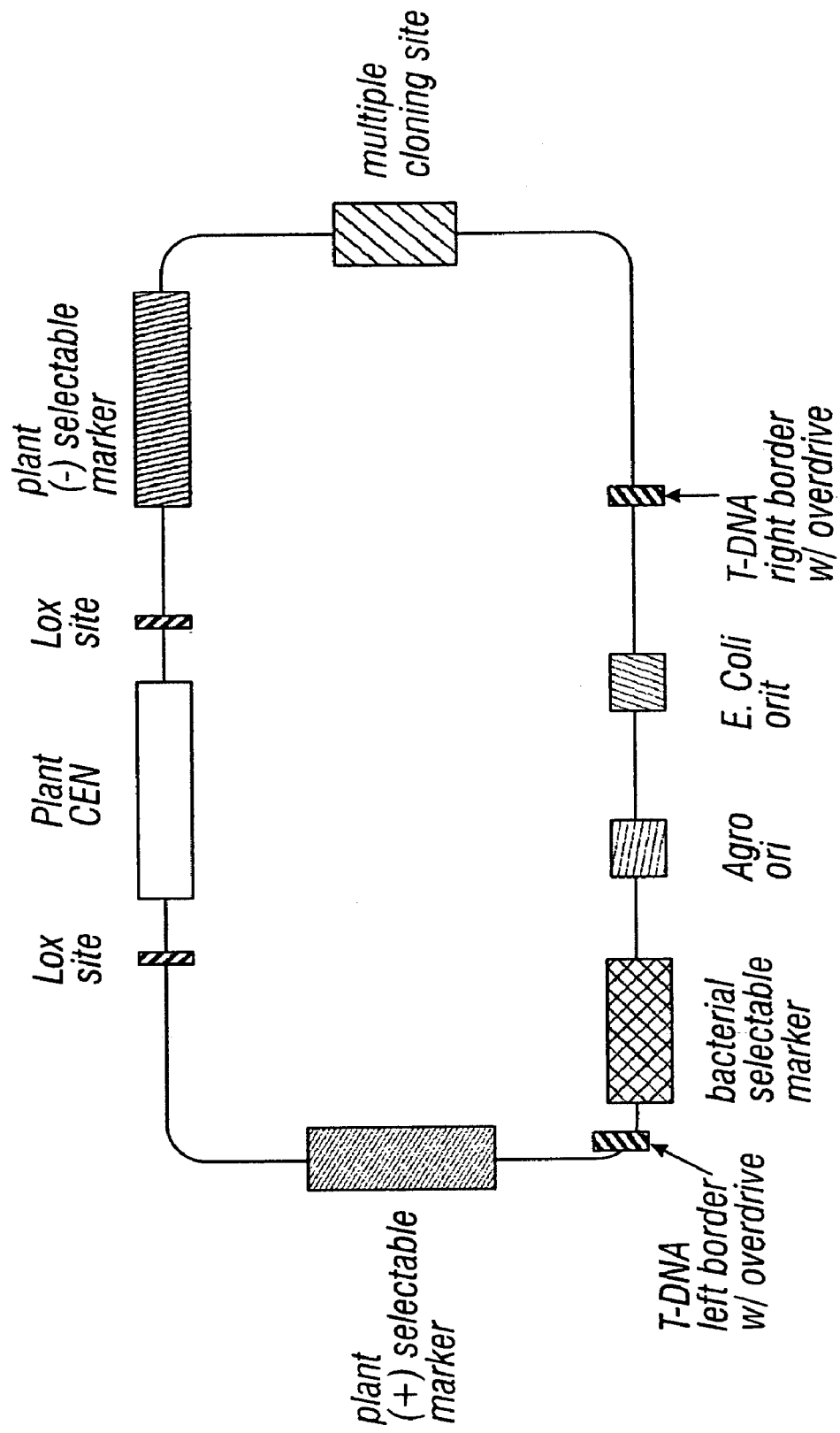

FIGS. 7A–7N. Exemplary Minichromosome vectors: The vectors shown in FIG. 7A, FIG. 7B, FIG. 7E, FIG. 7F, FIG. 7I and FIG. 7J have an *E. coli* origin of replication which can be high copy number, low copy number or single copy. In FIGS. 7A–7N, the vectors include a multiple cloning site which can contain recognition sequences for conventional restriction endonucleases with 4–8 bp specificity as well as recognition sequences for very rare cutting enzymes such as, for example, I-Ppo I, I-Cue I, PI-Tli, PI-Psp I, Not I, and PI Sce I. In FIG. 7A–7N, the centromere is flanked by Lox sites which can act as targets for the site specific recombinase Cre. FIG. 7A. Shows an *E. coli* plant circular shuttle vector with a plant ARS. FIG. 7B. Shows a plant circular vector without a plant ARS. The vector relies on a plant origin of replication function found in other DNA sequences such as selectable or screenable markers. FIG. 7C. Shows a yeast-plant circular shuttle vector with a plant ARS. The yeast ARS is included twice, once on either side of multiple cloning site to ensure that large inserts are stable. FIG. 7D. Shows a yeast-plant circular shuttle vector without a plant ARS. The vector relies on a plant origin of replication function found in other plant DNA sequences such as selectable markers. The yeast ARS is included twice, once on either side of the multiple cloning site to ensure that large inserts are stable. FIG. 7E. Shows an *E. coli-Agrobacterium*-plant circular shuttle vector with a plant ARS. Vir functions for T-DNA transfer would be provided in trans by a using the appropriate *Agrobacterium* strain. FIG. 7F. Shows an *E. coli-Agrobacterium*-plant circular shuttle vector without a plant ARS. The vector relies on a plant origin of replication function found in other plant DNA sequences such as selectable markers. Vir functions for T-DNA transfer would be provided in trans by a using the appropriate *Agrobacterium* strain. FIG. 7G. Shows a linear plant vector with a plant ARS. The linear vector could be assembled in vitro and then transferred into the plant by, for example, mechanical means such as micro projectile bombardment, electroporation, or PEG-mediated transformation. FIG. 7H. Shows a linear plant vector without a plant ARS. The linear vector could be assembled in vitro and then transferred into the plant by, for example, mechanical means such as micro projectile bombardment, electroporation, or PEG-mediated transformation. FIGS. 7I–7N. The figures are identical to FIGS. 7A–7F, respectively, with the exception that they do not contain plant telomeres. These vectors will remain circular once delivered into the plant cell and therefore do not require telomeres to stabilize their ends.

Figure 8A:
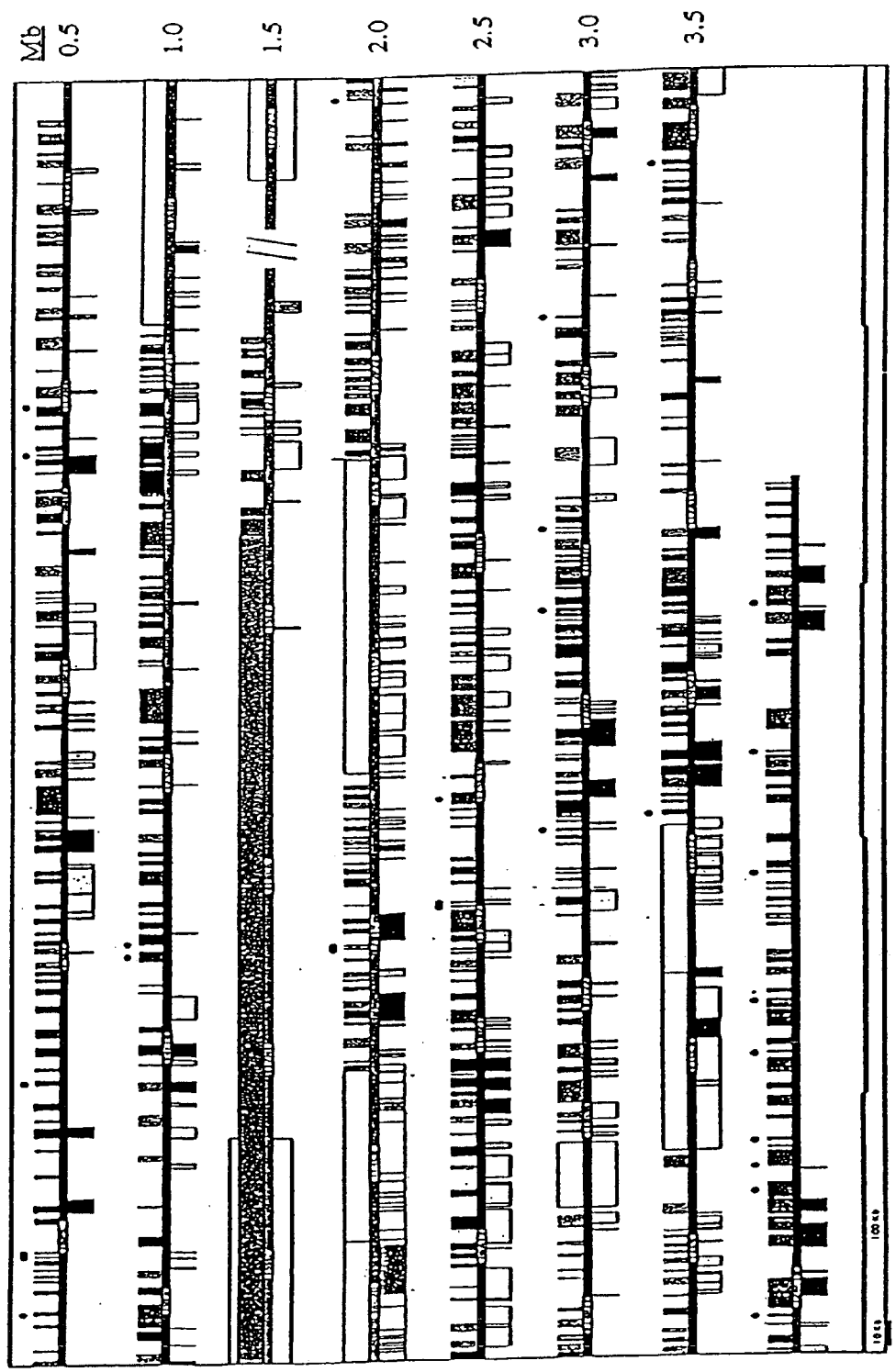
Figure 8B:
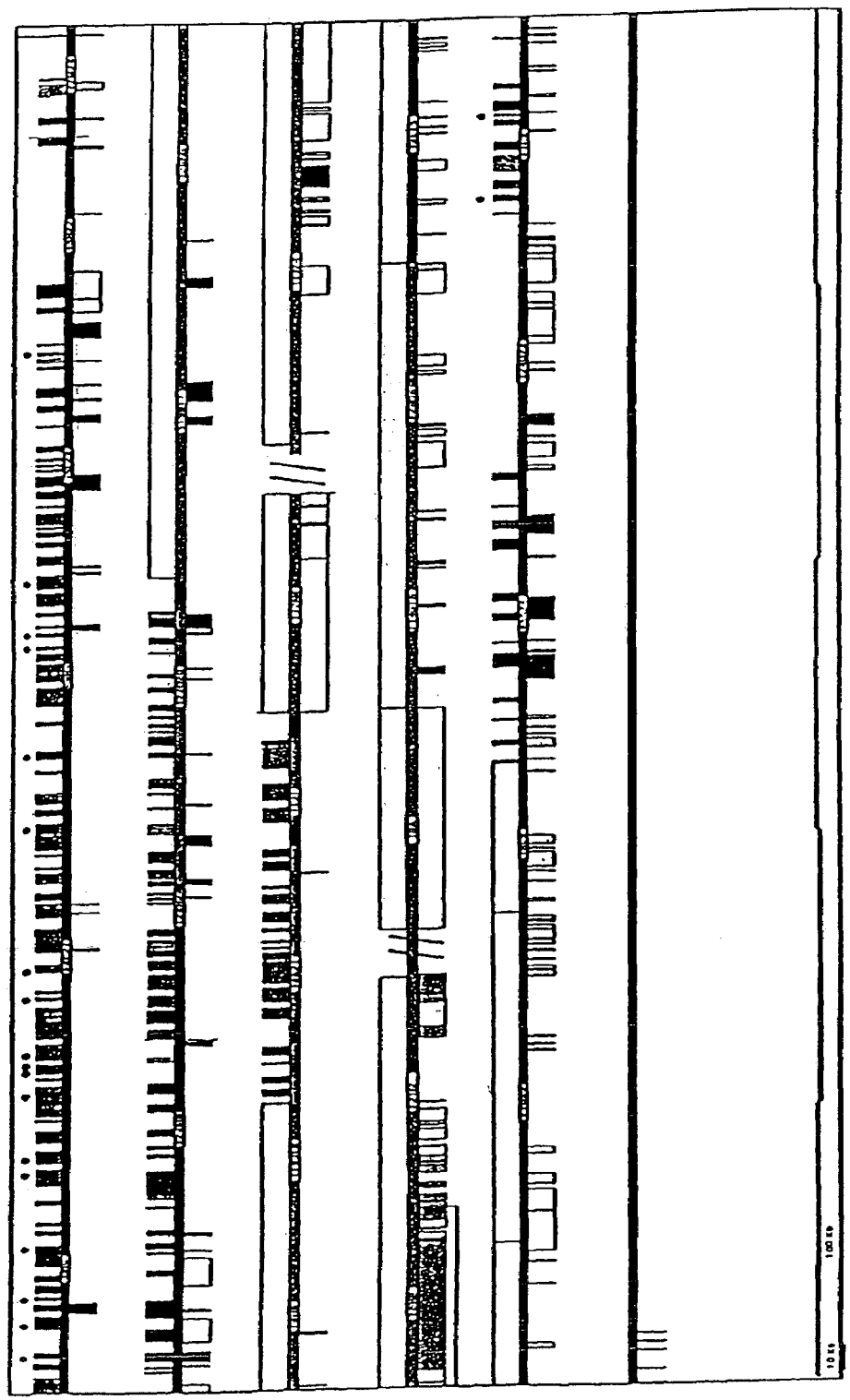

FIG. 8. Sequence features at *Arabidopsis* CEN2 (A) and CEN4 (B). Central bars depict annotated genomic sequence of indicated BAC clones; black, genetically-defined centromeres; white, regions flanking the centromeres. Sequences corresponding to genes and repetitive features, filled boxes (above and below the bars, respectively), are defined as in FIGS. 11A–T; predicted nonmobile genes, red; genes carried by mobile elements, black; nonmobile pseudogenes, pink; pseudogenes carried by mobile elements, gray; retroelements, yellow; transposons, green; previously defined centromeric repeats, dark blue; 180 bp repeats, pale blue. Chromosome-specific centromere features include a large mitochondrial DNA insertion (orange; CEN2), and a novel array of tandem repeats (purple; CEN4). Gaps in the physical maps (///), unannotated regions (hatched boxes), and expressed genes (filled circles) are shown.

Figure 9:
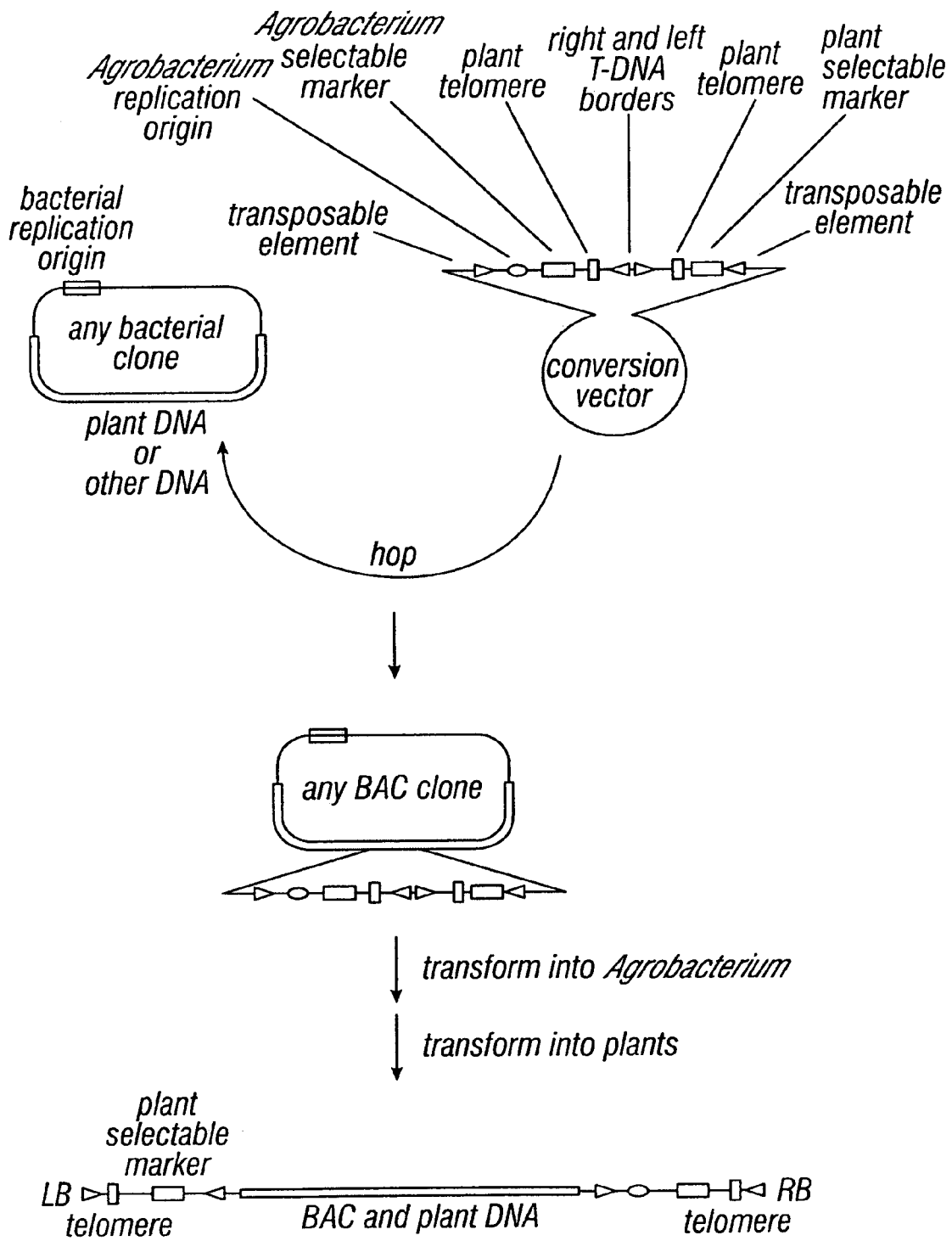

FIG. 9. Method for converting a BAC clone (or any other bacterial clone) into a minichromosome. A portion of the conversion vector will integrate into the BAC clone (or other bacterial clone of interest) either through non-homologous recombination (transposable element mediated) or by the action of a site specific recombinase system, such as Cre-Lox or FLP-FRT.

FIGS. 10A–G. Method for converting a BAC clone (or any other bacterial clone) into a minichromosome. The necessary selectable markers and origins of replication for propagation of genetic material in *E. coli, Agrobacterium* and *Arabidopsis* as well as the necessary genetic loci for *Agrobacterium* mediated transformation into *Arabidopsis* are cloned into a conversion vector. Using Cre/loxP recombination, the conversion vectors are recombined into BACs containing centromere fragments to form minichromosomes.

FIGS. 11A–T. Properties of centromeric regions on chromosomes II and IV of *Arabidopsis*. (Top) Drawing of genetically-defined centromeres (gray shading, CEN2, left; CEN4, right), adjacent pericentromeric DNA, and a distal segment of each chromosome, scaled in Mb as determined by DNA sequencing (gaps in the grey shading correspond to gaps in the physical maps). Positions in cM on the RI map (RI Map Data at the NACS: The European *Arabidopsis* Stock Centre) and physical distances in Mb, beginning at the northern telomere and at the centromeric gap, are shown. (Bottom) The density of each feature (FIGS. 11A–11T) is plotted relative to the position on the chromosome in Mb. (FIG. 11A, 11K) cM positions for markers on the RI map (solid squares) and a curve representing the genomic average of 1 cM/221 kb (dashed line). A single crossover within CEN4 in the RI mapping population RI Map Data at the NACS: The European *Arabidopsis* Stock Centre; Somerville and Somerville, 1999) may reflect a difference between male meiotic recombination monitored here and recombination in female meiosis. (FIGS. 11B–11E and FIGS. 11L–11O) The % of DNA occupied by repetitive elements was calculated for a 100 kb window with a sliding interval of 10 kb. (FIGS. 11B, 11L) 180 bp repeats; (FIGS. 12C, 12M) sequences with similarity to retroelements, including del, Ta1, Ta11, copia, Athila, LINE, Ty3, TSCL, 106B (Athila-like), Tat1, LTRs and Cinful; (FIGS. 11D, 11N) sequences with similarity to transposons, including Tag1, En/Spm, Ac/Ds, Tam1 MuDR, Limpet, MITES and Mariner; (FIGS. 11E, 11O) previously described centromeric repeats including 163A, 164A, 164B, 278A, 11B7RE, mi167, pAT27, 160-, 180- and 500-bp repeats, and telomeric sequences. (FIGS. 11F, 11P) % adenosine+thymidine was calculated for a 50 kb window with a sliding interval of 25 kb (FIGS. 11G–11J, 11Q–11T). The number of predicted genes or pseudogenes was plotted over a window of 100 kb with a sliding interval of 10 kb. (FIGS. 11G, 11I, 11Q, 11S) predicted genes (FIGS. 11G, 11Q) and pseudogenes (FIGS. 11I, 11S) typically not found on mobile DNA elements; (FIGS. 11H, 11J, 11R, 11T) predicted genes (FIGS. 11H, 11R) and pseudogenes (FIGS. 11J, 11T) often carried on mobile DNA, including reverse transcriptase, transposase, and retroviral polyproteins. Dashed lines indicate regions in which sequencing or annotation is in progress, annotation was obtained from GenBank records (National Center for Biotechnology Information Web Site), from the AGAD database (TIGR: The Institute of Genomic Research Web Site), and by BLAST comparisons to the database of repetitive *Arabidopsis* sequences (Cold Spring Harbor Laboratory Web Site); though updates to annotation records may change individual entries, the overall structure of the region will not be significantly altered.

Figure 12:
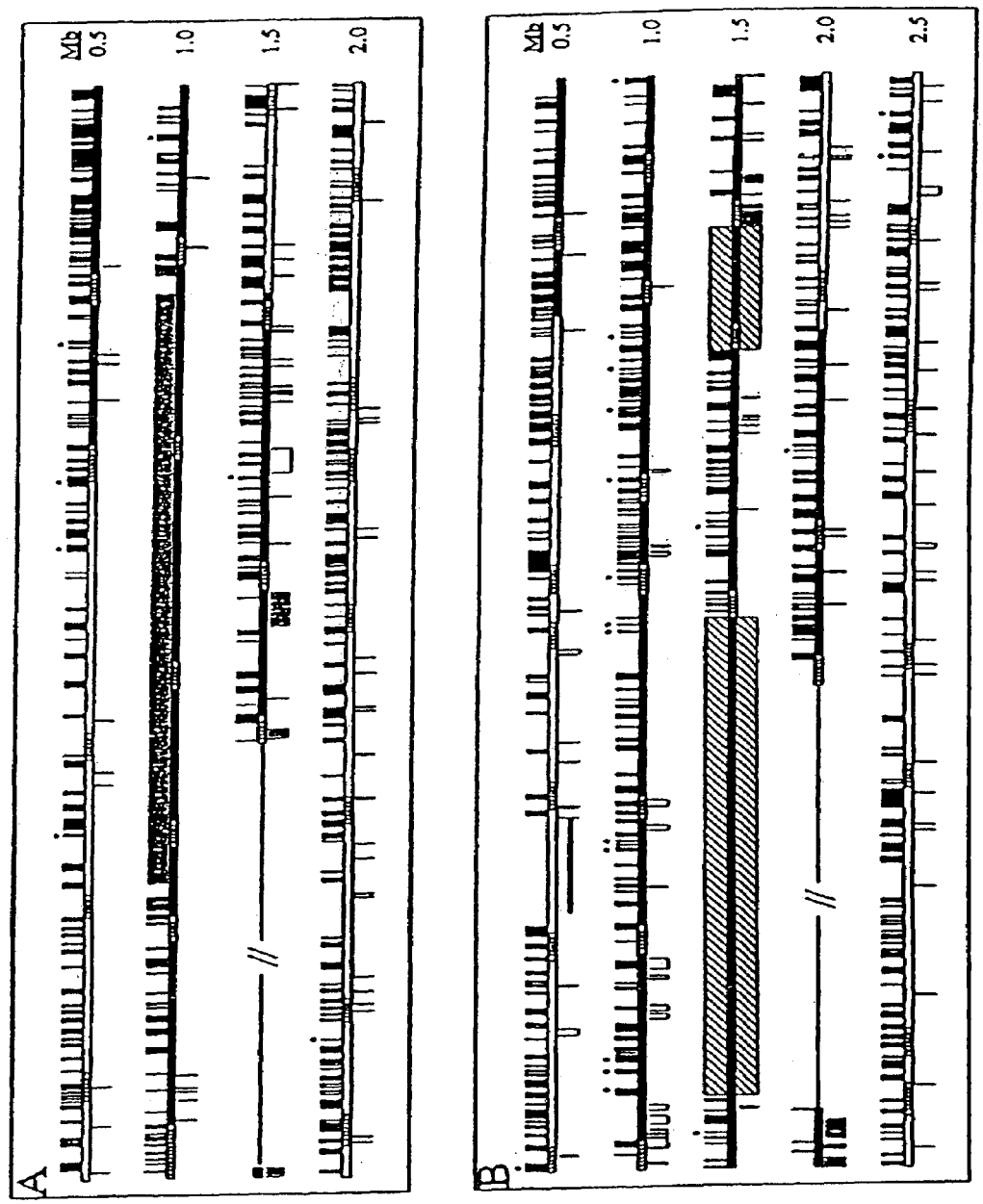

FIG. 12. Methods for converting a BAC clone containing centromere DNA into a minichromosome for introduction into plant cells. The specific elements described are provided for exemplary purposes and are not limiting. A) diagram of the BAC clone, noting the position of the centromere DNA, a site-specific recombination site (for example, lox P), and the F origin of replication. B) Conversion vector containing selectable and color markers (for example, 35S-Bar, nptII, LAT52-GUS, Scarecrow-GFP), telomeres, a site-specific recombination site (for example, lox P), antibiotic resistance markers (for example, amp or spc/str), *Agrobacterium* T-DNA borders (Agro Left and Right) and origin of replication (RiA4). C) The product of site specific recombination with the Cre recombinase at the lox P sites yields a circular product with centromeric DNA and markers flanked by telomeres. D) Minichromosome immediately after transformation into plants; subsequently, the left and right borders will likely be removed by the plant cell and additional telomeric sequence added by the plant telomerase.

Figure 13A:
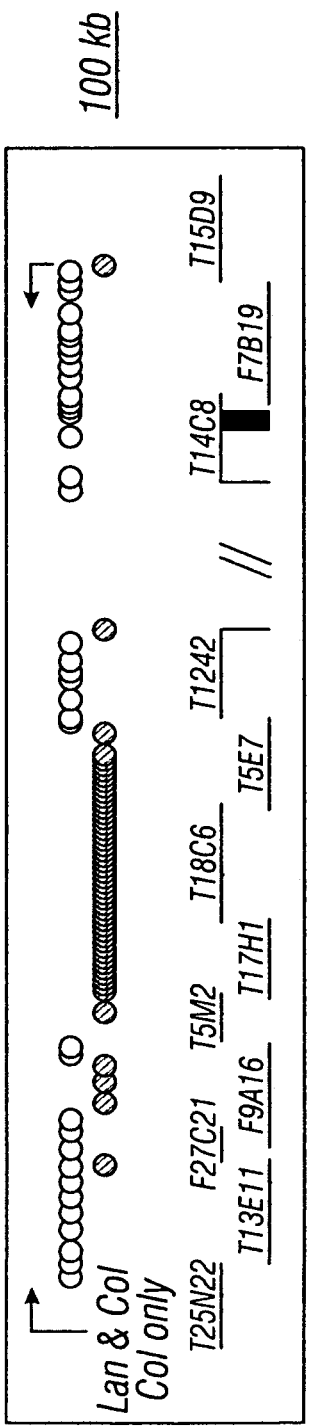
Figure 13B:
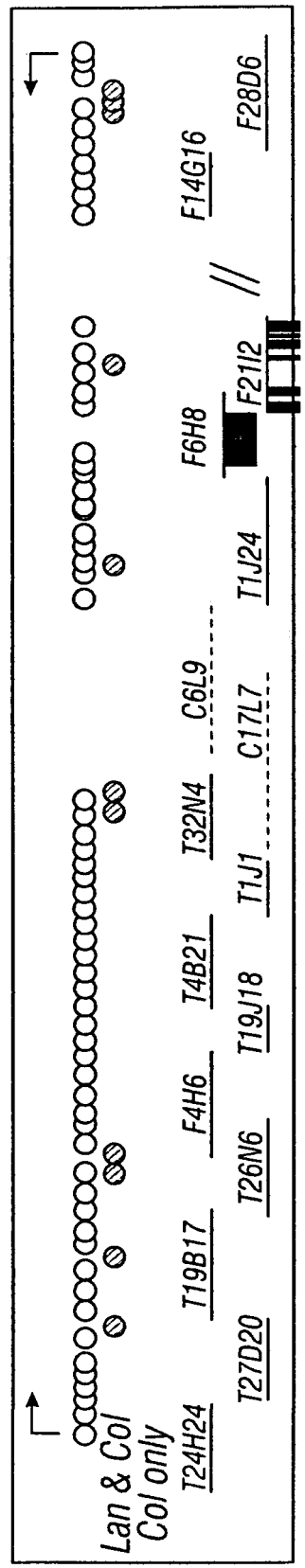

FIGS. 13A–B. Conservation of *Arabidopsis* centromere DNA. BAC clones (bars) used to sequence CEN2 (FIG. 13A) and CEN4 (FIG. 13B) are indicated; arrows denote the boundaries of the genetically-defined centromeres. PCR primer pairs yielding products from only Columbia (filled circles) or from both Landsberg and Columbia (open circles); BACs encoding DNA with homology to the mitochondrial genome (gray bars); 180 bp repeats (gray boxes); unsequenced DNA (dashed lines); and gaps in the physical map (double slashes) are shown.

FIGS. 14A–B. Primers used to analyze conservation of centromere sequences in the *A. thaliana* Columbia and Landsberg ecotypes. FIG. 14A: Primers used for amplification of chromosome 2 sequences. FIG. 14B: Primers used for amplification of chromosome 4 sequences.

Figure 15:
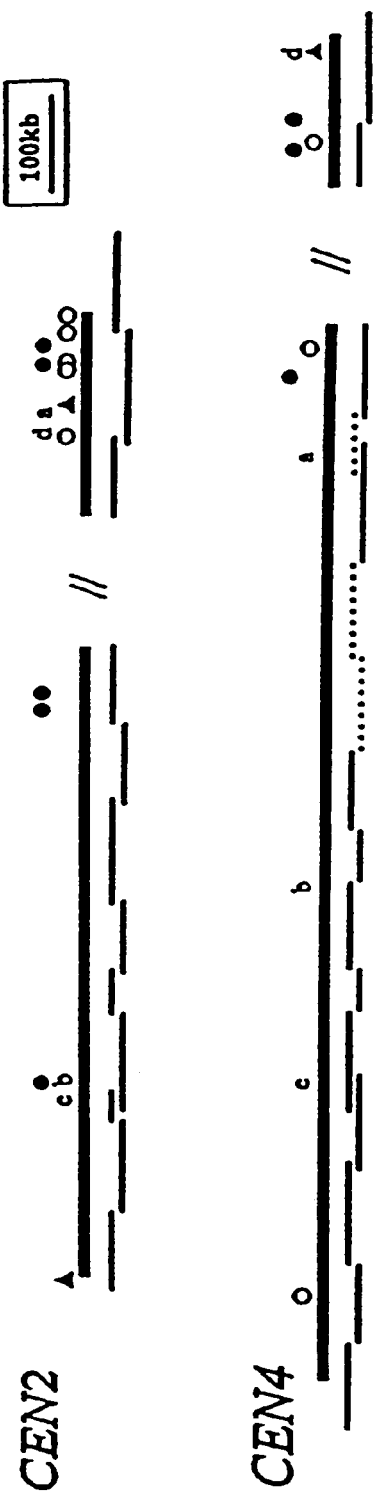

FIG. 15. Sequences common to *Arabidopsis* CEN2 and CEN4. Genetically-defined centromeres (bold lines), sequenced (thin lines), and unannotated (dashed lines) BAC clones are displayed as in FIGS. 14A, B. Repeats AtCCS1 (*A. thaliana* centromere conserved sequence) and AtCCS2 (closed and open circles, respectively), AtCCS3 (triangles), and AtCCS4–7 (4–7, respectively) are indicated (GenBank Accession numbers AF204874 to AF204880), and were identified using BLAST 2.0 (National Center for Biotechnology Information Web Site).

DETAILED DESCRIPTION OF THE INVENTION

The inventors have overcome the deficiencies in the prior art by providing the nucleic acid sequences of plant centromeres. The significance of this achievement relative to the prior art is exemplified by the general lack of detailed information in the art regarding the centromeres of multicellular organisms in general. To date, the most extensive and reliable characterization of centromere sequences has come from studies of lower eukaryotes such as *S. cerevisiae* and *S. pombe*, where the ability to analyze centromere functions has provided a clear picture of the desired DNA sequences. The *S. cerevisiae* centromere consists of three essential regions, CDEI, CDEII, and CDEIII, totaling only 125 bp, or approximately 0.006 to 0.06% of each yeast chromosome (Carbon et al., 1990; Bloom 1993). *S. pombe* centromeres are between 40 and 100 kB in length and consist of repetitive elements that comprise 1 to 3% of each chromosome (Baum et al., 1994). Subsequent studies, using tetrad analysis to follow the segregation of artificial chromosomes, demonstrated that less than ⅕ of the naturally occurring *S. pombe* centromere is sufficient for centromere function (Baum et al., 1994).

In contrast, the centromeres of mammals and other higher eukaryotes are less understood. Although DNA fragments that hybridize to centromeric regions in higher eukaryotes have been identified, in many cases, little is known regarding the functionality of these sequences (see Tyler-Smith et al., 1993). Centromere repeats often correlate with centromere location, with probes to the repeats mapping both cytologically and genetically to centromere regions. Many of these sequences are tandemly-repeated satellite elements and dispersed repeated sequences in arrays ranging from 300 kB to 5000 kB in length (Willard 1990). To date, only one of these repeats, a 171 bp element known as the alphoid satellite, has been shown by in situ hybridization to be present at each human centromere (Tyler-Smith et al., 1993). Whether repeats themselves represent functional centromeres remains controversial, as other genomic DNA can be required to confer efficient inheritance upon a region of DNA (Willard, 1997). Alternatively, the positions of some higher eukaryotic centromeres have been estimated by analyzing the segregation of chromosome fragments. This approach is imprecise, however, because a limited set of fragments can be obtained, and because normal centromere function is influenced by surrounding chromosomal sequences (for example, see Koornneef, 1983; FIG. 2).

A more precise method for mapping centromeres that can be used in intact chromosomes is tetrad analysis (Mortimer et al., 1981), which provides a functional definition of a centromere in its native chromosomal context. Centromeres that have been mapped in this manner include those from the yeasts *Saccharomyces cerevisiae, Schizosaccharomyces pombe*, and *Kluyveromyces lactis* (Carbon et al., 1990; Hegemann et al., 1993). In many of these systems, accurate mapping of the centromeres made it possible to clone centromeric DNA, using a chromosome walking strategy (Clarke et al., 1980). Subsequently, artificial chromosome assays were used to define more precisely the centromere sequences (Hegemann et al., 1993; Baum et al., 1994).

Attempts to develop a reliable centromeric assay in mammals have yielded ambiguous results. For example, Hadlaczky et al., (1991) identified a 14 kB human fragment that can, at low frequency, result in de novo centromere formation in a mouse cell line. In situ hybridization studies, however, have shown that this fragment is absent from naturally occurring centromeres, calling into question the reliability of this approach for testing centromere function (Tyler-Smith et al., 1993). Similarly, transfection of alphoid satellites into cell lines results in the formation of new chromosomes, yet some of these chromosomes also required host sequences that could contribute centromere activity (Haaf et al., 1992; Willard, 1997). Further, the novel chromosomes can have alphoid DNA spread throughout their length yet have only a single centromeric constriction, indicating that a block of alphoid DNA alone may be insufficient for centromere function (Tyler-Smith et al., 1993).

Although plant centromeres can be visualized easily in condensed chromosomes, they have not been characterized as extensively as centromeres from yeast or mammals. Genetic characterization has relied on segregation analysis of chromosome fragments, and in particular on analysis of trisomic strains that carry a genetically marked, telocentric fragment (for example, see Koornneef 1983). In addition, repetitive elements have been identified that are either genetically (Richards et al., 1991) or physically (Alfenito et al., 1993; Maluszynska et al., 1991) linked to a centromere. In no case, however, has the functional significance of these sequences been tested.

Cytology in *Arabidopsis thaliana* has served to correlate centromere structure with repeat sequences. A fluorescent dye, DAPI, allows visualization of centromeric chromatin domains in metaphase chromosomes. A fluorescence in situ hybridization (FISH) probe based on 180 bp pAL1 repeat sequences colocalized with the DAPI signature near the centromeres of all five *Arabidopsis* chromosomes (Maluszynska et al., 1991; Martinez-Zapater et al., 1986). Although a functional role for pAL1 has been proposed, more recent studies have failed to detect this sequence near the centromeres in species closely related to *Arabidopsis thaliana* (Maluszynska et al., 1993). These results are particularly troubling because one of the species tested, *A. pumila*, is thought to be an amphidiploid, derived from a cross between *A. thaliana* and another close relative (Maluszynska et al., 1991; Price et al., 1995). Another repetitive sequence, pAtT12, has been genetically mapped to within 5 cM of the centromere on chromosome 1 and to the central region of chromosome 5 (Richards et al., 1991), although its presence on other chromosomes has not been established. Like pAL1, a role for pAtT12 in centromere function remains to be demonstrated.

Due to the fact that kinetochores constitute a necessary link between centromeric DNA and the spindle apparatus, the proteins that are associated with these structures recently have been the focus of intense investigation (Bloom 1993; Earnshaw 1991). Human autoantibodies that bind specifically in the vicinity of the centromere have facilitated the cloning of centromere-associated proteins (CENPs, Rattner 1991), and at least one of these proteins belongs to the kinesin superfamily of microtubule-based motors (Yen 1991). Yeast centromere-binding proteins also have been identified, both through genetic and biochemical studies (Bloom 1993; Lechner et al., 1991).

The centromeres of *Arabidopsis thaliana* have been mapped using trisomic strains, where the segregation of chromosome fragments (Koornneef 1983) or whole chromosomes (Sears et al., 1970) was used to localize four of the centromeres to within 5, 12, 17 and 38 cM, respectively. These positions have not been refined by more recent studies because the method is limited the difficulty of obtaining viable trisomic strains (Koornneef 1983). These factors introduce significant error into the calculated position of the centromere, and in *Arabidopsis*, where 1 cM corresponds roughly to 200 kB (Koornneef 1987; Hwang et al., 1991), this method did not map any of the centromeres with sufficient precision to make chromosome walking strategies practical. Mapping of the *Arabidopsis* genome was also discussed by (Hauge et al., 1991).

I. Isolation of Centromere Clones

The present invention relates to methods of isolating and identifying centromere DNA sequences from total genomic DNA of an organism without genetic mapping of the organism. Centromere DNA can be purified from total genomic DNA using several methods which include: 1) digesting genomic DNA with restriction enzymes and separating the fragments on agarose gels, to reveal major classes of repetitive DNA; 2) digesting genomic DNA with restriction enzymes sensitive to DNA methylation and separating the fragments on agarose gels to reveal the heavily methylated fraction of the genome; and 3) collecting the rapidly annealing fraction of denatured genomic DNA. These three methods isolate centromere DNA; therefore, these methods are expected to independently isolate the same sequences, thus validating the sequences' centromere origin. It is anticipated that each of these methods can be applied to genomic DNA from any organism, including some lower organisms such as yeasts, as well as higher organisms such as plants and animals. Each of these methods is described in detail below.

1. Isolation of Repetitive DNA

Centromere regions often contain many copies of the same DNA sequence (repetitive DNA); such repeats can range in size from a few nucleotides long to hundreds or thousands of bases. Such repetitive DNA can be identified following digestion of genomic DNA with restriction endonucleases. Digestion of non-repetitive genomic DNA with a particular restriction enzyme produces a distribution of size fragments; in contrast, digestion of repeats with a restriction enzyme that cuts within each repeat produces a fragment of a typical size. Thus, genomic DNA that has been cut with a restriction enzyme can be size fractionated by agarose gel electrophoresis to reveal repetitive DNA elements; after staining the gel to reveal the DNA, the repetitive fragment can be excised and purified using conventional techniques or commercial kits. Such repeats can be introduced into cloning vectors and characterized as described below. By using this method with a variety of restriction enzymes, different repetitive elements can be purified from genomic DNA.

2. Purification of Methylated DNA

This method is disclosed in detail in co-pending U.S. patent application Ser. No. 09/888,220, filed Jun. 22, 2001, the disclosure of which is incorporated herein by reference in its entirety and made a part hereof. Plant centromere DNA is often extensively modified by methylation; the presence of this methylation can be used to purify centromere fragments. Digestion of genomic DNA with a methylation-sensitive restriction endonuclease (for example Sau3A or HpaII) yields a range of fragment sizes; endonuclease sites that are methylated are protected from digestion. Heavily methylated DNA molecules, such as centromere DNA, yield large fragments after digestion and can therefore be separated from the lightly or non-methylated fraction by virtue of their size. For example agarose gel electrophoresis, acrylamide gel electrophoresis, sucrose gradient fractionation, or other size fractionation techniques can be used to separate these fragments into pools of "large" (7–12 kb) and "smaller" fragments (3–7 kb and 0–3 kb).

3. Isolation of Rapidly Annealing DNA.

The rapidity with which denatured single stranded DNA can reanneal with another single stranded DNA molecule of complementary sequence upon renaturation is dependant upon its abundance. Therefore when genomic DNA is denatured and allowed to renature, the repetitive fraction of the genome, including centromere DNA, will renature before the unique and low copy fractions of the genome. Thus by fragmenting purified genomic DNA, denaturing it, collecting fractions at specific time points (such as 2, 4, 6, 8, and 10 minutes) during renaturation and treating those fractions to remove unannealed DNA it is possible to purify repetitive DNA from total genomic DNA. Several methods can be used to remove unannealed from annealed DNA including treatment of the sample with an enzyme, such as S1 nuclease, that degrades single-stranded DNA or exposure to an agent that binds single-stranded DNA such as hydroxylapatite. By varying the time at which fractions are collected during renaturation it is possible to separate DNA fragments into highly repetitive, moderately repetitive, and non-repetitive fractions.

II. Cloning and Sequencing Small Fragments of Centromere DNA

Repetitive or methylated DNA fragments isolated using the methods described above can be ligated (using T4 DNA ligase, for example) to a plasmid vector and cloned by transformation into E. coli. These clones can then propagated, sequenced, used to assemble minichromosomes, or used to identify larger centromere clones, generate molecular markers that facilitate genetic mapping of centromeres, or create probes for chromosome mapping experiments such as fluorescent in situ hybridization (FISH).

III. Identifying Centromere Clones in Genomic Libraries

A genomic library can be screened for clones carrying centromere DNA by arraying the clones onto solid supports, such as membrane filters, and probing with labeled fragments of purified centromere DNA, including cloned repetitive or methylated DNA fragments described above, or alternatively, the entire set of rapidly annealing genomic DNA or highly methylated genomic DNA fragments. Probes can be used singly or in combination. Typically these probes are labeled by incorporation of radionucleotides, fluorescent nucleotides, or other chemical or enzymatic ligands that enable easy detection. The labeled probe DNA is denatured and hybridized to the arrayed library using standard molecular biology techniques. Hybridization is performed at a temperature that will discourage non-specific DNA annealing while promoting the hybridization of the labeled probe to complementary sequences. After incubation, the arrayed library is washed to remove unannealed probe, and a detection method appropriate to the label incorporated in the probe is used. For example, if the probe is radiolabeled, the labeled filter is exposed to X-ray film.

To identify centromere clones, the results of several hybridization experiments are quantitated and compared. In some cases, centromere clones may hybridize to only one probe; in other cases, the clones will hybridize to multiple probes. The hybridization intensity of each clone to each probe can be measured and stored in a database. A preferred method for this analysis is to use software that digitizes the hybridization signals, assigns each signal to its corresponding clone address, ensures that duplicate copies of the clones successfully hybridized, and enters the resulting information into a relational database (MySQL for example). Another possible method for this analysis is to examine the hybridization results visually, estimate the hybridization intensity, and tabulate the resulting information.

The results of each hybridization experiment can be classified by grouping clones that show hybridization to each probe above a threshold value. For example, a computerized relational database can be queried for clones giving hybridization signals above a certain threshold for individual probes or for multiple probes. Based on these hybridization patterns, clones can be grouped into categories, and representative members of each category can be tested in minichromosomes.

Accordingly, the centromere sequences of the current invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating centromeric DNA segments. Nucleic acid sequences hybridizing under these conditions and the conditions below to the nucleic acid sequences provided by the invention form a part of the invention. Detection of nucleic acid segments via hybridization is well-known to those of skill in the art, and the teachings of U.S. Pat. Nos. 4,965,188 and 5,176,995 (each specifically incorporated herein by reference in its entirety) are exemplary of the methods of hybridization analyses. Teachings such as those found in the texts of Maloy et al., 1991; Segal, 1976; Prokop, 1991; and Kuby. 1994 are particularly relevant.

IV. Identifying Centromere Sequences of an Organism from Genomic Sequence Datasets It is possible to devise computational algorithms to search databases of genomic sequences and select centromere sequences by identifying those with the characteristics of centromeres. For example, by selecting the most abundant tandem repeat of a particular size will yield centromere sequences. Other sets of characteristics could also be useful.

The following is an example of a computational algorithm designed to extract centromere sequences from genomic sequence datasets. It is important to note that this algorithm examines primary sequence data and does not rely on prior annotation of the sequence. The algorithm consists of steps 1 through 10. However, not all the steps must occur in the listed order without altering the output. Other rearrangements are easily recognizable by one skilled in the art. The following terms are used in describing the algorithm. BLAST is Basic Local Alignment Search Tool, a family of freely available algorithms for sequence database searches. BLAST aligns two sequences and yields an estimate of the probability that this alignment is significant, i.e. that it did not occur by chance. The two sequences compared by BLAST are called the 'query', usually a single sequence of interest, and the 'subject', often part of a large database of sequences that are compared to the query. The query sequence (query) can also be part of a database of sequences. The outputs of BLAST are High Scoring Pairs (HSPs) that are alignments of subject and query sequences. Nucleotide position describes the position of a given nucleotide within the sequence, relative to the first nucleotide of the sequence. BLAST score (e value) is the likelihood that a given sequence alignment is significant (the lower the value the higher the significance). The algorithm is as follows:

(1) provide a first dataset consisting of the genomic sequences, or a representative fraction of genomic sequence, of the organism of interest;

(2) identify and eliminate known non-centromeric repeat sequences from the first dataset by using the BLAST sequence comparison algorithm to create a second dataset;

(3) compare each sequence in the second dataset to itself by using the BLAST sequence comparison algorithm, obtain a BLAST score for each pair of sequence compared, and collect high score pairs to create a third dataset;

(4) examine the BLAST score of each high score pair in the third dataset and eliminate the pairs having a score greater than $10^{-20}$ to create a fourth dataset;

(5) eliminate the high score pairs in the fourth dataset having less than 80 bp or more than 250 bp to create a fifth dataset;

(6) examine the nucleotide position of each high score pair in the fifth dataset and eliminate pairs having 100% identity and identical nucleotide positions (i.e. self matches) to create a sixth dataset;

(7) examine the nucleotide position of each high score pair in the sixth dataset and eliminate pairs having opposite orientation of the nucleotides to create a seventh dataset;

(8) examine the nucleotide position of both sequences for each high score pair in the seventh dataset and eliminate sequences that are overlapping to create an eighth dataset; and (9) examine the nucleotide position of each sequence in the eighth dataset and eliminate sequences not having at least one neighboring sequence within 250 bp to create a ninth dataset; and

(10) compare each sequence in the ninth dataset to all other sequences in the ninth dataset by using the BLAST sequence comparison algorithm and select the most common sequence as a centromere sequence of the organism.

Optimally, the databset used in step (1) in the above algorithm would be the whole genome dataset such as the *Arabidopsis* genome which was derived by methodical sequencing of mapped clones or the rice genome dataset which was derived by shotgun sequencing. Alternatively, the algorithm would also work well on representative genome datasets. By the term "representative genome datasets", it is meant that the genomic sequences in the dataset is a subset of the sequences of the whole genome collected from the whole genome without bias, such as bias toward coding sequences. These sequences would be representative of the genome as a whole. For example, the use of a 0.5× or even a 0.1× library of *Arabidposis* with representative genome datasets would return a true positive result. On the contrary, the use of a subset of genomic sequences of the whole genome which are not representative of the whole genome and biased toward certain sequences, such as the coding sequence, would return false positive results.

V. Centromere Compositions

The present invention concerns nucleic acid segments, isolatable from various plant cells, that are enriched relative to total genomic DNA, or isolated from other sources or chemically synthesized with a novel sequence, or other nucleic acids that are capable of conferring centromere activity to a recombinant molecule when incorporated into the host cell. As used herein, the term "nucleic acid segment" refers to a nucleic acid molecule that has been purified from total genomic nucleic acids of a particular species. Therefore, a nucleic acid segment conferring centromere function refers to a nucleic acid segment that contains centromere sequences yet is isolated away from, or purified free from, total genomic nucleic acids. Included within the term "nucleic acid segment", are nucleic acid segments and smaller fragments of such segments, and also recombinant vectors, including, for example, minichromosomes, artificial chromosomes, BACs, YACs, plasmids, cosmids, phage, viruses, and the like.

Similarly, a nucleic acid segment comprising an isolated or purified centromeric sequence refers to a nucleic acid segment including centromere sequences and, in certain aspects, regulatory sequences, isolated substantially away from other naturally occurring sequences, or other nucleic acid sequences. In this respect, the term "gene" is used for simplicity to refer to a protein, polypeptide- or peptide-encoding unit. As will be understood by those in the art, this functional term includes both genomic sequences, cDNA sequences and smaller engineered gene segments that may express, or may be adapted to express, proteins, polypeptides or peptides.

"Isolated substantially away from other sequences" means that the sequences of interest, in this case centromere sequences, are included within the genomic nucleic acid clones provided herein. Of course, this refers to the nucleic acid segment as originally isolated, and does not exclude all genes or coding regions.

In particular embodiments, the invention concerns isolated nucleic acid segments and recombinant vectors incorporating nucleic acid sequences that encode a centromere functional sequence that includes a contiguous sequence from the centromeres of the current invention. Again, nucleic acid segments that exhibit centromere function activity will be most preferred.

In still yet another aspect, the invention provides a plant centromere which is further defined as an *Arabidopsis thaliana* centromere. In yet another embodiment of the invention, the plant centromere comprises an *Arabidopsis thaliana* chromosome 2 centromere. The chromosome 2 centromere may comprise, for example, from about 100 to about 611,000, about 500 to about 611,000, about 1,000 to about 611,000, about 10,000 to about 611,000, about 20,000 to about 611,000, about 40,000 to about 611,000, about 80,000 to about 611,000, about 150,000 to about 611,000, or about 300,000 to about 611,000 contiguous nucleotides of a first nucleic acid sequence flanking a first series of 180 bp repeats in centromere 2 of *A. thaliana*. The centromere may also be defined as comprising from about 100 to about 50,959, about 500 to about 50,959, about 1,000 to about 50,959, about 5,000 to about 50,959, about 10,000 to about 50,959, 20,000 to about 50,959, about 30,000 to about 50,959, or about 40,000 to about 50,959 contiguous nucleotides of a second nucleic acid sequence flanking a second series of 180 bp repeats in centromere 2 of *A. thaliana*. The centromere may comprise sequences from both of the third and the fourth sequences, including the aforementioned fragments, or the entirety of these sequences. In particular embodiments, the inventors contemplate a 3' fragment of the first sequence can be fused to a 5' fragment of the second sequence, optionally including one or more 180 bp repeat sequence disposed therebetween.

In still yet another aspect, the invention provides an *Arabidopsis thaliana* chromosome 4 centromere. In certain embodiments of the invention, the centromere may comprise from about 100 to about 1,082,000, about 500 to about 1,082,000, about 1,000 to about 1,082,000, about 5,000 to about 1,082,000, about 10,000 to about 1,082,000, about 50,000 to about 1,082,000, about 100,000 to about 1,082,000, about 200,000 to about 1,082,000, about 400,000 to about 1,082,000, or about 800,000 to about 1,082,000 contiguous nucleotides of a third nucleic acid sequence flanking a third series of repeated sequences, including comprising the nucleic acid sequence of the third sequence. The centromere may also be defined as comprising from about 100 to about 163,317, about 500 to about 163,317, about 1,000 to about 163,317, about 5,000 to about 163,317, about 10,000 to about 163,317, about 30,000 to about 163,317, about 50,000 to about 163,317, about 80,000 to about 163,317, or about 120,000 to about 163,317 contiguous nucleotides of the nucleic acid sequence of a fourth sequence flanking a fourth series of repeated sequences, and may be defined as comprising the nucleic acid sequence of the fourth sequence. The centromere may comprise sequences from both the third and the fourth sequences, including the aforementioned fragments, or the entirety of the third and the fourth sequences. In particular embodiments, the inventors contemplate a 3' fragment of the third sequence can be fused to a 5' fragment of the fourth sequence, optionally including one or more 180 bp repeat sequence disposed therebetween.

In yet another embodiment, there is provided a *Arabidopsis thaliana* chromosome 1, 3 or 5 centromere selected from the nucleic acid sequence given by one of the repeated sequences in these chromosomes, or fragments thereof. The length of the repeat used may vary, but will preferably range from about 20 bp to about 250 bp, from about 50 bp to about 225 bp, from about 75 bp to about 210 bp, from about 100 bp to about 205 bp, from about 125 bp to about 200 bp, from about 150 bp to about 195 bp, from about 160 bp to about 190 and from about 170 bp to about 185 bp including about 180 bp. In one embodiment, the construct comprises at least 100 base pairs, up to an including the full length, of one of the preceding sequences. In addition, the construct may include 1 or more 180 base pair repeats.

In one embodiment, the centromere n copies of a repeated nucleotide sequence obtained by the method disclosed herein, wherein n is at least 2. Potentially any number of repeat copies capable of physically being placed on the recombinant construct could be included on the construct, including about 5, 10, 15, 20, 30, 50, 75, 100, 150, 200, 300, 400, 500, 750, 1,000, 1,500, 2,000, 3,000, 5,000, 7,500, 10,000, 20,000, 30,000, 40,000, 50,000, 60,000, 70,000, 80,000, 90,000 and about 100,000, including all ranges in-between such copy numbers. Moreover, the copies, while largely identical, can vary from each other. Such repeat variation is commonly observed in naturally occurring centromeres.

In another embodiment, the centromere is a *Brassica oleracea* centromere comprising *Brassica oleracea* centromere DNA. In one embodiment, the *Brassica oleracea* centromere is defined as comprising n copies of a repeated nucleotide sequence, wherein n is at least 2. Potentially any number of repeat copies capable of physically being placed on the recombinant construct could be included on the construct, including about 5, 10, 15, 20, 30, 50, 75, 100, 150, 200, 300, 400, 500, 750, 1,000, 1,500, 2,000, 3,000, 5,000, 7,500, 10,000, 20,000, 30,000, 40,000, 50,000, 60,000, 70,000, 80,000, 90,000 and about 100,000, including all ranges in-between such copy numbers. In one embodiment, the repeated nucleotide sequence is isolated from *Brassica oleracea* given by SEQ ID NO:1, 2, 3, or 4.

In yet another embodiment, the centromere is a *Glycine max* centromere comprising *glycine max* centromere DNA. In an embodiment, the *Glycine max* centromere is defined as comprising n copies of a repeated nucleotide sequence, wherein n is at least 2. Potentially any number of repeat copies capable of physically being placed on the recombinant construct could be included on the construct, including about 5, 10, 15, 20, 30, 50, 75, 100, 150, 200, 300, 400, 500, 750, 1,000, 1,500, 2,000, 3,000, 5,000, 7,500, 10,000, 20,000, 30,000, 40,000, 50,000, 60,000, 70,000, 80,000, 90,000 and about 100,000, including all ranges in-between such copy numbers. In one embodiment, the repeated nucleotide sequence is isolated from *Glycine max* given by SEQ ID NO:5, 6, 7, or 8.

In yet another embodiment, the centromere is a *Lycopersicon esculentum* centromere comprising *Lycopersicon esculentum* centromere DNA. In an embodiment, the *Lycopersicon esculentum* centromere is defined as comprising n copies of a repeated nucleotide sequence, wherein n is at least 2. Potentially any number of repeat copies capable of physically being placed on the recombinant construct could be included on the construct, including about 5, 10, 15, 20, 30, 50, 75, 100, 150, 200, 300, 400, 500, 750, 1,000, 1,500, 2,000, 3,000, 5,000, 7,500, 10,000, 20,000, 30,000, 40,000, 50,000, 60,000, 70,000, 80,000, 90,000 and about 100,000, including all ranges in-between such copy numbers. In one embodiment, the repeated nucleotide sequence is isolated from *Lycopersicon esculentum* given by SEQ ID NO:9 or 10.

In yet another embodiment, the centromere is a *Zea mays* centromere comprising *Zea mays* centromere DNA. In an embodiment, the centromere is defined as comprising n copies of a repeated nucleotide sequence, wherein n is at least 2. Potentially any number of repeat copies capable of physically being placed on the recombinant construct could be included on the construct, including about 5, 10, 15, 20, 30, 50, 75, 100, 150, 200, 300, 400, 500, 750, 1,000, 1,500, 2,000, 3,000, 5,000, 7,500, 10,000, 20,000, 30,000, 40,000, 50,000, 60,000, 70,000, 80,000, 90,000 and about 100,000, including all ranges in-between such copy numbers. In one embodiment, the repeated nucleotide sequence is isolated from *Zea mays* given by SEQ ID NO:11, 12 or 13.

The centromere can additionally be defined as the region of the chromosome where the sister chromatids pair during cell division. The centromere is also the chromosomal region where the kinetochore (the chromosomal attachment structure for the spindle) and the spindle (the cellular machinery that provides the motive force for chromosome segregation) attach to the chromosome during mitosis and meiosis. The centromere is also defined as the region of the primary constriction in a condensed chromosome. The DNA of the centromere is characteristically heavily methylated, repetitive, and condensed (heterochromatic).

VI. Minichromosome Construction

Minichromosomes are constructed by combining fragments of centromere DNA with other DNA sequences useful for propagation of the resultant recombinant DNA molecule in *E. coli*, other bacteria, yeast or plants. Recombinant plasmids containing large fragments of centromere DNA are referred to as centromere clones. Centromere sequences removed from centromere clones, or centromere sequences derived directly from genomic DNA, are referred to as centromere fragments. Recombinant constructs containing DNA sequences necessary for the propagation, delivery, selection, and detection of minichromosomes will be referred to as minichromosome vector sequences or minichromosome vectors; these sequences can include but are not limited to selectable marker genes, visible marker genes, origins of replication, restriction endonuclease recognition sites, homing endonuclease recognition sites, sequences recognized by site specific recombinase enzymes, telomere sequences, and sequences required for delivery of minichromosomes into bacteria, yeast or plant cells. Recombinant constructs containing both large centromere fragments as well as minichromosome vector sequences are referred to as minichromosomes. The process of assembling minichromosomes from centromere clones/fragments and minichromosome vector sequences can be done in several ways, and involves techniques that are common practice among those trained in molecular biology:

1) Joining Centromere Fragments to Minichromosome Vector Sequences:

Centromere DNA fragments and minichromosome vector DNA fragments are generated and purified using conventional techniques, some of which include restriction enzyme digestion, agarose gel electrophoresis, gel purification of specific fragments, anion-exchange purification and ethanol precipitation. The resulting purified centromere and vector fragments are enzymatically joined in vitro, using for example T4 DNA ligase. The ends of the fragments can be cohesive, as the result of digestion with compatible restriction endonucleases or from the addition of compatible oligonucleotide linkers; alternatively the ends of the fragments can be blunt and can be directly joined. Following ligation, the resulting minichromosomes are introduced into *E. coli*, other bacteria, yeast, or plant cells using chemical or physical transformation methods. The structure of the resulting minichromosomes can be determined by recovering them from the host organism and assessing DNA fragment size and composition.

2) Transfer of Minichromosome Vector Sequences into Centromere Clones by Site-specific Recombination:

The minichromosome vector sequences can be constructed to include site-specific recombination sequences (for example those recognized by the bacteriophage P1 Cre recombinase, or the bacteriophage lambda integrase, or similar recombination enzymes). A compatible recombination site, or a pair of such sites, can also be included in the centromere clones. Incubation of the minichromosome vector and the centromere clone in the presence of the recombinase enzyme causes strand exchange to occur between the recombination sites in the two plasmids; the resulting minichromosomes contain centromere sequences as well as minichromosome vector sequences (FIG. 5). Introducing the DNA molecules formed in such recombination reactions into *E. coli*, other bacteria, yeast or plant cells can be followed by selection for marker genes present on both parental plasmids, allowing the isolation of minichromosomes.

3) Minichromosome Vector Tailing Method for Minichromosome Construction:

Centromere DNA fragments isolated from genomic DNA or from centromere clones can be modified on their ends by treatment with restriction endonucleases, or by ligation with DNA molecules including, but not limited to, oligonucleotide linkers, or by the addition of nucleotides, to produce a desired cohesive or blunt end. These fragments are size-fractionated by, agarose gel electrophoresis or other methods, and the centromere fragments purified using conventional techniques. Minichromosome vector fragments are generated and purified in a similar manner, resulting in linear minichromosome vector sequences with DNA ends compatible with those on the centromere fragments. Compatible ends in this case are defined by ends that can be joined in vitro by the action of a ligase enzyme. As shown in FIG. 6, the two fragments are then mixed so that the minichromosome vector molecules are present in at least two-fold molar excess over the centromere fragments. The fragments are joined by the addition of a ligase enzyme (for example bacteriophage T4 DNA ligase), resulting in the formation of DNA molecules in which minichromosome vector molecules have been joined to both ends of the same centromere fragment. Digestion of the ligation mixture with a rare-cutting restriction or homing endonuclease (for example endonucleases with recognition sequences of 8 or more bases) results in linear minichromosome precursors consisting of a fragment of the original minichromosome vector attached to each end of the centromere fragment. The ends of this hybrid molecule are compatible because they were created by the same restriction enzyme. This linear minichromosome precursor is purified, for example, by agarose gel electrophoresis followed by gel purification of the DNA fragments of the expected length. The purified DNA molecules are circularized by joining the ends, for example by treatment with a DNA ligase enzyme. The resulting minichromosome molecules can be introduced into *E. coli*, other bacteria, yeast or plant cells, followed by purification and characterization using conventional methods.

VII. Use of Minichromosomes for Plant Transformation

1) Delivery of Minichromosomes into Plant Cells:

Minichromosomes are purified and delivered into plant cells, either individually or as a mixture. The minichromosomes can be either circular or linear or mixtures thereof. The plant cells used for minichromosome delivery can be either intact seedlings, immature or mature plants, parts of seedlings or plants, specific plant tissues (for example leaves, stems, roots, flowers, fruits), differentiated tissues cultured in vitro (for example roots), or undifferentiated cells (for example callus) cultured in vitro. The minichromosome DNA can be delivered into plant cells by a variety of methods including but not limited to the following: electroporation; *Agrobacterium*-mediated DNA delivery; virus-mediated DNA delivery; delivery mediated by salts or lipids that facilitate the cellular uptake of DNA; microinjection of DNA; manipulation into a cell of DNA-coated or DNA-containing particles, droplets, micelles, microspheres, or chemical complexes using a variety of techniques, including biolistic particle bombardment, optical tweezers, particle beams, and electrospray apparatus; manipulation of DNA-coated magnetic particles into the cells by magnetic fields; DNA delivery into cells by cell wounding using microneedles (for example silicon carbide needles); sonication or other acoustic treatment of the cells to facilitate DNA uptake; fusion of plant cells with other cell types carrying a minichromosome, including bacterial, yeast, or other plant cells; any other electrical, chemical, physical, or biological mechanism that results in the introduction of minichromosome DNA into the plant cell 2) Isolating Plant Cells Containing Minichromosomes:

Following minichromosome delivery, plant cells, plant tissues, or complete plants carrying the minichromosome can be isolated by a variety of selection methods. Selection involves subjecting the plant cells, tissues or plants to chemical, environmental, or mechanical treatments that enrich for those cells, tissue or plants that contain a minichromosome. The selection methods include but are not limited to: fluorescence-activated cell sorting of cells, cell clumps, or cell protoplasts based on expression of a marker protein encoded by the minichromosome (for example, a fluorescent protein such as DsRed); affinity purification of cells, cell clumps, or protoplasts based on expression of a cell wall protein, membrane protein, or membrane-associated protein encoded by the minichromosome; any cell fractionation method capable of separating cells based on their density, size or shape to enrich for cells with a property that differs from that of the starting population and is conferred by the minichromosome; selection of cells for resistance to an antibiotic conferred by the minichromosome; selection of cells for resistance to an herbicide conferred by the minichromosome; selection of cells for resistance to a toxic metal, salt, mineral or other substance conferred by the minichromosome; selection of cells for resistance to abiotic stress (for example heat, cold, acid, base, osmotic stress) conferred by the minichromosome; selection of cells capable of utilizing a carbon source or other nutrient source not normally utilized by plant cells, this utilization function being conferred by the minichromosome. As a result of the treatment, a population of plant cells can be obtained that contain minichromosomes. Individual clones or sub-populations of these cells can be expanded in culture for further characterization.

Alternatively, plant cells, plant tissues, or complete plants that carry minichromosomes can be identified by direct screening. Such methods involve subjecting each cell, plant, or tissue to diagnostic tests indicative of the presence of the minichromosome. These tests can include direct assays for the presence of minichromosome DNA, or indirect assays for properties conferred by the minichromosome. Direct assays for the presence of the minichromosome DNA include but are not limited to: staining of cells with DNA-binding molecules to allow detection of an additional chromosome; in situ hybridization with labeled DNA probes corresponding to sequences present on the minichromosome; southern blots or dot blots of DNA extracted from the cells, plant or tissue and probed with labeled DNA sequences corresponding to sequences present on the minichromosome; electrophoresis of genomic DNA extracted from the cells, plant or tissue under conditions that allow identification of the minichromosome; amplification of specific sequences present on the minichromosome from genomic DNA extracted from the cells, plant or tissue using the polymerase chain reaction. Indirect assays for properties conferred by the minichromosome include but are not limited to: detection of the expression of a fluorescent marker encoded by the minichromosome by fluorescence microscopy, flow cytometery or fluorimetry; detection of the expression of a protein encoded by the minichromosome by use of specific antibodies, or any other reagent capable of specifically binding to the protein; use of cell fractionation methods capable of detecting a specific density, size or shape of the cells or tissues, that is conferred by the minichromosome; growth of cells, seedlings, plants or tissues on an antibiotic-containing medium to determine the presence of an antibiotic-resistance gene encoded by the minichromosome; growth of cells, seedlings, plants or tissues on an herbicide-containing medium to determine the presence of an herbicide-resistance gene encoded by the minichromosome; growth of cells, seedlings, plants or tissues on a medium containing a toxic metal, salt, mineral or other substance to determine the presence of an gene conferring resistance to this substance encoded by the minichromosome; growth of cells, tissues or plants under conditions of abiotic stress (for example heat, cold, acid, base, osmotic stress) to determine the presence of a gene conferring resistance to this stress encoded by the minichromosome; growth of cells on a medium containing a carbon source or other nutrient source normally not utilized by plant cells, to determine the presence of a utilization function conferred by the minichromosome.

3) Characterization of Plant Cell Clones Containing Minichromosomes

Plant cells, tissues, or entire plants containing minichromosomes can be further characterized to determine whether the minichromosome is an autonomous DNA molecule, or whether it is associated with one of the plant cell's chromosomes by integration. The methods used for this analysis include, but are not limited to, the following:

1) Detection of marker protein expression by microscopy, flow cytometry, fluorimetry, enzymatic assays, cell staining or any other technique that allows the detection of a marker protein having a specific enzymatic activity, or conferring a specific color, or fluorescence property onto the cells. For example, if a cell line has been selected for containing a minichromosome by selecting for the function of a resistance gene encoded by the minichromosome, and if a marker protein is also encoded by the minichromosome, then expression of this marker protein in the selected cells is an indication of the presence of the entire minichromosome, and could indicate autonomy of this minichromosome from the cell's other chromosomes.

2) Use of gel electrophoresis to detect a minichromosome in genomic DNA isolated from the plant cells, tissue or entire plants. For example, genomic DNA isolated from the cells, tissues or plants can be fractionated by gel electrophoresis, either intact or following digestion with restriction endonucleases or homing endonucleases, allowing the detection of a minichromosome or a fragment of a minichromosome.

3) Use of southern blots or dot blots of DNA extracted from the cells, tissue or plants to detect the presence of specific sequences contained on the minichromosome. For example, digestion of genomic DNA extracted from the cells, tissues or plants can be fractionated by agarose gel electrophoresis, blotted onto a DNA-binding membrane, and probed with labeled DNA sequences corresponding to sequences present on the minichromosome to detect specific fragments of minichromosome DNA, and thus allowing the determination of the autonomous, or integrated structure of the minichromosome.

4) Cytological techniques for directly visualizing the minichromosome in the transformed cells, such as staining of cells with DNA-binding dyes or in situ hybridization with labeled DNA probes corresponding to sequences present on the minichromosome.

5) Genetic analysis of marker segregation by scoring marker inheritance in progeny of a plant containing a minichromosome. For example, markers present on an autonomous minichromosome will segregate independently from markers on the arms of the host chromosomes in a population of F2 progeny generated from a cross between a line carrying a minichromosome and a second marked line that doesn't carry the minichromosome. Markers include but are not limited to: visible markers conferring a visible characteristic to the plant; selectable markers, conferring resistance to an antibiotic, herbicide, or other toxic compound; enzymatic markers, conferring an enzymatic activity that can be assays in the plant or in extracts made from the plant; protein markers, allowing the specific detection of a protein expressed in the plant; molecular markers, such as restriction fragment length polymorphisms, amplified fragment length polymorphisms, short sequence repeat (microsatellite) markers, presence of certain sequences in the DNA of the plant as detected by the polymerase chain reaction, single nucleotide polymorphisms or cleavable amplified polymorphic sites.

4) Plant Regeneration from Transformed Cell Clones:

Plant cells or tissues that harbor minichromosomes can be used to regenerate entire plants. This will be accomplished with standard techniques of plant regeneration from differentiated tissues or undifferentiated cells. Typically, transformed tissues or callus are subjected to a series of treatments with media containing various mixtures of plant hormones and growth regulators that promote the formation of a plant embryo, specific plant tissues or organs, or a complete plant (roots and shoot) from the starting cells or tissues. Following plant regeneration, the plant can be grown either in sterile media or in soil.

VIII. Testing Minichromosome Inheritance in Plant Cells

The inheritance of minichromosomes can be measured through one or more cell divisions. After isolating cells, tissues, or entire plants that contain the minichromosome, the population of cells is allowed to grow (either with or without selection), and the presence of the minichromosome is monitored as the cells divide. Minichromosomes can be detected in cells by a variety of methods, including but not limited to: detection of fluorescence or any other visual characteristic arising from a marker protein gene present on the minichromosome; resistance to an antibiotic, herbicide, toxic metal, salt, mineral or other substance, or abiotic stress as outlined above (Isolating plant cells containing minichromosomes); staining of cells with DNA-binding molecules to allow detection of an additional chromosome; in situ hybridization with labeled DNA probes corresponding to sequences present on the minichromosome; southern blots or dot blots of DNA extracted from the cell population and probed with labeled DNA sequences corresponding to sequences present on the minichromosome; expression of a marker enzyme encoded by a gene present on the minichromosome (i.e. luciferase, alkaline phosphatase, beta-galactosidase, etc.) that can be assayed in the cells or in an extract made from the cells.

The percentage of cells containing the chromosome is determined at regular intervals during this growth phase. The change in the fraction of cells harboring the minichromosome, divided by the number of cell divisions, represents the average minichromosome loss rate. Minichromosomes with the lowest loss rates have the highest level of inheritance.

IX. Recovery of Minichromosomes from Plant Cells

Recovery of minichromosomes from plant cells can be achieved by a variety of techniques, including, but not limited to, the following:

1) Extracting the genomic DNA of transformed plant cells and introducing that DNA into *E. coli*, other bacteria or yeast and selecting for the antibiotic resistance genes present on the minichromosome.
2) Isolation of chromosomes from cells, tissues or plants containing minichromosomes, and sorting these by flow cytometry to allow the separation of chromosomes of different size;
3) Isolation of individual chromosomes from a cell harboring minichromosomes by micro-manipulation involving mechanical devices such as needles made of glass, metal or other suitable substances, or other techniques such as optical tweezers, or micro-suction devices.
4) Combinations of the above, for example chromosome isolation by flow cytometry or micromanipulation followed by introduction into *E. coli*, other bacteria, yeast or plant cells.

The resulting minichromosomes "rescued" in this fashion may differ from their parental molecules in total size, size of the centromere, presence or absence of additional sequences, and overall arrangement of the sequences. These procedures allow the isolation of DNA molecules capable of replicating and segregating in plant cells without having to test minichromosomes individually. For example, after delivery of pools of minichromosomes, or pools of centromere clones into plant cells, tissues or whole plants, and recovering them by the methods listed above, facilitates the selection of specific minichromosomes or centromere clones that remain autonomous in plant cells. Whereas plant transformation with minichromosomes relies on the sequences contributed by minichromosome vectors, the recovery methods do not necessarily require minichromosome vector sequences; as a result, pools of centromere clones can be delivered into plant cells followed by recovery of the ones that replicated and persist.

X. Exogenous Genes for Expression in Plants

One particularly important advance of the present invention is that it provides methods and compositions for expression of exogenous genes in plant cells. One advance of the constructs of the current invention is that they enable the introduction of multiple genes (often referred to as gene "stacking"), potentially representing an entire biochemical pathway, or any combination of genes encoding different biochemical processes or pathways. Significantly, the current invention allows for the transformation of plant cells with a minichromosome comprising a number of structural genes. Another advantage is that more than one minichromosome could be introduced, allowing combinations of genes to be moved and shuffled. Moreover, the ability to eliminate a minichromosome from a plant would provide additional flexibility, making it possible to alter the set of genes contained within a plant. Further, by using site-specific recombinases, it should be possible to add genes to an existing minichromosome once it is in a plant.

Added genes often will be genes that direct the expression of a particular protein or polypeptide product, but they also may be non-expressible DNA segments, e.g., transposons such as Ds that do not direct their own transposition. As used herein, an "expressible gene" is any gene that is capable of being transcribed into RNA (e.g., mRNA, antisense RNA, etc.) or translated into a protein, expressed as a trait of interest, or the like, etc., and is not limited to selectable, screenable or non-selectable marker genes. The inventors also contemplate that, where both an expressible gene that is not necessarily a marker gene is employed in combination with a marker gene, one may employ the separate genes on either the same or different DNA segments for transformation. In the latter case, the different vectors may be delivered concurrently to recipient cells to maximize cotransformation or may be delivered sequentially.

The choice of the particular DNA segments to be delivered to the recipient cells often will depend on the purpose of the transformation. One of the major purposes of transformation of crop plants is to add some commercially desirable, agronomically important traits to the plant. Such traits include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress; oxidative stress; increased yields; food content and makeup; physical appearance; male sterility; drydown; standability; prolificacy; starch quantity and quality; oil quantity and quality; protein quality and quantity; amino acid composition; the production of a pharmaceutically active protein; the production of a small molecule with medicinal properties; the production of a chemical including those with industrial utility; the production of nutraceuticals, carbohydrates, RNAs, lipids, fuels, dyes, pigments, vitamins, scents, flavors, vaccines, antibodies, hormones, and the like. Additionally one could create a library of an entire genome from any organism or organelle including mammals, plants, microbes, fungi, bacteria, represented on minichromosomes. Furthermore one could incorporate a desired genomic segment such as one that includes a quantitative trait onto a minichromosome. One may desire to incorporate one or more genes conferring any such desirable trait or traits, such as, for example, a gene or genes encoding herbicide resistance.

In certain embodiments, the present invention contemplates the transformation of a recipient cell with minichromosomes comprising more than one exogenous gene. An "exogenous gene," can be a gene not normally found in the host genome in an identical context, or alternatively, the minichromosome could be used to introduce extra copies of host genes into a cell. The gene may be isolated from a different species than that of the host genome, or alternatively, isolated from the host genome but operably linked to one or more regulatory regions which differ from those found in the unaltered, native gene. Two or more exogenous genes also can be supplied in a single transformation event using either distinct transgene-encoding vectors, or using a single vector incorporating two or more gene coding sequences. For example, plasmids bearing the bar and aroA expression units in either convergent, divergent, or colinear orientation, are considered to be particularly useful. Further preferred combinations are those of an insect resistance gene, such as a Bt gene, along with a protease inhibitor gene such as pinII, or the use of bar in combination with either of the above genes. Of course, any two or more transgenes of any description, such as those conferring herbicide, insect, disease (viral, bacterial, fungal, nematode) or drought resistance, male sterility, drydown, standability, prolificacy, starch properties, oil quantity and quality, modified chemical production, pharmaceutical or nutraceutical properties, bioremediation properties, increased biomass, altered growth rate, altered fitness, altered salinity tolerance, altered thermal tolerance, altered growth form, altered composition, altered metabolism, altered biodegradability, altered $CO_2$ fixation, altered stress tolerance, presence of bioindicator activity, altered digestibility by humans or animals, altered allergenicity, altered mating characteristics, altered pollen dispersal, altered appearance, improved environmental impact, nitrogen fixation capability, or those increasing yield or nutritional quality may be employed as desired.

(i) Herbicide Resistance

The genes encoding phosphinothricin acetyltransferase (bar and pat), glyphosate tolerant EPSP synthase genes, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil) are good examples of herbicide resistant genes for use in transformation. The bar and pat genes code for an enzyme, phosphinothricin acetyltransferase (PAT), which inactivates the herbicide phosphinothricin and prevents this compound from inhibiting glutamine synthetase enzymes. The enzyme 5-enolpyruvylshikimate 3-phosphate synthase (EPSP Synthase), is normally inhibited by the herbicide N-(phosphonomethyl)glycine (glyphosate). However, genes are known that encode glyphosate-resistant EPSP synthase enzymes. These genes are particularly contemplated for use in plant transformation. The deh gene encodes the enzyme dalapon dehalogenase and confers resistance to the herbicide dalapon. The bxn gene codes for a specific nitrilase enzyme that converts bromoxynil to a non-herbicidal degradation product.

(ii) Insect Resistance

Potential insect resistance genes that can be introduced include *Bacillus thuringiensis* crystal toxin genes or Bt genes (Watrud et al., 1985). Bt genes may provide resistance to lepidopteran or coleopteran pests such as European Corn Borer (ECB). Preferred Bt toxin genes for use in such embodiments include the CryIA(b) and CryIA(c) genes. Endotoxin genes from other species of *B. thuringiensis* which affect insect growth or development also may be employed in this regard.

It is contemplated that preferred Bt genes for use in the transformation protocols disclosed herein will be those in which the coding sequence has been modified to effect increased expression in plants, and more particularly, in monocot plants. Means for preparing synthetic genes are well known in the art and are disclosed in, for example, U.S. Pat. No. 5,500,365 and U.S. Pat. No. 5,689,052, each of the disclosures of which are specifically incorporated herein by reference in their entirety. Examples of such modified Bt toxin genes include a synthetic Bt CryIA(b) gene (Perlak et al., 1991), and the synthetic CryIA(c) gene termed 1800b (PCT Application WO 95/06128). Some examples of other Bt toxin genes known to those of skill in the art are given in Table 1 below.

TABLE 1

*Bacillus thuringiensis* δ-Endotoxin Genes[a]

| New Nomenclature | Old Nomenclature | GenBank Accession |
|---|---|---|
| Cry1Aa | CryIA(a) | M11250 |
| Cry1Ab | CryIA(b) | M13898 |
| Cry1Ac | CryIA(c) | M11068 |
| Cry1Ad | CryIA(d) | M73250 |
| Cry1Ae | CryIA(e) | M65252 |

TABLE 1-continued

Bacillus thuringiensis δ-Endotoxin Genes[a]

| New Nomenclature | Old Nomenclature | GenBank Accession |
| --- | --- | --- |
| Cry1Ba | CryIB | X06711 |
| Cry1Bb | ET5 | L32020 |
| Cry1Bc | PEG5 | Z46442 |
| Cry1Bd | CryE1 | U70726 |
| Cry1Ca | CryIC | X07518 |
| Cry1Cb | CryIC(b) | M97880 |
| Cry1Da | CryID | X54160 |
| Cry1Db | PrtB | Z22511 |
| Cry1Ea | CryIE | X53985 |
| Cry1Eb | CryIE(b) | M73253 |
| Cry1Fa | CryIF | M63897 |
| Cry1Fb | PrtD | Z22512 |
| Cry1Ga | PrtA | Z22510 |
| Cry1Gb | CryH2 | U70725 |
| Cry1Ha | PrtC | Z22513 |
| Cry1Hb |  | U35780 |
| Cry1Ia | CryV | X62821 |
| Cry1Ib | CryV | U07642 |
| Cry1Ja | ET4 | L32019 |
| Cry1Jb | ET1 | U31527 |
| Cry1K |  | U28801 |
| Cry2Aa | CryIIA | M31738 |
| Cry2Ab | CryIIB | M23724 |
| Cry2Ac | CryIIC | X57252 |
| Cry3A | CryIIIA | M22472 |
| Cry3Ba | CryIIIB | X17123 |
| Cry3Bb | CryIIIB2 | M89794 |
| Cry3C | CryIIID | X59797 |
| Cry4A | CryIVA | Y00423 |
| Cry4B | CryIVB | X07423 |
| Cry5Aa | CryVA(a) | L07025 |
| Cry5Ab | CryVA(b) | L07026 |
| Cry6A | CryVIA | L07022 |
| Cry6B | CryVIB | L07024 |
| Cry7Aa | CryIIIC | M64478 |
| Cry7Ab | CryIIICb | U04367 |
| Cry8A | CryIIIE | U04364 |
| Cry8B | CryIIIG | U04365 |
| Cry8C | CryIIIF | U04366 |
| Cry9A | CryIG | X58120 |
| Cry9B | CryIX | X75019 |
| Cry9C | CryIH | Z37527 |
| Cry10A | CryIVC | M12662 |
| Cry11A | CryIVD | M31737 |
| Cry11B | Jeg80 | X86902 |
| Cry12A | CryVB | L07027 |
| Cry13A | CryVC | L07023 |
| Cry14A | CryVD | U13955 |
| Cry15A | 34 kDa | M76442 |
| Cry16A | cbm71 | X94146 |
| Cry17A | cbm71 | X99478 |
| Cry18A | CryBP1 | X99049 |
| Cry19A | Jeg65 | Y08920 |
| Cyt1Aa | CytA | X03182 |
| Cyt1Ab | CytM | X98793 |
| Cyt2A | CytB | Z14147 |
| Cyt2B | CytB | U52043 |

[a]Adapted from: the Bacillus thuringiensis Endotoxin Nomenclature Web Site.

Protease inhibitors also may provide insect resistance (Johnson et al., 1989), and will thus have utility in plant transformation. The use of a protease inhibitor II gene, pinII, from tomato or potato is envisioned to be particularly useful. Even more advantageous is the use of a pinII gene in combination with a Bt toxin gene, the combined effect of which has been discovered to produce synergistic insecticidal activity. Other genes which encode inhibitors of the insect's digestive system, or those that encode enzymes or co-factors that facilitate the production of inhibitors, also may be useful. This group may be exemplified by oryzacystatin and amylase inhibitors such as those from wheat and barley.

Also, genes encoding lectins may confer additional or alternative insecticide properties. Lectins (originally termed phytohemagglutinins) are multivalent carbohydrate-binding proteins which have the ability to agglutinate red blood cells from a range of species. Lectins have been identified recently as insecticidal agents with activity against weevils, ECB and rootworm (Murdock et al., 1990; Czapla & Lang, 1990). Lectin genes contemplated to be useful include, for example, barley and wheat germ agglutinin (WGA) and rice lectins (Gatehouse et al., 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated that the expression of juvenile hormone esterase, directed towards specific insect pests, also may result in insecticidal activity, or perhaps cause cessation of metamorphosis (Hammock et al., 1990).

Transgenic plants expressing genes which encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant plants. Genes that code for activities that affect insect molting, such as those affecting the production of ecdysteroid UDP-glucosyl transferase, also fall within the scope of the useful transgenes of the present invention.

Genes that code for enzymes that facilitate the production of compounds that reduce the nutritional quality of the host plant to insect pests also are encompassed by the present invention. It may be possible, for instance, to confer insecticidal activity on a plant by altering its sterol composition. Sterols are obtained by insects from their diet and are used for hormone synthesis and membrane stability. Therefore alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti-nutritional effects on insects and to reduce the nutritional quality of their diet. Therefore, further embodiments of the invention concern transgenic plants with enhanced lipoxygenase activity which may be resistant to insect feeding.

*Tripsacum dactyloides* is a species of grass that is resistant to certain insects, including corn root worm. It is anticipated that genes encoding proteins that are toxic to insects or are involved in the biosynthesis of compounds toxic to insects will be isolated from *Tripsacum* and that these novel genes will be useful in conferring resistance to insects. It is known that the basis of insect resistance in *Tripsacum* is genetic, because said resistance has been transferred to *Zea mays* via sexual crosses (Branson and Guss, 1972). It is further anticipated that other cereal, monocot or dicot plant species may have genes encoding proteins that are toxic to insects which would be useful for producing insect resistant plants.

Further genes encoding proteins characterized as having potential insecticidal activity also may be used as transgenes in accordance herewith. Such genes include, for example, the cowpea trypsin inhibitor (CpTI; Hilder et al., 1987)

which may be used as a rootworm deterrent; genes encoding avermectin (*Avermectin and Abamectin*., Campbell, W. C., Ed., 1989; Ikeda et al., 1987) which may prove particularly useful as a corn rootworm deterrent; ribosome inactivating protein genes; and even genes that regulate plant structures. Transgenic plants including anti-insect antibody genes and genes that code for enzymes that can convert a non-toxic insecticide (pro-insecticide) applied to the outside of the plant into an insecticide inside the plant also are contemplated.

(iii) Environment or Stress Resistance

Improvement of a plants ability to tolerate various environmental stresses such as, but not limited to, drought, excess moisture, chilling, freezing, high temperature, salt, and oxidative stress, also can be effected through expression of novel genes. It is proposed that benefits may be realized in terms of increased resistance to freezing temperatures through the introduction of an "antifreeze" protein such as that of the Winter Flounder (Cutler et al., 1989) or synthetic gene derivatives thereof. Improved chilling tolerance also may be conferred through increased expression of glycerol-3-phosphate acetyltransferase in chloroplasts (Wolter et al., 1992). Resistance to oxidative stress (often exacerbated by conditions such as chilling temperatures in combination with high light intensities) can be conferred by expression of superoxide dismutase (Gupta et al., 1993), and may be improved by glutathione reductase (Bowler et al., 1992). Such strategies may allow for tolerance to freezing in newly emerged fields as well as extending later maturity higher yielding varieties to earlier relative maturity zones.

It is contemplated that the expression of novel genes that favorably effect plant water content, total water potential, osmotic potential, and turgor will enhance the ability of the plant to tolerate drought. As used herein, the terms "drought resistance" and "drought tolerance" are used to refer to a plants increased resistance or tolerance to stress induced by a reduction in water availability, as compared to normal circumstances, and the ability of the plant to function and survive in lower-water environments. In this aspect of the invention it is proposed, for example, that the expression of genes encoding for the biosynthesis of osmotically-active solutes, such as polyol compounds, may impart protection against drought. Within this class are genes encoding for mannitol-L-phosphate dehydrogenase (Lee and Saier, 1982) and trehalose-6-phosphate synthase (Kaasen et al., 1992). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski et al., 1992, 1993).

Similarly, the efficacy of other metabolites in protecting either enzyme function (e.g., alanopine or propionic acid) or membrane integrity (e.g., alanopine) has been documented (Loomis et al., 1989), and therefore expression of genes encoding for the biosynthesis of these compounds might confer drought resistance in a manner similar to or complimentary to mannitol. Other examples of naturally occurring metabolites that are osmotically active and/or provide some direct protective effect during drought and/or desiccation include fructose, erythritol (Coxson et al., 1992), sorbitol, dulcitol (Karsten et al., 1992), glucosylglycerol (Reed et al., 1984; ErdMann et al., 1992), sucrose, stachyose (Koster and Leopold, 1988; Blackman et al., 1992), raffinose (Bernal-Lugo and Leopold, 1992), proline (Rensburg et al., 1993), glycine betaine, ononitol and pinitol (Vernon and Bohnert, 1992). Continued canopy growth and increased reproductive fitness during times of stress will be augmented by introduction and expression of genes such as those controlling the osmotically active compounds discussed above and other such compounds. Currently preferred genes which promote the synthesis of an osmotically active polyol compound are genes which encode the enzymes mannitol-1-phosphate dehydrogenase, trehalose-6-phosphate synthase and myo-inositol 0-methyltransferase.

It is contemplated that the expression of specific proteins also may increase drought tolerance. Three classes of Late Embryogenic Proteins have been assigned based on structural similarities (see Dure et al., 1989). All three classes of LEAs have been demonstrated in maturing (i.e. desiccating) seeds. Within these 3 types of LEA proteins, the Type-II (dehydrin-type) have generally been implicated in drought and/or desiccation tolerance in vegetative plant parts (i.e. Mundy and Chua, 1988; Piatkowski et al., 1990; Yamaguchi-Shinozaki et al., 1992). Recently, expression of a Type-III LEA (HVA-1) in tobacco was found to influence plant height, maturity and drought tolerance (Fitzpatrick, 1993). In rice, expression of the HVA-1 gene influenced tolerance to water deficit and salinity (Xu et al., 1996). Expression of structural genes from all three LEA groups may therefore confer drought tolerance. Other types of proteins induced during water stress include thiol proteases, aldolases and transmembrane transporters (Guerrero et al., 1990), which may confer various protective and/or repair-type functions during drought stress. It also is contemplated that genes that effect lipid biosynthesis and hence membrane composition might also be useful in conferring drought resistance on the plant.

Many of these genes for improving drought resistance have complementary modes of action. Thus, it is envisaged that combinations of these genes might have additive and/or synergistic effects in improving drought resistance in plants. Many of these genes also improve freezing tolerance (or resistance); the physical stresses incurred during freezing and drought are similar in nature and may be mitigated in similar fashion. Benefit may be conferred via constitutive expression of these genes, but the preferred means of expressing these novel genes may be through the use of a turgor-induced promoter (such as the promoters for the turgor-induced genes described in Guerrero et al., 1990 and Shagan et al., 1993 which are incorporated herein by reference). Spatial and temporal expression patterns of these genes may enable plants to better withstand stress.

It is proposed that expression of genes that are involved with specific morphological traits that allow for increased water extractions from drying soil would be of benefit. For example, introduction and expression of genes that alter root characteristics may enhance water uptake. It also is contemplated that expression of genes that enhance reproductive fitness during times of stress would be of significant value. For example, expression of genes that improve the synchrony of pollen shed and receptiveness of the female flower parts, i.e., silks, would be of benefit. In addition it is proposed that expression of genes that minimize kernel abortion during times of stress would increase the amount of grain to be harvested and hence be of value.

Given the overall role of water in determining yield, it is contemplated that enabling plants to utilize water more efficiently, through the introduction and expression of novel genes, will improve overall performance even when soil water availability is not limiting. By introducing genes that improve the ability of plants to maximize water usage across a full range of stresses relating to water availability, yield stability or consistency of yield performance may be realized.

(iv) Disease Resistance

It is proposed that increased resistance to diseases may be realized through introduction of genes into plants, for example, into monocotyledonous plants such as maize. It is possible to produce resistance to diseases caused by viruses, bacteria, fungi and nematodes. It also is contemplated that control of mycotoxin producing organisms may be realized through expression of introduced genes.

Resistance to viruses may be produced through expression of novel genes. For example, it has been demonstrated that expression of a viral coat protein in a transgenic plant can impart resistance to infection of the plant by that virus and perhaps other closely related viruses (Cuozzo et al., 1988, Hemenway et al., 1988, Abel et al., 1986). It is contemplated that expression of antisense genes targeted at essential viral functions may also impart resistance to viruses. For example, an antisense gene targeted at the gene responsible for replication of viral nucleic acid may inhibit replication and lead to resistance to the virus. It is believed that interference with other viral functions through the use of antisense genes also may increase resistance to viruses. Further, it is proposed that it may be possible to achieve resistance to viruses through other approaches, including, but not limited to the use of satellite viruses.

It is proposed that increased resistance to diseases caused by bacteria and fungi may be realized through introduction of novel genes. It is contemplated that genes encoding so-called "peptide antibiotics," pathogenesis related (PR) proteins, toxin resistance, and proteins affecting host-pathogen interactions such as morphological characteristics will be useful. Peptide antibiotics are polypeptide sequences which are inhibitory to growth of bacteria and other microorganisms. For example, the classes of peptides referred to as cecropins and magainins inhibit growth of many species of bacteria and fungi. It is proposed that expression of PR proteins in monocotyledonous plants such as maize may be useful in conferring resistance to bacterial disease. These genes are induced following pathogen attack on a host plant and have been divided into at least five classes of proteins (Bol, Linthorst, and Cornelissen, 1990). Included amongst the PR proteins are β-1,3-glucanases, chitinases, and osmotin and other proteins that are believed to function in plant resistance to disease organisms. Other genes have been identified that have antifungal properties, e.g., UDA (stinging nettle lectin) and hevein (Broakaert et al., 1989; Barkai-Golan et al., 1978). It is known that certain plant diseases are caused by the production of phytotoxins. It is proposed that resistance to these diseases would be achieved through expression of a novel gene that encodes an enzyme capable of degrading or otherwise inactivating the phytotoxin. It also is contemplated that expression of novel genes that alter the interactions between the host plant and pathogen may be useful in reducing the ability of the disease organism to invade the tissues of the host plant, e.g., an increase in the waxiness of the leaf cuticle or other morphological characteristics.

(v) Plant Agronomic Characteristics

Two of the factors determining where crop plants can be grown are the average daily temperature during the growing season and the length of time between frosts. Within the areas where it is possible to grow a particular crop, there are varying limitations on the maximal time it is allowed to grow to maturity and be harvested. For example, a variety to be grown in a particular area is selected for its ability to mature and dry down to harvestable moisture content within the required period of time with maximum possible yield. Therefore, crops of varying maturities is developed for different growing locations. Apart from the need to dry down sufficiently to permit harvest, it is desirable to have maximal drying take place in the field to minimize the amount of energy required for additional drying post-harvest. Also, the more readily a product such as grain can dry down, the more time there is available for growth and kernel fill. It is considered that genes that influence maturity and/or dry down can be identified and introduced into plant lines using transformation techniques to create new varieties adapted to different growing locations or the same growing location, but having improved yield to moisture ratio at harvest. Expression of genes that are involved in regulation of plant development may be especially useful.

It is contemplated that genes may be introduced into plants that would improve standability and other plant growth characteristics. Expression of novel genes in plants which confer stronger stalks, improved root systems, or prevent or reduce ear droppage would be of great value to the farmer. It is proposed that introduction and expression of genes that increase the total amount of photoassimilate available by, for example, increasing light distribution and/or interception would be advantageous. In addition, the expression of genes that increase the efficiency of photosynthesis and/or the leaf canopy would further increase gains in productivity. It is contemplated that expression of a phytochrome gene in crop plants may be advantageous. Expression of such a gene may reduce apical dominance, confer semidwarfism on a plant, and increase shade tolerance (U.S. Pat. No. 5,268,526). Such approaches would allow for increased plant populations in the field.

(vi) Nutrient Utilization

The ability to utilize available nutrients may be a limiting factor in growth of crop plants. It is proposed that it would be possible to alter nutrient uptake, tolerate pH extremes, mobilization through the plant, storage pools, and availability for metabolic activities by the introduction of novel genes. These modifications would allow a plant such as maize to more efficiently utilize available nutrients. It is contemplated that an increase in the activity of, for example, an enzyme that is normally present in the plant and involved in nutrient utilization would increase the availability of a nutrient. An example of such an enzyme would be phytase. It is further contemplated that enhanced nitrogen utilization by a plant is desirable. Expression of a glutamate dehydrogenase gene in plants, e.g., *E. coli* gdhA genes, may lead to increased fixation of nitrogen in organic compounds. Furthermore, expression of gdhA in plants may lead to enhanced resistance to the herbicide glufosinate by incorporation of excess ammonia into glutamate, thereby detoxifying the ammonia. It also is contemplated that expression of a novel gene may make a nutrient source available that was previously not accessible, e.g., an enzyme that releases a component of nutrient value from a more complex molecule, perhaps a macromolecule.

(vii) Male Sterility

Male sterility is useful in the production of hybrid seed. It is proposed that male sterility may be produced through expression of novel genes. For example, it has been shown that expression of genes that encode proteins that interfere with development of the male inflorescence and/or gametophyte result in male sterility. Chimeric ribonuclease genes that express in the anthers of transgenic tobacco and oilseed rape have been demonstrated to lead to male sterility (Mariani et al., 1990).

A number of mutations were discovered in maize that confer cytoplasmic male sterility. One mutation in particular, referred to as T cytoplasm, also correlates with sensitivity to Southern corn leaf blight. A DNA sequence, designated TURF-13 (Levings, 1990), was identified that correlates with T cytoplasm. It is proposed that it would be possible through the introduction of TURF-13 via transformation, to separate male sterility from disease sensitivity. As it is necessary to be able to restore male fertility for breeding purposes and for grain production, it is proposed that genes encoding restoration of male fertility also may be introduced.

(viii) Improved Nutritional Content

Genes may be introduced into plants to improve the nutrient quality or content of a particular crop. Introduction of genes that alter the nutrient composition of a crop may greatly enhance the feed or food value. For example, the protein of many grains is suboptimal for feed and food purposes, especially when fed to pigs, poultry, and humans. The protein is deficient in several amino acids that are essential in the diet of these species, requiring the addition of supplements to the grain. Limiting essential amino acids may include lysine, methionine, tryptophan, threonine, valine, arginine, and histidine. Some amino acids become limiting only after corn is supplemented with other inputs for feed formulations. The levels of these essential amino acids in seeds and grain may be elevated by mechanisms which include, but are not limited to, the introduction of genes to increase the biosynthesis of the amino acids, decrease the degradation of the amino acids, increase the storage of the amino acids in proteins, or increase transport of the amino acids to the seeds or grain.

The protein composition of a crop may be altered to improve the balance of amino acids in a variety of ways including elevating expression of native proteins, decreasing expression of those with poor composition, changing the composition of native proteins, or introducing genes encoding entirely new proteins possessing superior composition.

The introduction of genes that alter the oil content of a crop plant may also be of value. Increases in oil content may result in increases in metabolizable-energy-content and density of the seeds for use in feed and food. The introduced genes may encode enzymes that remove or reduce rate-limitations or regulated steps in fatty acid or lipid biosynthesis. Such genes may include, but are not limited to, those that encode acetyl-CoA carboxylase, ACP-acyltransferase, β-ketoacyl-ACP synthase, plus other well known fatty acid biosynthetic activities. Other possibilities are genes that encode proteins that do not possess enzymatic activity such as acyl carrier protein. Genes may be introduced that alter the balance of fatty acids present in the oil providing a more healthful or nutritive feedstuff. The introduced DNA also may encode sequences that block expression of enzymes involved in fatty acid biosynthesis, altering the proportions of fatty acids present in crops.

Genes may be introduced that enhance the nutritive value of the starch component of crops, for example by increasing the degree of branching, resulting in improved utilization of the starch in livestock by delaying its metabolism. Additionally, other major constituents of a crop may be altered, including genes that affect a variety of other nutritive, processing, or other quality aspects. For example, pigmentation may be increased or decreased.

Feed or food crops may also possess sub-optimal quantities of vitamins, antioxidants or other nutraceuticals, requiring supplementation to provide adequate nutritive value and ideal health value. Introduction of genes that enhance vitamin biosynthesis may be envisioned including, for example, vitamins A, E, $B_{12}$, choline, and the like. Mineral content may also be sub-optimal. Thus genes that affect the accumulation or availability of compounds containing phosphorus, sulfur, calcium, manganese, zinc, and iron among others would be valuable.

Numerous other examples of improvements of crops may be used with the invention. The improvements may not necessarily involve grain, but may, for example, improve the value of a crop for silage. Introduction of DNA to accomplish this might include sequences that alter lignin production such as those that result in the "brown midrib" phenotype associated with superior feed value for cattle.

In addition to direct improvements in feed or food value, genes also may be introduced which improve the processing of crops and improve the value of the products resulting from the processing. One use of crops if via wetmilling. Thus novel genes that increase the efficiency and reduce the cost of such processing, for example by decreasing steeping time, may also find use. Improving the value of wetmilling products may include altering the quantity or quality of starch, oil, corn gluten meal, or the components of gluten feed. Elevation of starch may be achieved through the identification and elimination of rate limiting steps in starch biosynthesis or by decreasing levels of the other components of crops resulting in proportional increases in starch.

Oil is another product of wetmilling, the value of which may be improved by introduction and expression of genes. Oil properties may be altered to improve its performance in the production and use of cooking oil, shortenings, lubricants or other oil-derived products or improvement of its health attributes when used in the food-related applications. Novel fatty acids also may be synthesized which upon extraction can serve as starting materials for chemical syntheses. The changes in oil properties may be achieved by altering the type, level, or lipid arrangement of the fatty acids present in the oil. This in turn may be accomplished by the addition of genes that encode enzymes that catalyze the synthesis of novel fatty acids and the lipids possessing them or by increasing levels of native fatty acids while possibly reducing levels of precursors. Alternatively, DNA sequences may be introduced which slow or block steps in fatty acid biosynthesis resulting in the increase in precursor fatty acid intermediates. Genes that might be added include desaturases, epoxidases, hydratases, dehydratases, and other enzymes that catalyze reactions involving fatty acid intermediates. Representative examples of catalytic steps that might be blocked include the desaturations from stearic to oleic acid and oleic to linolenic acid resulting in the respective accumulations of stearic and oleic acids. Another example is the blockage of elongation steps resulting in the accumulation of $C_8$ to $C_{12}$ saturated fatty acids.

(ix) Production or Assimilation of Chemicals or Biologicals

It may further be considered that a transgenic plant prepared in accordance with the invention may be used for the production or manufacturing of useful biological compounds that were either not produced at all, or not produced at the same level, in the corn plant previously. Alternatively, plants produced in accordance with the invention may be made to metabolize or absrob and concentrate certain compounds, such as hazardous wastes, thereby allowing bioremediation of these compounds.

The novel plants producing these compounds are made possible by the introduction and expression of one or potentially many genes with the constructs provided by the invention. The vast array of possibilities include but are not limited to any biological compound which is presently produced by any organism such as proteins, nucleic acids, primary and intermediary metabolites, carbohydrate polymers, enzymes for uses in bioremediation, enzymes for modifying pathways that produce secondary plant metabolites such as flavonoids or vitamins, enzymes that could produce pharmaceuticals, and for introducing enzymes that could produce compounds of interest to the manufacturing industry such as specialty chemicals and plastics. The compounds may be produced by the plant, extracted upon harvest and/or processing, and used for any presently recognized useful purpose such as pharmaceuticals, fragrances, and industrial enzymes to name a few.

(x) Non-Protein-Expressing Sequences

DNA may be introduced into plants for the purpose of expressing RNA transcripts that function to affect plant phenotype yet are not translated into protein. Two examples are antisense RNA and RNA with ribozyme activity. Both may serve possible functions in reducing or eliminating expression of native or introduced plant genes. However, as detailed below, DNA need not be expressed to effect the phenotype of a plant.

1. Antisense RNA

Genes may be constructed or isolated, which when transcribed, produce antisense RNA that is complementary to all or part(s) of a targeted messenger RNA(s). The antisense RNA reduces production of the polypeptide product of the messenger RNA. Genes may also be constructed to produce double-stranded RNA molecules complementary to all or part of the targeted messenger RNA(s). Genes designed in this manner will be referred to as RNAi constructs; the double-stranded RNA or RNAi constructs can trigger the sequence-specific degradation of the target messenger RNA. The polypeptide product of the target messenger RNA may be any protein. The aforementioned genes will be referred to as antisense genes and RNAi constructs, respectively. An antisense gene or RNAi construct may thus be introduced into a plant by transformation methods to produce a novel transgenic plant with reduced expression of a selected protein of interest. For example, the protein may be an enzyme that catalyzes a reaction in the plant. Reduction of the enzyme activity may reduce or eliminate products of the reaction which include any enzymatically synthesized compound in the plant such as fatty acids, amino acids, carbohydrates, nucleic acids and the like. Alternatively, the protein may be a storage protein, such as a zein, or a structural protein, the decreased expression of which may lead to changes in seed amino acid composition or plant morphological changes respectively. The possibilities cited above are provided only by way of example and do not represent the full range of applications.

2. Ribozymes

Genes also may be constructed or isolated, which when transcribed, produce RNA enzymes (ribozymes) which can act as endoribonucleases and catalyze the cleavage of RNA molecules with selected sequences. The cleavage of selected messenger RNAs can result in the reduced production of their encoded polypeptide products. These genes may be used to prepare novel transgenic plants which possess them. The transgenic plants may possess reduced levels of polypeptides including, but not limited to, the polypeptides cited above.

Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes.

Several different ribozyme motifs have been described with RNA cleavage activity (Symons, 1992). Examples include sequences from the Group I self splicing introns including Tobacco Ringspot Virus (Prody et al., 1986), Avocado Sunblotch Viroid (Palukaitis et al., 1979; Symons, 1981), and Lucerne Transient Streak Virus (Forster and Symons, 1987). Sequences from these and related viruses are referred to as hammerhead ribozyme based on a predicted folded secondary structure.

Other suitable ribozymes include sequences from RNase P with RNA cleavage activity (Yuan et al., 1992, Yuan and Altman, 1994, U.S. Pat. Nos. 5,168,053 and 5,624,824), hairpin ribozyme structures (Berzal-Herranz et al., 1992; Chowrira et al., 1993) and Hepatitis Delta virus based ribozymes (U.S. Pat. No. 5,625,047). The general design and optimization of ribozyme directed RNA cleavage activity has been discussed in detail (Haseloff and Gerlach, 1988, Symons, 1992, Chowrira et al., 1994; Thompson et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozyme, the cleavage site is a dinucleotide sequence on the target RNA is a uracil (U) followed by either an adenine, cytosine or uracil (A,C or U) (Perriman et al., 1992; Thompson et al., 1995). The frequency of this dinucleotide occurring in any given RNA is statistically 3 out of 16. Therefore, for a given target messenger RNA of 1,000 bases, 187 dinucleotide cleavage sites are statistically possible.

Designing and testing ribozymes for efficient cleavage of a target RNA is a process well known to those skilled in the art. Examples of scientific methods for designing and testing ribozymes are described by Chowrira et al., (1994) and Lieber and Strauss (1995), each incorporated by reference. The identification of operative and preferred sequences for use in down regulating a given gene is simply a matter of preparing and testing a given sequence, and is a routinely practiced "screening" method known to those of skill in the art.

3. Induction of Gene Silencing

It also is possible that genes may be introduced to produce novel transgenic plants which have reduced expression of a native gene product by the mechanism of co-suppression. It has been demonstrated in tobacco, tomato, and petunia (Goring et al., 1991; Smith et al., 1990; Napoli et al., 1990; van der Krol et al., 1990) that expression of the sense transcript of a native gene will reduce or eliminate expression of the native gene in a manner similar to that observed for antisense genes. The introduced gene may encode all or part of the targeted native protein but its translation may not be required for reduction of levels of that native protein.

4. Non-RNA-Expressing Sequences

DNA elements including those of transposable elements such as Ds, Ac, or Mu, may be inserted into a gene to cause mutations. These DNA elements may be inserted in order to inactivate (or activate) a gene and thereby "tag" a particular trait. In this instance the transposable element does not cause instability of the tagged mutation, because the utility of the element does not depend on its ability to move in the genome. Once a desired trait is tagged, the introduced DNA sequence may be used to clone the corresponding gene, e.g., using the introduced DNA sequence as a PCR primer together with PCR gene cloning techniques (Shapiro, 1983; Dellaporta et al., 1988). Once identified, the entire gene(s) for the particular trait, including control or regulatory regions where desired, may be isolated, cloned and manipulated as desired. The utility of DNA elements introduced into an organism for purposes of gene tagging is independent of the DNA sequence and does not depend on any biological activity of the DNA sequence, i.e., transcription into RNA or translation into protein. The sole function of the DNA element is to disrupt the DNA sequence of a gene.

It is contemplated that unexpressed DNA sequences, including novel synthetic sequences, could be introduced into cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labeled source. It is proposed that inclusion of label DNAs would enable one to distinguish proprietary germplasm or germplasm derived from such, from unlabelled germplasm.

Another possible element which may be introduced is a matrix attachment region element (MAR), such as the chicken lysozyme A element (Stief, 1989), which can be positioned around an expressible gene of interest to effect an increase in overall expression of the gene and diminish position dependent effects upon incorporation into the plant genome (Stief et al., 1989; Phi-Van et al., 1990).

5. Other

Other examples of non-protein expressing sequences specifically envisioned for use with the invention include tRNA sequences, for example, to alter codon usage, and rRNA variants, for example, which may confer resistance to various agents such as antibiotics.

XI. Biological Functional Equivalents

Modification and changes may be made in the centromeric DNA segments of the current invention and still obtain a functional molecule with desirable characteristics. The following is a discussion based upon changing the nucleic acids of a centromere to create an equivalent, or even an improved, second-generation molecule.

In particular embodiments of the invention, mutated centromeric sequences are contemplated to be useful for increasing the utility of the centromere. It is specifically contemplated that the function of the centromeres of the current invention may be based upon the secondary structure of the DNA sequences of the centromere, modification of the DNA with methyl groups or other adducts, and/or the proteins which interact with the centromere. By changing the DNA sequence of the centromere, one may alter the affinity of one or more centromere-associated protein(s) for the centromere and/or the secondary structure or modification of the centromeric sequences, thereby changing the activity of the centromere. Alternatively, changes may be made in the centromeres of the invention which do not affect the activity of the centromere. Changes in the centromeric sequences which reduce the size of the DNA segment needed to confer centromere activity are contemplated to be particularly useful in the current invention, as would changes which increased the fidelity with which the centromere was transmitted during mitosis and meiosis.

XII. Plants

The term "plant," as used herein, refers to any type of plant. The inventors have provided below an exemplary description of some plants that may be used with the invention. However, the list is not in any way limiting, as other types of plants will be known to those of skill in the art and could be used with the invention.

A common class of plants exploited in agriculture are vegetable crops, including artichokes, kohlrabi, arugula, leeks, asparagus, lettuce (e.g., head, leaf, romaine), bok choy, malanga, broccoli, melons (e.g., muskmelon, watermelon, crenshaw, honeydew, cantaloupe), brussels sprouts, cabbage, cardoni, carrots, napa, cauliflower, okra, onions, celery, parsley, chick peas, parsnips, chicory, chinese cabbage, peppers, collards, potatoes, cucumber plants (marrows, cucumbers), pumpkins, cucurbits, radishes, dry bulb onions, rutabaga, eggplant, salsify, escarole, shallots, endive, garlic, spinach, green onions, squash, greens, beet (sugar beet and fodder beet), sweet potatoes, Swiss chard, horseradish, tomatoes, kale, turnips, and spices.

Other types of plants frequently finding commercial use include fruit and vine crops such as apples, apricots, cherries, nectarines, peaches, pears, plums, prunes, quince almonds, chestnuts, filberts, pecans, pistachios, walnuts, citrus, blueberries, boysenberries, cranberries, currants, loganberries, raspberries, strawberries, blackberries, grapes, avocados, bananas, kiwi, persimmons, pomegranate, pineapple, tropical fruits, pomes, melon, mango, papaya, and lychee.

Many of the most widely grown plants are field crop plants such as evening primrose, meadow foam, corn (field, sweet, popcorn), hops, jojoba, peanuts, rice, safflower, small grains (barley, oats, rye, wheat, etc.), sorghum, tobacco, kapok, leguminous plants (beans, lentils, peas, soybeans), oil plants (rape, mustard, poppy, olives, sunflowers, coconut, castor oil plants, cocoa beans, groundnuts), fibre plants (cotton, flax, hemp, jute), lauraceae (cinnamon, camphor), or plants such as coffee, sugarcane, tea, and natural rubber plants.

Still other examples of plants include bedding plants such as flowers, cactus, succulents and ornamental plants, as well as trees such as forest broad-leaved trees and evergreens, such as conifers), fruit, ornamental, and nut-bearing trees, as well as shrubs and other nursery stock.

XIII. Definitions

As used herein, the terms "autonomous replicating sequence" or "ARS" or "origin of replication" refer to an origin of DNA replication recognized by proteins that initiate DNA replication.

As used herein, the terms "binary BAC" or "binary bacterial artificial chromosome" refer to a bacterial vector that contains the T-DNA border sequences necessary for *Agrobacterium* mediated transformation (see, for example, Hamilton et al., 1996; Hamilton, 1997; and Liu et al., 1999.

As used herein, the term "candidate centromere sequence" refers to a nucleic acid sequence which one wishes to assay for potential centromere function.

As used herein, a "centromere" is any DNA sequence that confers an ability to segregate to daughter cells through cell division. In one context, this sequence may produce a segregation efficiency to daughter cells ranging from about 1% to about 100%, including to about 5%, 10%, 20%, 30%, 40%, 50%, 60%, 70%, 80%, 90% or about 95% of daughter cells. Variations in such a segregation efficiency may find important applications within the scope of the invention; for example, minichromosomes carrying centromeres that confer 100% stability could be maintained in all daughter cells without selection, while those that confer 1% stability could be temporarily introduced into a transgenic organism, but be eliminated when desired. In particular embodiments of the invention, the centromere may confer stable segregation of a nucleic acid sequence, including a recombinant construct comprising the centromere, through mitotic or meiotic divisions, including through both meiotic and meitotic divisions. A plant centromere is not necessarily derived from plants, but has the ability to promote DNA segregation in plant cells.

As used herein, the term "centromere-associated protein" refers to a protein encoded by a sequence of the centromere or a protein which is encoded by host DNA and binds with relatively high affinity to the centromere.

As used herein, the term "circular permutations" refer to variants of a sequence that begin at base n within the sequence, proceed to the end of the sequence, resume with base number one of the sequence, and proceed to base n−1. For this analysis, n may be any number less than or equal to the length of the sequence. For example, circular permutations of the sequence ABCD are: ABCD, BCDA, CDAB, and DABC.

As used herein, the term "crop" includes any plant or portion of a plant grown or harvested for commercial or beneficial purposes.

As used herein, "eukaryote" refers to living organisms whose cells contain nuclei. A eukaryote may be distinguished from a "prokaryote" which is an organism which lacks nuclei. Prokaryotes and eukaryotes differ fundamentally in the way their genetic information is organized, as well as their patterns of RNA and protein synthesis.

As used herein, the term "expression" refers to the process by which a structural gene produces an RNA molecule, typically termed messenger RNA (mRNA). The mRNA is typically, but not always, translated into polypeptide(s).

As used herein, the term "genome" refers to all of the genes and DNA sequences that comprise the genetic information within a given cell of an organism. Usually, this is taken to mean the information contained within the nucleus, but also includes the organelles.

As used herein, the term "higher eukaryote" means a multicellular eukaryote, typically characterized by its greater complex physiological mechanisms and relatively large size. Generally, complex organisms such as plants and animals are included in this category. Preferred higher eukaryotes to be transformed by the present invention include, for example, monocot and dicot angiosperm species, gymnosperm species, fern species, plant tissue culture cells of these species, animal cells and algal cells. It will of course be understood that prokaryotes and eukaryotes alike may be transformed by the methods of this invention.

As used herein, the term "host" refers to any organism that contains a plasmid, expression vector, or integrated construct comprising a plant centromere. Preferred examples of host cells for cloning, useful in the present invention, are bacteria such as *Escherichia coli, Bacillus subtilis, Pseudomonas, Streptomyces, Salmonella*, and yeast cells such as *S. cerevisiae*. Host cells which can be targeted for expression of a minichromosome may be plant cells of any source and specifically include *Arabidopsis*, maize, rice, sugarcane, sorghum, barley, soybeans, tobacco, wheat, tomato, potato, citrus, or any other agronomically or scientifically important species.

As used herein, the term "hybridization" refers to the pairing of complementary RNA and DNA strands to produce an RNA-DNA hybrid, or alternatively, the pairing of two DNA single strands from genetically different or the same sources to produce a double stranded DNA molecule.

As used herein, the term "linker" refers to a DNA molecule, generally up to 50 or 60 nucleotides long and synthesized chemically, or cloned from other vectors. In a preferred embodiment, this fragment contains one, or preferably more than one, restriction enzyme site for a blunt-cutting enzyme and a staggered-cutting enzyme, such as BamHI. One end of the linker fragment is adapted to be ligatable to one end of the linear molecule and the other end is adapted to be ligatable to the other end of the linear molecule.

As used herein, a "library" is a pool of random DNA fragments which are cloned. In principle, any gene can be isolated by screening the library with a specific hybridization probe (see, for example, Young et al., 1977). Each library may contain the DNA of a given organism inserted as discrete restriction enzyme-generated fragments or as randomly sheered fragments into many thousands of plasmid vectors. For purposes of the present invention, *E. coli*, yeast, and *Salmonella* plasmids are particularly useful when the genome inserts come from other organisms.

As used herein, the term "lower eukaryote" refers to a eukaryote characterized by a comparatively simple physiology and composition, and most often unicellularity. Examples of lower eukaryotes include flagellates, ciliates, and yeast.

As used herein, a "minichromosome" is a recombinant DNA construct including a centromere and capable of transmission to daughter cells. Minichromosome may remain separate from the host genome (as episomes) or may integrate into host chromosomes. The stability of this construct through cell division could range between from about 1% to about 100%, including about 5%, 10%, 20%, 30%, 40%, 50%, 60%, 70%, 80%, 90% and about 95%. The minichromosome construct may be a circular or linear molecule. It may include elements such as one or more telomeres, ARS sequences, and genes. The number of such sequences included is only limited by the physical size limitations of the construct itself. It could contain DNA derived from a natural centromere, although it may be preferable to limit the amount of DNA to the minimal amount required to obtain a segregation efficiency in the range of 1–100%. The minichromosome could also contain a synthetic centromere composed of tandem arrays of repeats of any sequence, either derived from a natural centromere, or of synthetic DNA. The minichromosome could also contain DNA derived from multiple natural centromeres. The minichromosome may be inherited through mitosis or meiosis, or through both meiosis and mitosis. As used herein, the term minichromosome specifically encompasses and includes the terms "plant artificial chromosome" or "PLAC," or engineered chromosomes or microchromosomes and all teachings relevant to a PLAC or plant artificial chromosome specifically apply to constructs within the meaning of the term minichromosome.

As used herein, by "minichromosome-encoded protein" it is meant a polypeptide which is encoded by a sequence of a minichromosome of the current invention. This includes sequences such as selectable markers, telomeres, etc., as well as those proteins encoded by any other selected functional genes on the minichromosome.

As used herein, the term "plant" includes plant cells, plant protoplasts, plant calli, and the like, as well as whole plants regenerated therefrom.

As used herein, the term "plasmid" or "cloning vector" refers to a closed covalently circular extrachromosomal DNA or linear DNA which is able to replicate in a host cell and which is normally nonessential to the survival of the cell. A wide variety of plasmids and other vectors are known and commonly used in the art (see, for example, Cohen et al., U.S. Pat. No. 4,468,464, which discloses examples of DNA plasmids, and which is specifically incorporated herein by reference).

As used herein, a "probe" is any biochemical reagent (usually tagged in some way for ease of identification), used to identify or isolate a gene, a gene product, a DNA segment or a protein.

As used herein, the term "recombination" refers to any genetic exchange that involves breaking and rejoining of DNA strands.

As used herein the term "regulatory sequence" refers to any DNA sequence that influences the efficiency of transcription or translation of any gene. The term includes, but is not limited to, sequences comprising promoters, enhancers and terminators.

As used herein, a "selectable marker" is a gene whose presence results in a clear phenotype, and most often a growth advantage for cells that contain the marker. This growth advantage may be present under standard conditions, altered conditions such as elevated temperature, or in the presence of certain chemicals such as herbicides or antibiotics. Use of selectable markers is described, for example, in Broach et al. (1979). Examples of selectable markers include the thymidine kinase gene, the cellular adenine-phosphoribosyltransferase gene and the dihydrylfolate reductase gene, hygromycin phosphotransferase genes, the bar gene and neomycin phosphotransferase genes, among others. Preferred selectable markers in the present invention include genes whose expression confer antibiotic or herbicide resistance to the host cell, sufficient to enable the maintenance of a vector within the host cell, and which facilitate the manipulation of the plasmid into new host cells. Of particular interest in the present invention are proteins conferring cellular resistance to ampicillin, chloramphenicol, tetracycline, G-418, bialaphos, and glyphosate for example.

As used herein, a "screenable marker" is a gene whose presence results in an identifiable phenotype. This phenotype may be observable under standard conditions, altered conditions such as elevated temperature, or in the presence of certain chemicals used to detect the phenotype.

As used herein, the term "site-specific recombination" refers to any genetic exchange that involves breaking and rejoining of DNA strands at a specific DNA sequence.

As used herein, a "structural gene" is a sequence which codes for a polypeptide or RNA and includes 5' and 3' ends. The structural gene may be from the host into which the structural gene is transformed or from another species. A structural gene will preferably, but not necessarily, include one or more regulatory sequences which modulate the expression of the structural gene, such as a promoter, terminator or enhancer. A structural gene will preferably, but not necessarily, confer some useful phenotype upon an organism comprising the structural gene, for example, herbicide resistance. In one embodiment of the invention, a structural gene may encode an RNA sequence which is not translated into a protein, for example a tRNA or rRNA gene.

As used herein, the term "telomere" refers to a sequence capable of capping the ends of a chromosome, thereby preventing degradation of the chromosome end, ensuring replication and preventing fusion to other chromosome sequences. Telomeres can include naturally occuring telomere sequences or synthetic sequences. Telomres from one species may confer telomere activity in another species.

As used herein, the terms "transformation" or "transfection" refer to the acquisition in cells of new DNA sequences through the chromosomal or extra-chromosomal addition of DNA. This is the process by which naked DNA, DNA coated with protein, or whole minichromosomes are introduced into a cell, resulting in a potentially heritable change.

As used herein the term "consensus" refers to a nucleic acid sequence derived by comparing two or more related sequences. A consensus sequence defines both the conserved and variable sites between the sequences being compared. Any one of the sequences used to derive the consensus or any permutation defined by the consensus may be useful in construction minichromosomes.

As used herein the term "repeated nucleotide sequence" refers to any nucleic acid sequence of at least 25 bp present in a genome or a recombinant molecule that occurs at least two or more times and that are preferably at least 80% identical either in head to tail or head to head orientation either with or without intervening sequence between repeat units.

XIV. EXAMPLES

The following examples are included to demonstrate preferred embodiments of the invention. It should be appreciated by those of skilled the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Isolation of Genomic DNA

Tissue from various plants are harvested for DNA extraction. For DNA extraction, leaf tissue is cooled in liquid nitrogen, ground to a fine powder and transferred to an organic solvent-resistant test tube or beaker. Warm CTAB extraction solution (2% (w/v) CTAB, 100 mM Tris-Cl, pH 9.5, 20 mM EDTA, pH 8.0, 1.4 M NaCl, 1% polyethylene gycol) is added in a ratio of 20 ml per gram of tissue and mixed thoroughly. For each 20 ml extraction buffer, 50 microliters of β-mercaptoethanol and 30 microliters of 30 mg/ml RNAse A are added and the mixture is incubated for 10–60 min. at 65° C. with occasional mixing. The homogenate is extracted with an equal volume of chloroform, and is then centrifuged 5 min at 7500×g (8000 rpm in JA20; 10,000 rpm in a microcentrifuge, for smaller samples), 4° C. The top (aqueous) phase is recovered and nucleic acids are precipitated by adding 1 volume isopropanol. After mixing, the precipitate is pelleted at 15 min at 7500×g, 4° C. The pellet is washed with 70% ethanol, dried and resuspended in a minimal volume of TE (10 mM Tris-Cl, pH 8.0, 0.1 mM EDTA, pH 8.0).

Example 2

Brassica oleracea Centromere Repeat Sequences

We purified repetitive sequences from *Brassica oleracea* (*Brassica oleracea* fast plants, obtained from the Wisconsin Crucifer Cooperative). We set forth herein two centromere repeats, termed ChrBo1 and ChrBo2. We determined the consensus of each repeat as described in Example 6.

The consensus sequence of ChrBo1 is shown in FIG. 1A (SEQ ID NO:1). This consensus was assembled from DNA sequences collected by the inventors. Twenty-four of these sequences completely spanned the repeat, and nine others partially covered the repeat. The length of this repeat is 180±0.86 base pairs, and A and T comprise of 60% of the consensus.

The consensus sequence of ChrBo2 is shown in FIG. 1B (SEQ ID NO:2). This consensus was assembled from DNA sequences collected by the inventors. Five of these sequences completely spanned the repeat, and two others partially covered the repeat. The length of this repeat is 180±0.45 base pairs, and A and T comprise 63% of the consensus.

The two repeats (ChrBo1 and ChrBo2) were aligned to each other using the ClustalX program (ClustalX is a free multiple sequence alignment program for Windows. Thompson, J. D., Gibson, T. J., Plewniak, F., Jeanmougin, F. and Higgins, D. G. (1997) The ClustalX windows interface: flexible strategies for multiple sequence alignment aided by quality analysis tools. Nucleic Acids Research, 24:4876–4882.). The two consensus sequences differ significantly from each other at several bases. Those sites with significant differences (chi-squared, $P<0.05$) are highlighted as shown in FIG. 1C.

The GenBank nt database (National Center for Biotechnology Information Web Site) and the plant satellite DNA database (PlantSat: A Database of Plant Satellite DNA Web Site) were compared to the inventors' consensus sequences using the blastn program and an Expect value threshold score of −3. Consensus sequences were assembled using all inventors' and GenBank sequences that matched with an Expect (E) value of less than −45.

The revised consensus sequence of ChrBo1 is shown in FIG. 1D (SEQ ID NO:3). This consensus was assembled from thirty-three DNA sequences collected by the inventors and eighteen GenBank sequences (Table 10). Thirty of these sequences completely spanned the repeat, and twenty-one others partially covered the repeat. The length of this repeat is 180±0.81 base pairs, and A and T comprise of 59% of the consensus.

TABLE 1

GenBank sequences (accession numbers) that match inventors' ChrBo1 consensus

| | | | |
|---|---|---|---|
| M30962 | M30963 | M31436 | M31435 |
| M31438 | M31434 | M31439 | M31437 |
| X68786 | X12736 | X07519 | X16589 |
| X15291 | X68783 | X68784 | X61583 |
| AJ228348 | Z22947 | | |

The revised consensus sequence of ChrBo2 is shown in FIG. 1E (SEQ ID NO:4). This consensus was assembled from seven DNA sequences collected by the inventors and five GenBank sequences (Table 2). Seven of these sequences completely spanned the repeat, and five others partially covered the repeat. The length of this repeat is 180±0.44 base pairs, and A and T comprise of 63% of the consensus.

TABLE 2

GenBank sequences (accession numbers) that match inventors' ChrBo2 consensus

| | | |
|---|---|---|
| AJ228347 | M30962 | X12736 |
| X61583 | X68785 | |

The two revised consensus sequences (ChrBo1 and ChrBo2) were aligned to each other using the ClustalX program. The two consensus sequences differ significantly (chi-squared, $P<0.05$) from each other at several bases (highlighted as shown in FIG. 1F).

A total of 20 GenBank entries match the *Brassica oleracea* centromere sequences defined by the inventors. These are annotated as follows:
Xle7-2EB gene
Xle4-7B gene
Xle6-14H gene
Satellite tandem repeat monomer
HindIII satellite repeat
Satellite DNA inverted direct repeat
Tandem repeated DNA
Highly repetitive DNA
They are not annotated as centromere repeats in GenBank. A completed list of these sequences are shown in Table 3.

TABLE 3

GenBank entries match the *Brassica oleracea* centromere sequences defined by the inventors

| GenBank Accession No. | Annotation | Repeat | Position | No. of base pairs | % Identity |
|---|---|---|---|---|---|
| X68786 | *B. juncea* Xle7-2EB gene | Complete | 472–651 | 180 | 97 |
| X68786 | *B. juncea* Xle7-2EB gene | Complete | 763–942 | 180 | 94 |
| X68786 | *B. juncea* Xle7-2EB gene | Partial | 648–761 | 115 | 96 |

TABLE 3-continued

GenBank entries match the *Brassica oleracea* centromere sequences defined by the inventors

| GenBank Accession No. | Annotation | Repeat | Position | No. of base pairs | % Identity |
|---|---|---|---|---|---|
| X12736 | *B. campestries* DNA for satellite tandem repeat monomer (consensus sequence) | Complete | 181–2 | 180 | 97 |
| X07519 | Wild cabbage satellite DNA | Complete | 179–1 | 179 | 97 |
| X61583 | *B. napus* Canrep highly repetitive DNA | Complete | 2–173 | 176 | 98 |
| X68783 | *B. juncea* repetitive DNA sequence canrep subfamily A | Partial | 2–173 | 172 | 97 |
| X68784 | *B. juncea* Xle4-7B gene | Complete | 983–1162 | 180 | 95 |
| X68784 | *B. juncea* Xle4-7B gene | Partial | 815–986 | 172 | 94 |
| AJ228348 | *B. carinata* DNA, HindIII satellite repeat (clone pBcar3) | Partial | 2–173 | 172 | 96 |
| M31438 | *B. oleracea* satellite DNA inverted direct repeat | Partial | 176–1 | 176 | 94 |
| X16589 | *B. nigra* tandem repeat DNA (clone BN1G 9, BN1G 23, BG1G 14) | Partial | 177–1 | 177 | 94 |
| M31434 | *B. oleracea* satellite DNA inverted direct repeat | Partial | 176–8 | 169 | 95 |
| M31437 | *B. oleracea* satellite DNA inverted direct repeat | Partial | 175–1 | 175 | 94 |
| M30963 | *B. juncea* tandemly repeated DNA | Complete | 181–2 | 180 | 93 |
| M31435 | *B. oleracea* satellite DNA inverted direct repeat | Partial | 174–8 | 169 | 94 |
| M31436 | *B. oleracea* satellite DNA inverted direct repeat | Partial | 175–1 | 177 | 94 |
| X15291 | *B. juncea* satellite DNA | Partial | 1–161 | 161 | 95 |
| M31439 | *B. oleracea* satellite DNA inverted direct repeat | Partial | 176–1 | 177 | 90 |
| Z22947 | *B. campestris* satellite DNA | Partial | 181–347 | 170 | 90 |
| Z22947 | *B. campestris* satellite DNA | Partial | 2–179 | 178 | 89 |
| M30962 | *B. campestris* tandemly repeated DNA | Complete | 181–2 | 180 | 87 |
| X68785 | *B. juncea* Xle6-14H gene | Complete | 580–758 | 180 | 92 |
| X68785 | *B. juncea* Xle6-14H gene | Partial | 404–568 | 165 | 90 |
| AJ228347 | *B. carinata* DNA, HindIII satellite repeat (clone pBcar5) | Partial | 177–2 | 176 | 90 |

Example 3

*Glycine max* Centromere Repeat Sequences

We purified repetitive sequences from soybean (*Glycine max*, variety Williams 82), and set forth herein two centromere repeats, termed ChrGm1 and ChrGm2. We determined the consensus of each repeat as shown in Example 6.

The consensus sequence for ChrGm1 is shown in FIG. 2A (SEQ ID NO:5). This consensus was assembled from DNA sequences collected by the inventors. Seven of these sequences completely spanned the repeat, and twenty-five others partially covered the repeat. It is 92±0.79 base pairs in length, and A and T comprise of 63% of the consensus.

The consensus sequence for ChrGm2 is shown in FIG. 2B (SEQ ID NO:6). This consensus was assembled from DNA sequences collected by the inventors. Ten of these sequences completely spanned the repeat, and eleven others partially covered the repeat. It is 91±0.48 base pairs in length, and A and T comprise of 62% of the consensus.

The two repeats (ChrGm1 and ChrGm2) were aligned to each other using the ClustalX program Those sites which differ significantly from each other (chi-squared, $P<0.05$) are highlighted in FIG. 2C.

The GenBank nt database (National Center for Biotechnology Information Web Site) and the plant satellite DNA database PlantSat: A Database of Plant Satellite DNA Web Site) were compared to the inventors' consensus sequences using the blastn program and an Expect value threshold of −3. Consensus sequences were built using all inventors' and GenBank sequences that matched with an Expect (E) value of less than −25.

The revised consensus sequence for ChrGm1 is shown in FIG. 2D (SEQ ID NO:7). This consensus was assembled from thirty-two DNA sequences collected by the inventors and one matching sequence from GenBank (accession number Z26334). Eight of these sequences completely spanned the repeat, and twenty-five others partially covered the repeat. It is 92±0.74 base pairs in length, and A and T comprise of 56% of the consensus.

The revised consensus sequence for ChrGm2 is shown in FIG. 2E (SEQ ID NO:8). This consensus was assembled from twenty-one DNA sequences collected by the inventors and three matching sequences from GenBank (accession numbers AF297983, AF297984, AF297985). Ten of these sequences completely spanned the repeat, and fourteen others partially covered the repeat. It is 91±0.53 base pairs in length, and A and T comprise of 61% of the consensus.

The two repeats (ChrGm1 and ChrGm2) were aligned to each other using the ClustalX program Those sites with significant differences (chi-squared, $P<0.05$) are highlighted in FIG. 2F.

A total of 4 GenBank entries match the *Glycine max* centromere sequences defined by the inventors. These are annotated as follows:

Satellite DNA

Tospovirus resistance protein C (Sw5-c), tospovirus resistance protein D (Sw5-d), and tospovirus resistance protein E (Sw5-e) genes They are not annotated as centromere repeats in GenBank. A complete list of these sequences is shown in Table 4:

TABLE 4

GenBank entries match the *Glycine max* centromere sequences defined by the inventors

| GenBank Accession No. | Annotation | Repeat | Position | No. of base pairs | % Identity |
|---|---|---|---|---|---|
| Z26334 | *G. max* satellite DNA | Complete | 92–1 | 92 | 95 |
| AF297985 | *G. max* clone TRS3 tandem repetitive repeat region | Partial | 259–173 | 87 | 93 |
| AF297985 | *G. max* clone TRS3 tandem repetitive repeat region | Partial | 78–3 | 76 | 94 |
| AF297985 | *G. max* clone TRS3 tandem repetitive repeat region | Partial | 168–83 | 86 | 90 |
| AF297984 | *G. max* clone TRS2 tandem repetitive repeat region | Partial | 170–84 | 87 | 91 |
| AF297984 | *G. max* clone TRS2 tandem repetitive repeat region | Partial | 260–175 | 86 | 88 |
| AF297984 | *G. max* clone TRS2 tandem repetitive repeat region | Partial | 79–3 | 77 | 89 |
| AF297983 | *G. max* clone TRS1 tandem repetitive repeat region | Partial | 77–3 | 75 | 94 |

Example 4

*Lycopersicon esculentum* Centromere Repeat Sequences

We purified repetitive sequences from tomato (*Lycopersicon esculentum*, variety Microtom) and set forth herein one centromere repeat. We determined the consensus of this repeat as shown in Example 6.

The consensus sequence of ChrLe1 is shown in FIG. 3A (SEQ ID NO:9). This consensus was assembled from forty-two DNA sequences collected by the inventors. Eighteen of these sequences completely spanned the repeat, and twenty-four others partially covered the repeat. The repeat is 181±0.61 base pairs in length, and A and T comprise of 50% of the consensus.

The GenBank nt database (National Center for Biotechnology Information Web Site) and the plant satellite DNA database PlantSat: A Database of Plant Satellite DNA Web Site) were compared to the inventors' consensus sequences using the blastn program and an Expect value threshold value of −3. Consensus sequences were built using all inventors' and GenBank sequences matched with an Expect (E) value of less than −40.

We determined the consensus of this repeat. The repeat is 181±0.61 base pairs in length, and A and T comprise of 50% of the consensus.

The revised consensus sequence of ChrLe1 is shown in FIG. 3B (SEQ ID NO:10). This consensus was assembled from forty-two sequences collected by the inventors and two GenBank sequence (nt database at fttp://ftp.ncbi.nlm.nih.gov/blast/db/. March 29 version, downloaded on Apr. 7, 2002). Eighteen of these sequences completely spanned the repeat, and twenty-six others partially covered the repeat. The GenBank sequences are accession numbers X87233 and AY007367.

Neither of the 2 GenBank entries that match the *Lycopersicon esculentum* centromere sequences defined by the inventors are complete repeats; they match only a portion of the sequence identified by the company. These are annotated as follows:

Satellite DNA
Tandem Repetitive Repeat Region

They are not annotated as centromere repeats in GenBank. A complete list of these sequences is shown in Table 5.

TABLE 5

GenBank entries match the *Lycopersicon esculentum* centromere sequences defined by the inventors

| GenBank Accession No. | Annotation | Repeat | Position | No. of base pairs | % Identity |
|---|---|---|---|---|---|
| X87233 | *L. esculentum* satellite DNA | Partial | 163–1 | 161 | 93 |
| AY007367 | *L. esculentum* tospovirus resistance protein C (Sw5-c), tospovirus resistance protein D (Sw5-d), and tospovirus resistance protein E (Sw5-e) genes | Partial | 12003–12156 | 154 | 93 |
| AY007367 | *L. esculentum* tospovirus resistance protein C (Sw5-c), tospovirus resistance protein D (Sw5-d), and tospovirus resistance protein E (Sw5-e) genes | Partial | 12184–12344 | 161 | 90 |
| AY007367 | *L. esculentum* tospovirus resistance protein C (Sw5-c), tospovirus resistance protein D (Sw5-d), and tospovirus resistance protein E (Sw5-e) genes | Partial | 12546–12700 | 155 | 90 |
| AY007367 | *L. esculentum* tospovirus resistance protein C (Sw5-c), tospovirus resistance protein D (Sw5-d), and tospovirus resistance protein E (Sw5-e) genes | Partial | 12365–12526 | 157 | 89 |

Example 5

*Zea mays* Centromere Repeat Sequences

We purified repetitive sequences from corn (*Zea mays*, variety B73), and set forth herein one centromere repeat, termed ChrZm1. We determined the consensus of the repeat as shown in Example 5. The repeat is 180±1.15 base pairs in length, and A and T comprise of 56% of the consensus.

The consensus sequence of ChrZm1 is shown in FIG. 4A (SEQ ID NO:11). This consensus was assembled from thirty-eight DNA sequences collected by the inventors. Three of these sequences completely spanned the repeat, and thirty-five others partially covered the repeat.

The GenBank nt database (National Center for Biotechnology Information Web Site) and the plant satellite DNA database PlantSat: A Database of Plant Satellite DNA Web Site) were compared to the inventors' consensus sequences using the blastn program and an Expect value threshold score of −3. Consensus sequences were built using all inventors' and GenBank sequences matched with an Expect (E) value of −50.

The revised consensus sequence of ChrZm1 is shown in FIG. 4B (SEQ ID NO:12). This consensus was assembled from thirty-eight DNA sequences collected by the inventors and twenty-six matching GenBank sequences (Table 6). Twenty of these sequences completely spanned the repeat, and forty-four others partially covered the repeat. The length of the repeat is 180±0.51 base pairs, and A and T comprise the consensus.

TABLE 6

GenBank sequences that match the inventors' ChrZm1 consensus

| | | | | | |
|---|---|---|---|---|---|
| M32521 | M32522 | M32523 | M32524 | M32525 | M32526 |
| M32527 | M32528 | M32529 | M32530 | M32531 | M32532 |
| M32533 | M32534 | M325375 | M32536 | M32537 | M32538 |
| M35408 | AF030934 | AF030935 | AF030936 | AF030937 | AF030938 |
| AF030939 | AF030940 | | | | |

A total of 26 GenBank entries match the *Zea mays* centromere sequences defined by the inventors. These are annotated as follows:

180-bp knob-specific repeat region heterochromatin repetitive DNA

They are not annotated as centromere repeats in GenBank. A complete list of these sequences is shown in Table 7.

TABLE 7

GenBank entries match the *Lycopersicon esculentum* centromere sequences defined by the inventors

| GenBank Accession No. | Annotation | Repeat | Position | No. of base pairs | % Identity |
|---|---|---|---|---|---|
| M32522 | Maize 180-bp knob-specific repeat region | Complete | 1–180 | 180 | 96 |
| M32521 | Maize 180-bp knob-specific repeat region | Complete | 1–180 | 180 | 96 |
| M32533 | Z. mays subsp. mexicana 180-bp knob-specific repeat region | Complete | 1–180 | 180 | 96 |
| M32525 | Maize 180-bp knob-specific repeat region | Complete | 1–180 | 180 | 96 |
| M32524 | Maize 180-bp knob-specific repeat region | Complete | 1–180 | 180 | 96 |
| M32523 | Maize 180-bp knob-specific repeat region | Complete | 1–180 | 180 | 96 |
| M35408 | Corn heterochromatin repetitive DNA | Complete | 1–180 | 180 | 96 |
| M32526 | Maize 180-bp knob-specific repeat region | Complete | 1–180 | 180 | 95 |
| AF030939 | Z. mays 180-bp knob-associated tandem repeat 15-T3-2 | Complete | 1–180 | 180 | 95 |
| M32528 | Maize 180-bp knob-specific repeat region | Complete | 1–180 | 180 | 95 |
| M32534 | Z. mays subsp. mexicana 180-bp knob-specific repeat region | Complete | 1–180 | 180 | 94 |
| M32527 | Maize 180-bp knob-specific repeat region | Partial | 8–179 | 172 | 95 |
| M32538 | T. dactyloides (Tripsacum dactyloides, gama grass) 180-bp knob-specific repeat region | Complete | 1–179 | 179 | 94 |
| M32529 | Maize 180-bp knob-specific repeat region | Complete | 1–180 | 180 | 93 |
| AF030938 | Z. mays 180-bp knob-associated tandem repeat 15-T3-1 | Partial | 4–180 | 177 | 93 |
| M32532 | Maize 180-bp knob-specific repeat region | Complete | 1–180 | 180 | 93 |
| AF030937 | Z. mays 180-bp knob-associated tandem repeat 1-T7-2 | Complete | 1–180 | 180 | 92 |
| AF030940 | Z. mays 180-bp knob-associated tandem repeat 15-T7-1 | Complete | 1–180 | 180 | 92 |
| AF030936 | Z. mays 180-bp knob-associated tandem repeat 1-T7-1 | Partial | 10–180 | 172 | 93 |
| M32537 | T. dactyloides 180-bp knob-specific repeat region | Complete | 1–180 | 180 | 92 |
| M32530 | Maize 180-bp knob-specific repeat region | Complete | 1–180 | 180 | 92 |
| M32531 | Maize 180-bp knob-specific repeat region | Complete | 1–179, introduced one gap | 180 | 91 |
| AF030935 | Z. mays 180-bp knob-associated tandem repeat 1-T3-2 | Partial | 1–175 | 175 | 90 |
| AF030934 | Z. mays 180-bp knob-associated tandem repeat 1-T3-1 | Partial | 47–201 | 155 | 92 |
| M32536 | T. dactyloides 180-bp knob-specific repeat region | Complete | 1–180 | 180 | 94 |
| M32535 | T. dactyloides 180-bp knob-specific repeat region | Complete | 1–177, 2% gaps | 177 | 91 |

Six GenBank sequences of *Zea mays* centrometric repeat CentC were collected (Table 13) and assigned the identifier ChrZm2. The consensus of the repeat was determined as shown in Example 6. The repeat is 158±1.6 base pairs in length. A and T comprises of 53% of the bases. All 6 sequences are of unit length.

The consensus sequence of ChrZm2 (SEQ ID NO:13) is shown in FIG. 4C.

TABLE 8

GenBank sequences of Zea mays centrometric repeat ChrZm2

| AF078918 | AF078919 | AF078920 |
| AF0789121 | AF078922 | AF078923 |

Example 6

Determining Consensus Sequences

Sequences were first aligned and edited in Vector NTI suite7 (InforMax, 7600 Wisconsin Ave., Suite 1100, Bethesda, Md. 20814) and exported as a fasta file. A perl program, consensus.pl, was written and used to determine the consensus for each position within the repeats based on the following rules:

The most common base is designated as the consensus if it occurs three times more frequently than the second most common base.

If the occurrence of the most common base is not three times more frequent than the second most common base, but the combined frequency of the two most common bases is three times that of the third most common base, and the frequency of the second most common base is greater than the frequency of the third most common base, then the second and first bases are together considered as a consensus polymorphism, and designated using the IUPAC codes (M=A or C, R=A or G, W=A or T, S=C or G, Y=C or T, k=G or T, V=A or C or G, H=A or C or T, D=A or G or T, B=C or G or T, N=G or T or C or A).

If the combined frequency of the two most common bases is not three times greater than that of the third most common base, but the combined frequency of the three most common bases is three times that of the fourth most common base, and the third most common base is more common than the fourth most common base, and the frequency of occurrence of the fourth base is less than or equal to 22%, the consensus is assigned according to the IUPAC ambiguity codes for the three most common bases. If the four bases occur approximately equally (23–27%), the consensus is assigned as N.

Example 7

Constructing BAC Vectors for Testing Centromere Function

A BAC clone may be retrofitted with one or more plant telomeres and selectable markers together with the DNA elements necessary for *Agrobacterium* transformation (FIG. 9). This method will provide a means to deliver any BAC clone into plant cells and to test it for centromere function.

The method works in the following way. The conversion vector contains a retrofitting cassette. The retrofitting cassette is flanked by Tn10, Tn5, Tn7, Mu or other transposable elements and contains an origin of replication and a selectable marker for *Agrobacterium*, a plant telomere array followed by T-DNA right and left borders followed by a second plant telomere array and a plant selectable marker (FIG. 9). The conversion vector is transformed into an *E. coli* strain carrying the target BAC. The transposable elements flanking the retrofitting cassette then mediate transposition of the cassette randomly into the BAC clone. The retrofitted BAC clone can now be transformed into an appropriate strain of *Agrobacterium* and then into plant cells where it can be tested for high fidelity meiotic and mitotic transmission which would indicate that the clone contained a complete functional plant centromere.

Example 8

Sequence Analysis of *Arabidopsis* Centromeres

A. Abundance of Genes in the Centromeric Regions

Expressed genes are located within 1 kb of essential centromere sequences in *S. cerevisiae*, and multiple copies of tRNA genes reside within an 80 kb fragment necessary for centromere function in *S. pombe* (Kuhn et al., 1991). In contrast, genes are thought to be relatively rare in the centromeres of higher eukaryotes, though there are notable exceptions. The *Drosophila* light, concertina, responder, and rolled loci all map to the centromeric region of chromosome 2, and translocations that remove light from its native heterochromatic context inhibit gene expression. In contrast, many *Drosophila* and human genes that normally reside in euchromatin become inactive when they are inserted near a centromere. Thus, genes that reside near centromeres likely have special control elements that allow expression (Karpen, 1994; Lohe and Hilliker, 1995). The sequences of *Arabidopsis* CEN2 and CEN4, provided herein, provide a powerful resource for understanding how gene density and expression correlate with centromere position and associated chromatin.

Annotation of chromosome II and IV (National Center for Biotechnology Information Web Site) identified many genes within and adjacent to CEN2 and CEN4 (FIG. 8, FIGS. 11A–11T). The density of predicted genes on *Arabidopsis* chromosome arms averages 25 per 100 kb, and in the repeat-rich regions flanking CEN2 and CEN4 this decreases to 9 and 7 genes per 100 kb, respectively (Bevan et al., 1999). Many predicted genes also reside within the recombination-deficient, genetically-defined centromeres. Within CEN2, there were 5 predicted genes per 100 kb; while CEN4 was strikingly different, with 12 genes per 100 kb.

There was strong evidence that several of the predicted centromeric genes are transcribed. The phosphoenolpyruvate gene (CUE1) defines one CEN5 border; mutations in this gene cause defects in light-regulated gene expression (Li et al., 1995). Within the sequenced portions of CEN2 and CEN4, 17% (27/160) of the predicted genes shared >95% identity with cloned cDNAs (ESTs), with three-fold more matches in CEN4 than in CEN2 (TIGR: The Institute of Genomic Research Web Site). Twenty-four of these genes have multiple exons, and four correspond to single-copy genes with known functions. A list of the predicted genes identified is given in Table 9, below. A list of additional genes encoded within the boundaries of CEN4 are listed in Table 10. The identification of these genes is significant in that the genes may themselves contain unique regulatory elements or may reside in genomic locations flanking unique control or regulatory elements involved in centromere function or gene expression. In particular, the current inventors contemplate use of these genes, or DNA sequences 0 to 5 kb upstream or downstream of these sequences, for insertion into a gene of choice in a minichromosome. It is expected that such elements could potentially yield beneficial regulatory controls of the expression of these genes, even when in the unique environment of a centromere.

To investigate whether the remaining 23 genes were uniquely encoded at the centromere, a search was made in the database of annotated genomic *Arabidopsis* sequences. With the exception of two genes, no homologs with >95% identity were found elsewhere in the 80% of the genome that has been sequenced. The number of independent cDNA clones that correspond to a single-copy gene provides an estimate of the level of gene expression. On chromosome II, predicted genes with high quality matches to the cDNA database (>95% identity) match an average of four independent cDNA clones (range 1–78). Within CEN2 and CEN4, 11/27 genes exceed this average (Table 9). Finally, genes encoded at CEN2 and CEN4 are not members of a single gene family, nor do they correspond to genes predicted to play a role in centromere functions, but instead have diverse roles.

Many genes in the *Arabidopsis* centromeric regions are nonfunctional due to early stop codons or disrupted open reading frames, but few pseudogenes were found on the chromosome arms. Though a large fraction of these pseudogenes have homology to mobile elements, many correspond to genes that are typically not mobile (FIGS. 11I–J and FIGS. 11S–T). Within the genetically-defined centromeres there were 1.0 (CEN2) and 0.7 (CEN4) of these nonmobile pseudogenes per 100 kb; the repeat-rich regions bordering the centromeres have 1.5 and 0.9 per 100 kb respectively. The distributions of pseudogenes and transposable elements are overlapping, indicting that DNA insertions in these regions contributed to gene disruptions.

TABLE 9

Predicted genes within CEN2 and CEN4 that correspond to the cDNA database.

| Putative function | GenBank protein accession | # of EST matches* |
|---|---|---|
| CEN2 | | |
| Unknown | AAC69124 | 1 |
| SH3 domain protein | AAD15528 | 5 |
| Unknown | AAD15529 | 1 |
| unknown† | AAD37022 | 1 |
| RNA helicase‡ | AAC26676 | 2 |
| 40S ribosomal protein S16 | AAD22696 | 9 |
| CEN4 | | |
| Unknown | AAD36948 | 1 |
| Unknown | AAD36947 | 4 |
| leucyl tRNA synthetase | AAD36946 | 4 |
| aspartic protease | AAD29758 | 6 |
| Peroxisomal membrane protein (PPM2) § | AAD29759 | 5 |
| 5'-adenylylsulfate reductase § | AAD29775 | 14 |
| symbiosis-related protein | AAD29776 | 3 |
| ATP synthase gamma chain 1 (APC1) § | AAD48955 | 3 |
| protein kinase and EF hand | AAD03453 | 3 |
| ABC transporter | AAD03441 | 1 |
| Transcriptional regulator | AAD03444 | 14 |
| Unknown | AAD03446 | 12 |
| human PCF11p homolog | AAD03447 | 6 |
| NSF protein | AAD17345 | 2 |
| 1,3-beta-glucan synthase | AAD48971 | 2 |
| pyridine nucleotide-disulphide oxidoreductase | AAD48975 | 4 |
| Polyubiquitin (UBQ11) § | AAD48980 | 72 |
| wound induced protein | AAD48981 | 6 |
| short chain dehydrogenase/reductase | AAD48959 | 7 |

TABLE 9-continued

Predicted genes within CEN2 and CEN4 that correspond to the cDNA database.

| Putative function | GenBank protein accession | # of EST matches* |
|---|---|---|
| SL15† | AAD48939 | 2 |
| WD40-repeat protein | AAD48948 | 2 |

*Independent cDNAs with >95% identity,
†related gene present in non-centromeric DNA,
‡potentially associated with a mobile DNA element,
§ characterized gene (B. Tugal, 1999; J. F. Gutierrez-Marcos, 1996; N. Inohara, 1991; J. Callis, 1995).

TABLE 10

List of additional genes encoded within the boundaries of CEN4.

| Putative Function | GenBank accession | Nucleotide Position |
|---|---|---|
| 3'(2'),5'-Bisphosphate Nucleotidase | AC012392 | 71298–73681 |
| Transcriptional regulator | AC012392 | 80611–81844 |
| Equilibrative nucleoside transporter 1 | AC012392 | 88570–90739 |
| Equilibrative nucleoside transporter 1 | AC012392 | 94940–96878 |
| Equilibrative nucleoside transporter 1 | AC012392 | 98929–101019 |
| Equilibrative nucleoside transporter 1 | AC012392 | 113069–115262 |
| unknown | AC012392 | 122486–124729 |
| 4-coumarate--CoA ligase | AC012392 | 126505–128601 |
| ethylene responsive protein | AC012392 | 130044–131421 |
| Oxygen-evolving enhancer protein precursor | AC012392 | 134147–135224 |
| Kinesin | AC012392 | 137630–141536 |
| receptor-like protein kinase | AC012392 | 141847–144363 |
| LpxD-like protein | AC012392 | 144921–146953 |
| hypersensitivity induced protein | AC012392 | 147158–147838 |
| ubiquitin | AC012392 | 149057–149677 |
| unknown | AC012392 | 150254–151072 |
| ubiquitin-like protein | AC012392 | 153514–154470 |
| ubiquitin-like protein | AC012392 | 155734–156513 |
| ubiquitin-like protein | AC012392 | 156993–157382 |
| unknown | AC012392 | 159635–165559 |
| unknown | AC012392 | 166279–166920 |
| unknown | AC012392 | 167724–170212 |
| ubiquitin-like protein | AC012392 | 176819–178066 |
| polyubiquitin (UBQ10) § | AC012392 | 180613–182007 |
| phosphatidylinositol-3,4,5-triphosphate binding protein | AC012477 | 89384–91291 |
| Mitochondrial ATPase | AC012477 | 94302–94677 |
| RING-H2 finger protein | AC012477 | 95522–96142 |
| unknown | AC012477 | 104747–105196 |
| Mitochondrial ATPase | AC012477 | 105758–106595 |
| ferredoxin--NADP+ reductase | AC012477 | 107451–109095 |
| unknown | AC012477 | 109868–110620 |
| U3 snoRNP-associated protein | AC012477 | 111841–114133 |
| UV-damaged DNA binding factor | AC012477 | 114900–121275 |
| Glucan endo-1,3-Beta-Glucosidase precursor | AC012477 | 122194–122895 |
| D123-like protein | AC012477 | 125886–126887 |
| Adrenodoxin Precursor | AC012477 | 127660–129246 |
| N7 like-protein | AC012477 | 129718–131012 |
| N7 like-protein | AC012477 | 131868–133963 |
| N7 like-protein | AC012477 | 134215–136569 |
| N7 like-protein | AC012477 | 139656–140864 |

§ characterized gene (J. Callis, 1995).

B. Conservation of Centromeric DNA

To investigate the conservation of CEN2 and CEN4 sequences, PCR primer pairs were designed that correspond to unique regions in the Columbia sequence and used to survey the centromeric regions of Landsberg and Columbia at ~20 kb intervals (FIGS. 13A, B). The primers used for the analysis are listed in FIGS. 14A, B. Amplification products of the appropriate length were obtained in both ecotypes for most primer pairs (85%), indicating that the amplified regions were highly similar. In the remaining cases, primer pairs amplified Columbia, but not Landsberg DNA, even at very low stringencies. In these regions, additional primers were designed to determine the extent of nonhomology. In addition to a large insertion of mitochondrial DNA in CEN2, two other non-conserved regions were identified (FIGS. 13A, B). Because this DNA is absent from Landsberg centromeres, it is unlikely to be required for centromere function; consequently, the relevant portion of the centromeric sequence is reduced to 577 kb (CEN2) and 1250 kb (CEN4). The high degree of sequence conservation between Landsberg and Columbia centromeres indicated that the inhibition of recombination frequencies was not due to large regions of nonhomology, but instead was a property of the centromeres themselves.

C. Sequence Similarity Between CEN2 and CEN4

In order to discern centromere function, a search was conducted for novel sequence motifs shared between CEN2 and CEN4, excluding from the comparison retroelements, transposons, characterized centromeric repeats, and coding sequences resembling mobile genes. After masking simple repetitive sequences, including homopolymer tracts and microsatellites, contigs of unique sequence measuring 417 kb and 851 kb for CEN2 and CEN4, respectively, were compared with BLAST (National Center for Biotechnology Information Web Site).

The comparison showed that the complex DNA within the centromere regions was not homologous over the entire sequence length. However, 16 DNA segments in CEN2 matched 11 regions in CEN4 with >60% identity (FIG. 15). The sequences were grouped into families of related sequences, and were designated AtCCS1-7 (*Arabidopsis thaliana* centromere conserved sequences 1–7). These sequences were not previously known to be repeated in the *Arabidopsis* genome. The sequences comprised a total of 17 kb (4%) of CEN2 DNA, had an average length of 1017 bp, and had an A+T content of 65%. Based on similarity, the matching sequences were sorted into groups, including two families containing 8 sequences each, 3 sequences from a small family encoding a putative open reading frame, and 4 sequences found once within the centromeres, one of which corresponds to predicted CEN2 and CEN4 proteins with similarity throughout their exons and introns (FIG. 15).

Searches of the *Arabidopsis* genomic sequence database demonstrated that AtCCS1–AtCCS5 were moderately repeated sequences that appear in centromeric and pericentromeric regions. The remaining sequences were present only in the genetically-defined centromeres. Similar comparisons of all 16 *S. cerevisiae* centromeres defined a consensus consisting of a conserved 8 bp CDEI motif, an AT-rich 85 bp CDEII element, and a 26 bp CDEII region with 7 highly conserved nucleotides (Fleig et al. 1995). In contrast, surveys of the three *S. pombe* centromeres revealed conservation of overall centromere structure, but no universally conserved motifs (Clark, 1998).

Example 9

Construction of Plant Minichromosomes

Minichromosomes are constructed by combining the previously isolated essential chromosomal elements. Exemplary minichromosome vectors include those designed to be "shuttle vectors"; i.e., they can be maintained in a convenient host (such as *E. coli*, *Agrobacterium* or yeast) as well as plant cells.

A. General Techniques for Minichromosome Construction

A minichromosome can be maintained in *E. coli* or other bacterial cells as a circular molecule by placing a removable stuffer fragment between the telomeric sequence blocks. The stuffer fragment is a dispensable DNA sequence, bordered by unique restriction sites, which can be removed by restriction digestion of the circular DNAs to create linear molecules with telomeric ends. The linear minichromosome can then be isolated by, for example, gel electrophoresis. In addition to the stuffer fragment and the plant telomeres, the minichromosome contains a replication origin and selectable marker that can function in plants to allow the circular molecules to be maintained in bacterial cells. The minichromosomes also include a plant selectable marker, a plant centromere, and a plant ARS to allow replication and maintenance of the DNA molecules in plant cells. Finally, the minichromosome includes several unique restriction sites where additional DNA sequence inserts can be cloned. The most expeditious method of physically constructing such a minichromosome, i.e., ligating the various essential elements together for example, will be apparent to those of ordinary skill in this art.

A number of minichromosome vectors have been designed by the current inventors and are disclosed herein for the purpose of illustration (FIGS. 7A–7H). These vectors are not limiting however, as it will be apparent to those of skill in the art that many changes and alterations may be made and still obtain a functional vector.

B. Modified Technique for Minichromosome Construction

Figure 10A:
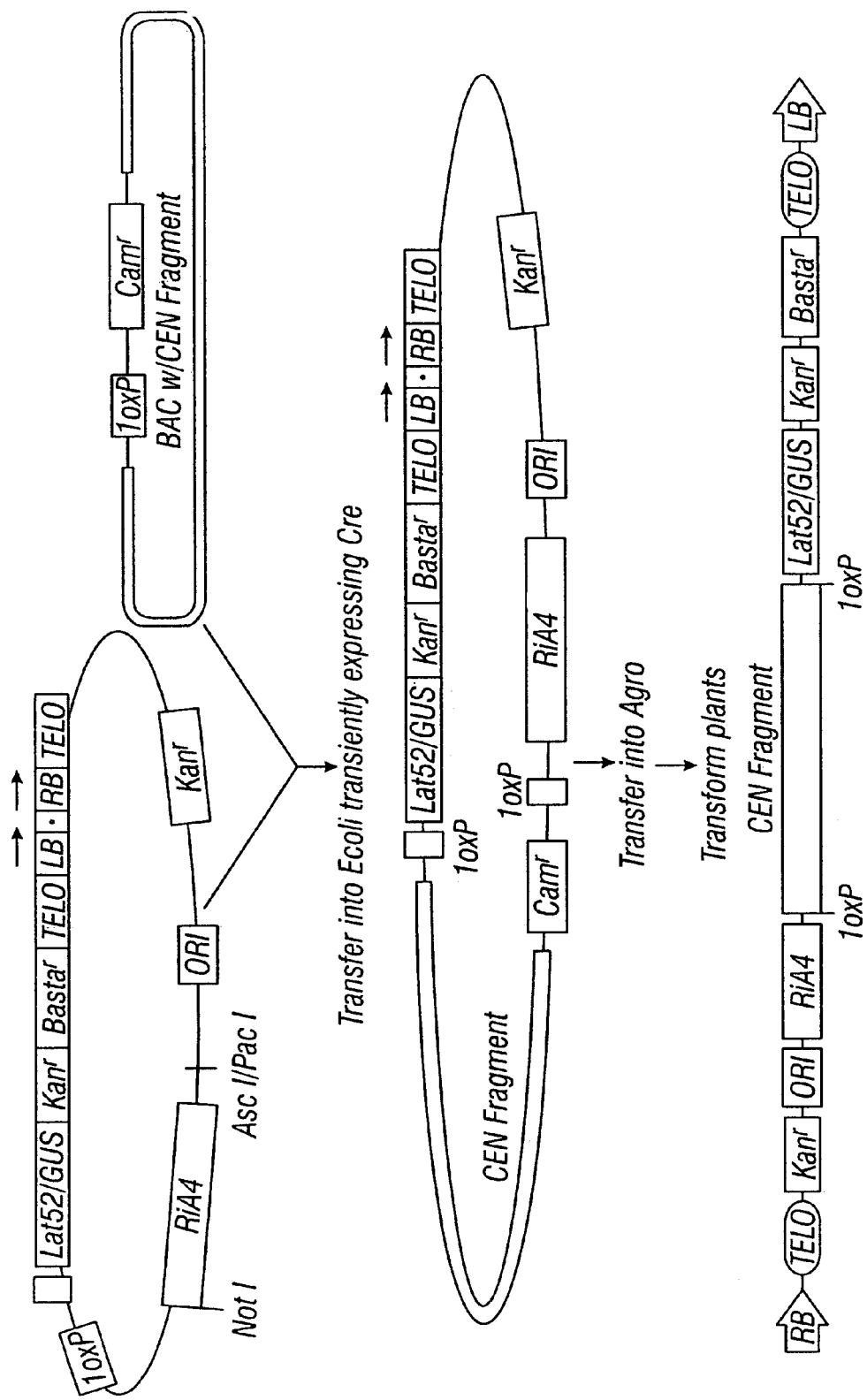
Figure 10B:
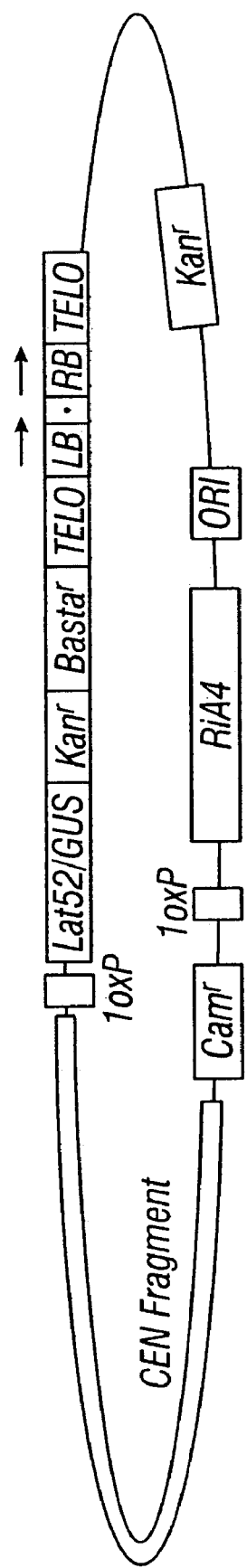
Figure 10C:
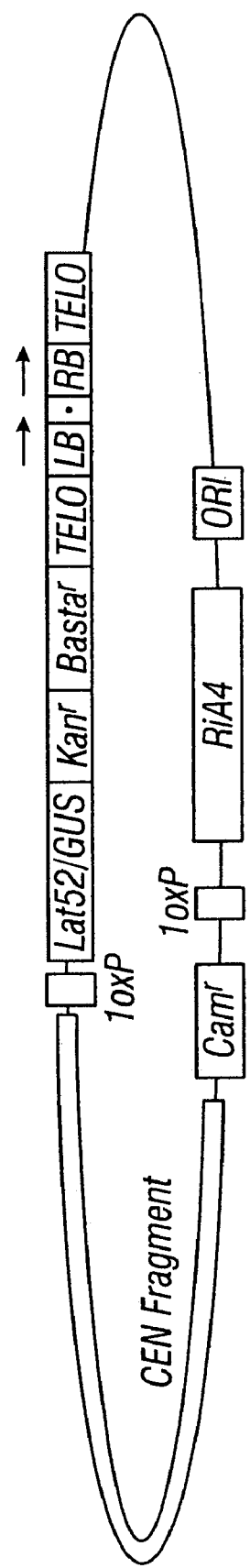
Figure 10D:
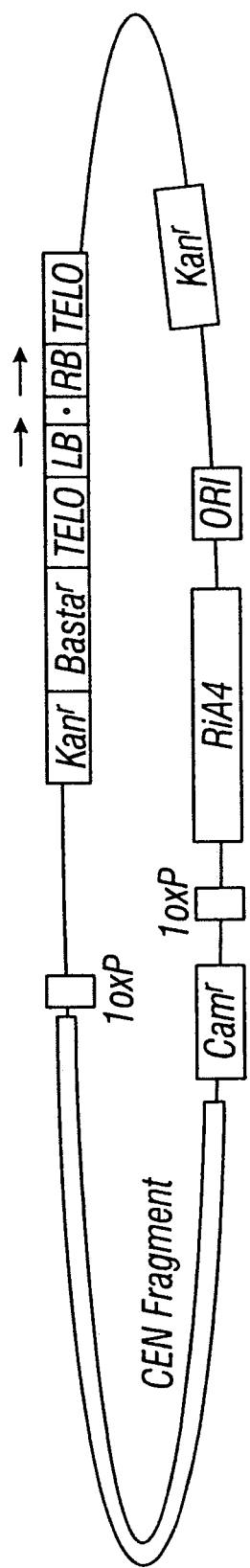
Figure 10E:
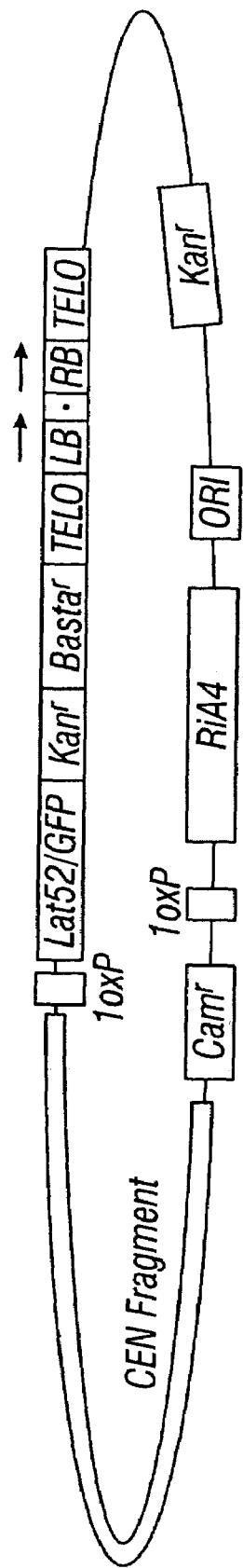

A two step method was developed for construction of minichromosomes, which allows adding essential elements to BAC clones containing centromeric DNA. These procedures can take place in vivo, eliminating problems of chromosome breakage that often happen in the test tube. The details and advantages of the techniques are as follows:

1.) One plasmid can be created that contains markers, origins and border sequences for *Agrobacterium* transfer, markers for selection and screening in plants, plant telomeres, and a loxP site or other site useful for site-specific recombination in vivo or in vitro. The second plasmid can be an existing BAC clone, isolated from the available genomic libraries (FIG. 10A).
2.) The two plasmids are mixed, either within a single *E. coli* cell, or in a test tube, and the site-specific recombinase cre is introduced. This will cause the two plasmids to fuse at the loxP sites (FIG. 10B).
3.) If deemed necessary, useful restriction sites (AseI/PacI or Not I) are included to remove excess material. (for example other selectable markers or replication origins)
4.) Variations include vectors with or without a Kan$^R$ gene (FIGS. 10B, 10C), with or without a LAT52 GUS gene, with a LAT52 GFP gene, and with a GUS gene under the control of other plant promoters. (FIGS. 10C, 10D and 10E).

C. Method for Preparation of Stable Non-Integrated Minichromosomes

Figure 10F:
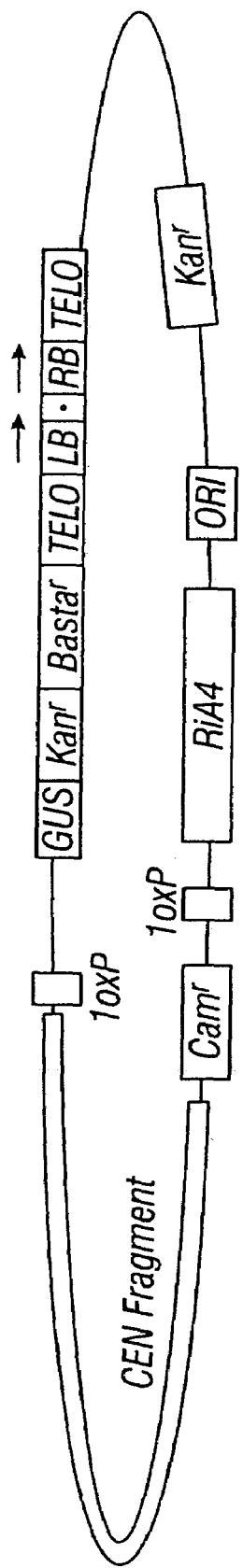
Figure 10G:
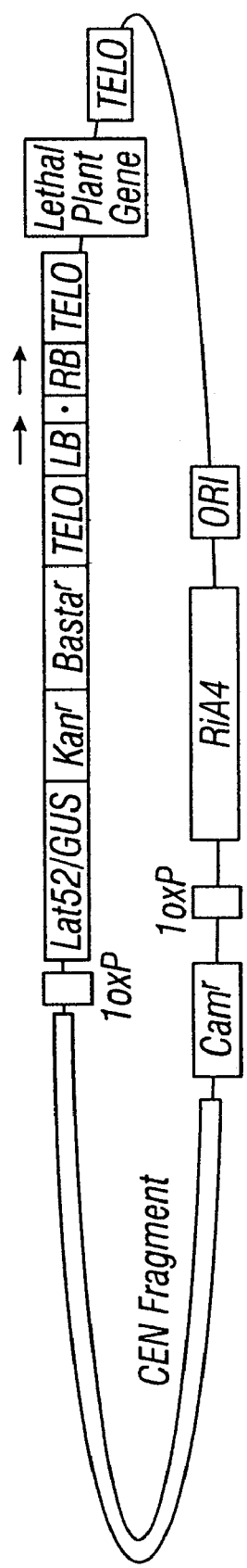

A technique has been developed to ensure that minichromosomes do not integrate into the host genome (FIG. 10F). In particular, minichromosomes must be maintained as distinct elements separate from the host chromosomes. In one method for ensuring that the introduced minichromosome does not integrate, the inventors envision a variety that would encode a lethal plant gene (such as diptheria toxin or any other gene product that, when expressed, causes lethality in plants). This gene could be located between the right *Agrobacterium* border and the telomere. Minichromosomes that enter a plant nucleus and integrate into a host chromosome would result in lethality. However, if the minichromosome remains separate, and further, if the ends of this construct are degraded up to the telomeres, then the lethal gene would be removed and the cells would survive.

Example 10

Facilitation of Genetic Introgression

It is also contemplated by the inventors that one could employ techniques or treatments which stimulate recombination to facilitate introgression. Introgression describes a breeding technique whereby one or more desired traits is transferred into one strain (A) from another (B), the trait is then isolated in the genetic background of the desired strain (A) by a series of backcrosses to the same strain (A). The number of backcrosses required to isolate the desired trait in the desired genetic background is dependent on the frequency of recombination in each backcross.

Backcrossing transfers a specific desirable trait from one source to an inbred or other plant that lacks that trait. This can be accomplished, for example, by first crossing a superior inbred (A) (recurrent parent) to a donor inbred (non-recurrent parent), which carries the appropriate gene(s) for the trait in question, for example, a construct prepared in accordance with the current invention. The progeny of this cross first are selected in the resultant progeny for the desired trait to be transferred from the non-recurrent parent, then the selected progeny are mated back to the superior recurrent parent (A). After five or more backcross generations with selection for the desired trait, the progeny are hemizygous for loci controlling the characteristic being transferred, but are like the superior parent for most or almost all other genes. The last backcross generation would be selfed to give progeny which are pure breeding for the gene(s) being transferred, i.e. one or more transformation events.

Therefore, through a series a breeding manipulations, a selected transgene may be moved from one line into an entirely different line without the need for further recombinant manipulation. Transgenes are valuable in that they typically behave genetically as any other gene and can be manipulated by breeding techniques in a manner identical to any other corn gene. Therefore, one may produce inbred plants which are true breeding for one or more transgenes. By crossing different inbred plants, one may produce a large number of different hybrids with different combinations of transgenes. In this way, plants may be produced which have the desirable agronomic,properties frequently associated with hybrids ("hybrid vigor"), as well as the desirable characteristics imparted by one or more transgene(s).

Breeding also can be used to transfer an entire minichromosome from one plant to another plant. For example, by crossing a first plant having a minichromosome to a second plant lacking the minichromosome, progeny of any generation of this cross may be obtained having the minichromosome, or any additional number of desired minichromosomes. Through a series of backcrosses, a plant may be obtained that has the genetic background of the second plant but has the minichromosome from the first plant.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

REFERENCES

The following references, to the extent that they provide exemplary procedural or other details supplementary to those set forth herein, are specifically incorporated herein by reference.

Abdullah et al., *Biotechnology*, 4:1087, 1986.
Abel et al., *Science*, 232:738–743, 1986.
Alfenito et al., "Molecular characterization of a maize B chromosome centric sequence," *Genetics*, 135:589–597, 1993.
Alfenito and Birchler, "Molecular characterization of a maize B chromosome centric sequence," Genetics 135: 589–597, 1993.
Ananiev et al., "A knob-associated tandem repeat in maize capable of forming fold-back DNA segments: are chromosome knobs megatransposons?" Proc. Natl. Acad. Sci. U.S.A. 95 (18), 10785–10790, 1998.
Ananiev et al., "Chromosome-specific molecular organization of maize (*Zea mays* L.) centromeric regions," Proc. Natl. Acad. Sci. U.S.A. 95 (22), 13073–13078, 1998.
Ananiev et al., "Complex structure of knob DNA on maize chromosome 9. Retrotransposon invasion into heterochromatin," Genetics 149 (4), 2025–2037, 1998
Araki et al., "Site-specific recombinase, R, encoded by yeast plasmid pSR1," *J. Mol. Biol.* 225:25–37, 1992.
Armstrong et al., "Physical mapping of DNA repetitive sequences to mitotic and meiotic chromosomes of *Brassica oleracea* var. *alboglabra* by fluorescence in situ hybridization," Heredity 81: 666–673, 1998.
Barkai-Golan et al., *Arch. Microbiol.*, 116:119–124, 1978.
Baum et al., "The centromeric K-type repeat and the central core are together sufficient to establish a functional *Schizosaccharomyces pombe* centromere," *Mol. Bio. Cell.*, 5:747–761, 1994.
Bell et al., "Assignment of 30 microsatellite loci to the linkage map of *Arabidopsis*," *Genomics*, 19:137–144, 1994.
Bemal-Lugo and Leopold, *Plant Physiol.*, 98:1207–1210, 1992.
Berzal-Herranz et al., *Genes and Devel.*, 6:129–134, 1992.
Bevan et al., *Nucleic Acids Research*, 11 (2):369–385, 1983.
Bevan et al., *BioEssays* 21:110, 1999.
Blackman et al., *Plant Physiol.*, 100:225–230, 1992.
Bloom, "The centromere frontier: Kinetochore components, microtubule-based motility, and the CEN-value paradox," *Cell*, 73:621–624, 1993.
Bol et al., Annu. Rev. Phytopath., 28:113–138, 1990.
Bowler et al., *Ann Rev. Plant Physiol.*, 43:83–116, 1992.
Brandes et al., *Chrom. Res.*, 5:238, 1997.
Branson and Guss, *Proceedings North Central Branch Entomological Society of America*, 27:91–95, 1972.
Brisson et al., *Nature*, 310:511, 1984.
Broach et al., *Gene*, 8:121–133, 1979.
Broakaert et al., *Science*, 245:1100–1102, 1989.
Burke et al., *Science*, 236:806–812, 1987.
Bytebier et al., *Proc. Natl. Acad. Sci. USA*, 84:5345, 1987.
Callis et al., *Genes and Development*, 1:1183, 1987.
Cambareri et al., *Mol. Cell. Biol.*, 18:5465, 1998.
Campbell (ed.), In: Avermectin and Abamectin, 1989.
Campbell, "Monoclonal Antibody Technology, Laboratory Techniques in Biochemistry and Molecular Biology," Vol. 13, Burden and Von Knippenberg, Eds. pp. 75–83, Elsevier, Amsterdam, 1984.

Capecchi, "High efficiency transformation by direct microinjection of DNA into cultured mammalian cells," *Cell* 22 (2):479–488, 1980.

Carbon et al., In: *Recombinant Molecules: Impact on Science and Society* (Raven Press), 335–378, 1977.

Carbon et al., "Centromere structure and function in budding and fission yeasts," *New Biologist*, 2:10–19, 1990.

Carpenter et al., "The control of the distribution of meiotic exchange in *Drosophilla melanogaster*," *Genetics*, 101: 81–90, 1982.

Cech et al., "In vitro splicing of the ribosomal RNA precursor of Tetrahymena: involvement of a guanosine nucleotide in the excision of the intervening sequence," *Cell*, 27:487–496, 1981.

Chandler et al., *The Plant Cell*, 1:1175–1183, 1989.

Chang et al., "Restriction fragment length polymorphism linkage map for *Arabidopsis thaliana*," *Proc. Natl. Acad. Sci., USA*, 85:6856–6860, 1988.

Charlesworth et al., *Nature*, 371:215, 1994.

Charlesworth, C. H. Langley, W. Stephan, 112:947, 1986

Chepko, *Cell*, 37:1053,1984.

Choi et al., *Plant Mol Biol Rep*, 13:124–29, 1995.

Choo, K. H. A. *Genome Res.* 8:81, 1998.

Chowrira et al., "In vitro and in vivo comparison of hammerhead, hairpin, and hepatitis delta virus self-processing ribozyme cassetyes," *J. Biol. Chem.*, 269:25856–25864, 1994.

Chu et al., "Separation of large DNA molecules by contour-clamped homogeneous electric fields" *Science*, 234, 1582–1585, 1986.

Chye et al., *Plant Mol. Biol.*, 35:893, 1997.

Clapp, "Somatic gene therapy into hematopoietic cells. Current status and future implications," *Clin. Perinatol.* 20(1):155–168, 1993.

Clark, L. *Curr. Op. Gen. & Dev.*, 8:212, 1998

Clarke et al., "Isolation of a yeast centromere and construction of functional small circular chromosomes," *Nature*, 287:504–509, 1980.

Cohen et al., *Proc. Nat'l Acad. Sci. USA*, 70:3240, 1973.

Conkling et al., *Plant Physiol.*, 93:1203–1211, 1990.

Copenhaver and Pikaard, "RFLP and physical mapping with an rDNA-specific endonuclease reveals that nucleolus organizer regions of *Arabidopsis thaliana* adjoin the telomeres on chromosomes 2 and 4," *Plant J.*, 9:259–276, 1996.

Copenhaver et al., "Use of RFLPs larger than 100 kbp to map position and internal organization of the nucleolus organizer region on chromosome 2 in *Arabidopsis thaliana*," *Plant J.* 7, 273–286, 1995.

Copenhaver et al., *Proc. Natl. Acad. Sci.* 95:247, 1998.

Copenhaver et al., *Science.* 286:2468–2474, 1999.

Copenhaver and Preuss, *Plant Biology*, 2:104–108, 1999.

Coxson et al., *Biotropica*, 24:121–133, 1992.

Creusot et al., *Plant Journal.*, 8:763–70, 1995

Cristou et al., *Plant Physiol*, 87:671–674, 1988.

Cuozzo et al., *Bio/Technology*, 6:549–553, 1988.

Curiel et al., "Adenovirus enhancement of transferrin-polylysine-mediated gene delivery," *Proc. Nat l Acad. Sci. USA* 88(19):8850–8854, 1991.

Curiel et al., high-efficiency gene transfer mediated by adenovirus coupled to DNA-polylysine complexes," *Hum. Gen. Ther.* 3(2):147–154, 1992.

Cutler et al., *J. Plant Physiol.*, 135:351–354, 1989.

Czapla and Lang, *J. Econ. Entomol.*, 83:2480–2485, 1990.

Davies et al., *Plant Physiol.*, 93:588–595, 1990.

Dellaporta et al., In: *Chromosome Structure and Function: Impact of New Concepts, 18th Stadler Genetics Symposium*, 11:263–282, 1988.

Dennis and Peacock, "Knob heterochromatin homology in maize and its relatives," J. Mol. Evol. 20, 341–350, 1984.

Depicker et al., *Plant Cell Reports*, 7:63–66, 1988.

DiLaurenzio et al., *Cell*, 86:423–33, 1996

Dillon et al., *Recombinant DNA Methodology*, 1985.

Donahue et al., "The nucleotide sequence of the HIS4 region of yeast," *Gene April;* 18(1):47–59, 1982.

Dure et al., *Plant Molecular Biology*, 12:475–486, 1989.

Earnshaw et al., "Proteins of the inner and outer centromere of mitotic chromosomes," *Genome*, 31:541–552, 1989.

Earnshaw, "When is a centromere not a kinetochore?," *J. Cell Sci.*, 99:1–4, 1991.

Ebert et al., 84:5745–5749, *Proc. Nat'l Acad. Sci. USA*, 1987

Ecker, J R, *Genomics*, 19:137–144

Ecker, *Methods*, 1:186–94, 1990.

Eglitis et al., "Retroviral vectors for introduction of genes into mammalian cells," *Biotechniques* 6(7):608–614, 1988.

Eglitis et al., "Retroviral-mediated gene transfer into hemopoietic cells," *Avd. Exp. Med. Biol.* 241:19–27, 1988.

Enomoto et al., "Mapping of the pin locus coding for a site-specific recombinase that causes flagellar-phase variation in *Escherichia coli* K-12," *J. Bacteriol.*, 156: 663–668, 1983.

Erdmann et al., *J. Gen. Microbiology*, 138:363–368, 1992.

Ferrin et al., "Selective cleavage of human DNA: RecA-Assited Restriction Endonuclease (RARE) cleavage," *Science*, 254:1494–1497, 1991.

Fitzpatrick, *Gen. Engineering News*, 22:7, 1993.

Fleig, U. et al., "Functional selection for the centromere DNA from yeast chromosome VIII," *Nuc. Acids. Res.* 23:922–924, 1995.

Forster and Symons, "Self-cleavage of plus and minus RNAs of a virusoid and a structural model for the active sites," *Cell*, 49:211–220, 1987.

Fraley et al., *Biotechnology*, 3:629, 1985.

Franz et al., *Plant J.*, 13:867, 1998.

Fromm et al., *Nature*, 312:791–793, 1986.

Fromm et al., "Expression of genes transferred into monocot and dicot plant cells by electroporation," *Proc. Natl. Acad. Sci. USA* 82(17):5824–5828, 1985.

Fujimura et al., *Plant Tissue Culture Letters*, 2:74, 1985.

Fynan et al., "DNA vaccines: protective immunizations by parenteral, mucosal, and gene gun inoculations," *Proc. Nat'l Acad. Sci. USA* 90(24):11478–11482, 1993.

Gatehouse et al., *J. Sci. Food. Agric.*, 35:373–380, 1984.

Gefter et al., *Somatic Cell Genet.* 3:231–236, 1977.

Gerlach et al., "Construction of a plant disease resistance gene from the satellite RNA of tobacco rinspot virus," *Nature (London)*, 328:802–805, 1987.

Goding, "Monoclonal Antibodies: Principles and Practice," pp. 60–74. 2nd Edition, Academic Press, Orlando, Fla., 1986.

Golic and Lindquist, "The FLP recombinase of yeast catalyses site-specific recombination in the *Drosophila* genome," *Cell*, 59:499–509, 1989.

Goring et al., *Proc. Natl. Acad. Sci. USA*, 88:1770–1774, 1991.

Graham et al., "Transformation of rat cells by DNA of human adenovirus 5," Virology 54(2):536–539, 1973.

Grellet et al., "Organization and evolution of a higher plant alphoid-like satellite DNA sequence," J. Mol. Biol. 187: 495–507, 1986.

Grill and Somerville, *Mol Gen Genet*, 226:484–90, 1991

Guerrero et al., *Plant Molecular Biology*, 15:11–26, 1990.

Gupta et al., *Proc. Natl. Acad. Sci. USA*, 90:1629–1633, 1993.

Gutierrez-Marcos et al., *Proc. Natl. Acad. Sci., USA*, 93:13377, 1996.

Haaf et al., "Integration of human α-satellite DNA into simian chromosomes: centromere protein binding and disruption of normal chromosome segregation," *Cell*, 70:681–696, 1992.

Hadlaczky et al., "Centromere formation in mouse cells cotransformed with human DNA and a dominant marker gene," *Proc. Natl. Acad. Sci. USA*, 88:8106–8110, 1991.

Hamilton et al., "Stable transfer of intact high molecular weight DNA into plant chromosomes," *Proc Natl Acad Sci USA* 93(18):9975–9, 1996

Hamilton, "A binary-BAC system for plant transformation with high-molecular-weight DNA," *Gene*, 4; 200(1–2): 107–16, 1997.

Hammock et al., *Nature*, 344:458–461, 1990.

Harrison and Heslop-Harrison, "Centromeric repetitive DNA sequences in the genus *Brassica*," Theor. Appl. Genet. 90:157–165, 1995.

Haseloff et al., *Proc. Nat'l Acad. Sci. USA* 94(6):2122–2127, 1997.

Hauge et al., *Symp Soc Exp Biol*, 45:45–56, 1991

Hegemann et al., "The centromere of budding yeast," *Bioassays*, 15(7):451–460, 1993.

Hemenway et al., *The EMBO J*, 7:1273–1280, 1988.

Heslop-Harrison et al., *Plant Cell*, 11:31, 1999.

Hilder et al., *Nature*, 330:160–163, 1987.

Hinchee et al., *Bio/technol.*, 6:915–922, 1988.

Hoess et al., *Proc Natl Acad Sci*, 79:3398–402, 1982

Hsiao et al., *J. Proc. Nat'l Acad. Sci. USA*, 76:3829–3833, 1979.

Hudspeth and Grula, *Plant Mol. Biol.*, 12:579–589, 1989.

Hwang et al., "Identification and map position of YAC clones comprising one-third of the *Arabidopsis* genome, *The Plant Journal.*, 1:367–374, 1991.

Ikeda et al., *J. Bacteriol.*, 169:5615–5621, 1987.

Ikuta et al., *Bio/technol.*, 8:241–242, 1990.

Inohara et al., *J. Biol. Chem.*, 266, 7333, 1991.

Johnston et al., "Gene gun transfection of animal cells and genetic immunization," *Methods Cell. Biol.* 43(A): 353–365, 1994.

Jones, *Embo J.*, 4:2411–2418, 1985.

Jones, *Mol Gen. Genet.*, 207:478, 1987.

Jorgensen et al., *Mol. Gen. Genet.*, 207:471, 1987.

Jouanin et al., *Mol Gene Genet*, 201:370–4, 1985

Joyce, "RNA evolution and the origins of life," *Nature*, 338:217–244, 1989.

Kaasen et al., *J. Bacteriology*, 174:889–898, 1992.

Karpen, *Curr. Op. Gen. & Dev.*, 4:281, 1994.

Karsten et al., *Botanica Marina*, 35:11–19, 1992.

Katz et al., *J. Gen. Microbiol.*, 129:2703–2714, 1983.

Kim and Cech, "Three dimensional model of the active site of the self-splicing rRNA precursor of Tetrahymena," *Proc. Natl. Acad. Sci. USA*, 84:8788–8792, 1987.

Klee et al., *Bio/Technology* 3:637–642, 1985.

Klein et al., *Nature*, 327:70–73, 1987.

Klein et al., *Proc. Nat'l Acad. Sci. USA*, 85:8502–8505, 1988.

Kohler et al., *Eur. J. Immunol.* 6:511–519, 1976.

Kohler et al., *Nature* 256:495–497, 1975.

Kolchinski and Gresshoff, "A major satellite DNA of soybean is a 92-base pairs tandem repeat," Theor. Appl. Genet. 90(5): 621–626, 1995.

Konieczny et al., "A procedure for mapping *Arabidopsis* mutations using codominant ecotype-specific PCR-based markers," *The Plant Journal.*, 4:403–410, 1993.

Konieczny et al., *Genetics*, 127:801, 1991.

Koorneef et al., *Genetica*, 61:4146, 1983.

Koorneef, "Linkage map of *Arabidopsis thaliana* (2n=10)," In S J O'Brien, ed, *Genetic Maps* 1987: *A compilation of linkage and restriction maps of genetically studied organisms*, 724–745, 1987.

Koorneef, "The use of telotrisomics for centromere mapping in *Arabidopsis thaliana* (L.). Heynh, *Genetica*, 62:33–40, 1983.

Koster and Leopold, *Plant Physiol.*, 88:829–832, 1988.

Kuby, J., *Immunology 2nd Edition*, W.H. Freeman & Company, NY, 1994

Kuhn et al., *Proc. Natl. Acad. Sci.*, 88:1306, 1991.

Kyte et al., A simple method for displaying the hydropathic character of a protein," *J. Mol. Biol.* 157(1):105–132, 1982.

Lawton et al., *Plant Mol. Biol.* 9:315–324, 1987.

Lakshmikumaran and Ranade, "Isolation and characterization of a highly repetitive DNA of *Brassica campestris*," Plant Mol. Biol. 14:447–448, 1990.

Lechner et al., "A 240 kd multisubunit protein complex, CBF3 is a major component of the budding yeast centromere," *Cell*, 64:717–725, 1991.

Lee and Saier, *J. of Bacteriol.*, 153–685, 1983.

Levings, *Science*, 250:942–947, 1990.

Lewin, *Genes II*, John Wiley & Sons, Publishers, N.Y., 1985.

Li et al., *Plant Cell*, 7:1599, 1995.

Li et al., *Proc. Natl. Acad. Sci.*, 87:4580–4584, 1990.

Lieber and Strauss, "Selection of efficient cleavage sites in target RNAs by using a ribozyme expression library." *Mol. Cell. Biol.*, 15: 540–551, 1995.

Lin, S., Kaul, S. Rounsley, T. P. Shea, M-I. Benito, C. D. Town, C. Y. Fujii, T. Mason, C. L. Bowman, M. Barnstead, T. Feldblyum, C. R. Buell, K. A. Ketchum, C. M. Ronning, H. Koo, K. Moffat, L. Cronin, M. Shen, G. Pai, S. Van Aken, L., Umayam, L. Tallon, J. Gill, M. D. Adams, A. J. Carrera, T. H. Creasy, H. M. Goodman, C. R. Somerville, G. P. Copenhaver, D. Preuss, W. C. Nierman, O. White, J. A. Eisen, S. Salzberg, C. M. Fraser, and J. C. Venter, "Sequence and Analysis of Chromosome 2 of *Arabidopsis thaliana*," *Nature* 402: 761–768, 1999.

Liu, Y G., Shirano, Y., Fukaki, H., Yanai, Y., Tasaka, M., Tabata, S., Shibata, D, *Proc. Natl Acad Sci USA* 96: 6535–40, 1999.

Lohe and Hilliker, *Curr. Op. Gen. & Dev.*, 5:746, 1995.

Loomis et al., *J. Expt. Zoology*, 252:9–15, 1989.

Lorz et al., *Mol. Gen. Genet.*, 199:178, 1985.

Louis, E J, "Corrected sequence for the right telomere of *Saccharomyces cerevisiae* chromosome III," *Yeast*, 10(2): 271–4, 1994.

Lu et al., "High efficiency retroviral mediated gene transduction into single isolated immature and replatable CD34(3+) hematopoietic stem/progenitor cells from human umbilical cord blood," *J. Exp. Med.* 178(6):2089–2096, 1993.

Maeser and Kahmann, "The GIN recombinase of phage Mu can catalyse site-specific recombination in plant protoplasts," *Mol. Gen. Genet.*, 230:170–176, 1991.

Mahtani, M. M. and Willard, H. F. *Genome Res.* 8:100, 1998.

Maloy, S. R., "Experimental Techniques in Bacterial Genetics" Jones and Bartlett Prokop, A., and Bajpai, R. K. "Recombinant DNA Technology I" *Ann. N.Y. Acad. Sci.* vol. 646, 1991.

Maluszynaska et al., "Molecular cytogenetics of the genus *Arabidopsis*: In situ localization of rDNA sites, chromosome numbers and diversity in centromeric heterochromatin," *Annals Botany,* 71:479–484, 1993.

Maluszynska et al., "Localization of tandemly repeated DNA sequences in *Arabidopsis thaliana,*" *Plant Jour.,* 1(2):159–166, 1991.

Maniatis et al., "Molecular Cloning: a Laboratory Manual," Cold Spring Harbor Laboratory, Cold Spring Harbor, N.Y., 1982.

Marcotte et al., *Nature,* 335:454, 1988.

Mariani et al., *Nature,* 347:737–741, 1990.

Marra et al., *Nature Genet.* 22:265, 1999.

Martinez-Zapater et al., *Mol. Gen. Genet.,* 204:417–423, 1986.

Matsuura et al., *Journal of Bacteriology,* 178:3374–6, 1996

McCabe et al., *Biotechnology,* 6:923, 1988.

Michel and Westhof, "Modeling of the three-dimensional architecture of group I catalytic introns based on comparative sequence analysis," *J. Mol. Biol.,* 216:585–610, 1990.

Mortimer et al., "Genetic mapping in *Saccharomyces cerevisiae,*" Life Cycle and Inheritance, In: *The Molecular Biology of the Yeast Saccharomyces,* 11–26, 1981.

Mozo et al., *Mol Gen Genet,* 258:562–70, 1998.

Mozo et al., *Nature Genet.* 22:271, 1999.

Mundy and Chua, *The EMBO J.,* 7:2279–2286, 1988.

Murakami et al., *Mol. Gen. Genet.,* 205:42–50, 1986.

Murata et al., *Plant J.,* 12:31, 1997.

Murdock et al., *Phytochemistry,* 29:85–89, 1990.

Murray et al., *Nature,* 305:189–193, 1983.

Mysore et al., "An *arabidopsis* histone H2A mutant is deficient in *agrobacterium* T-DNA integration," *Proc Natl Acad Sci USA* 18; 97(2):948–53, 2000a.

Mysore et al., "*Arabidopsis* ecotypes and mutants that are recalcitrant to *Agrobacterium* root transformation are susceptible to germ-line transformation. *Plant J.* 21(1): 9–16, 2000b.

Napoli, Lemieux, Jorgensen, "Introduction of a chimeric chalcone synthase gene into petunia results in reversible co-suppression of homologous genes in trans," *Plant Cell,* 2:279–289, 1990.

Negrutiu, I., Hinnisdaels, S., Cammaerts, D., Cherdshewasart, W., Gharti-Chhetri, G., and Jacobs, M. "Plant protoplasts as genetic tool: selectable markers for developmental studies," *Int. J. Dev. Biol.* 36: 73–84, 1992.

Nester, *Ann. Rev. Plant Phys.,* 35:387–413, 1984.

Nicklas, "The forces that move chromosomes in mitosis," *Annu. Rev. Biophys. Biophys. Chem.,* 17:431–39, 1988.

Nussbaum et al., *Proc. Nat'l Acad. Sci USA,* 73:1068, 1976.

Odell et al., *Nature,* 313:810–812, 1985.

Ohmori and Tomizawa, "Nucleotide sequence of the region required for maintenance of colicin E1 plasmid," *Mol Gen Genet, October* 3; 176(2):161–70, 1979.

Omirulleh et al., *Plant Molecular Biology,* 21:415–428, 1993.

Ow et al., *Science,* 234:856–859, 1986.

Page et al., "Characterization of a maize chromosome 4 centromeric sequence: evidence for an evolutionary relationship with the B chromosome centromere," Genetics 159: 291–302, 2001.

Palukaitis et al., "Characterization of a viroid associated with avacado sunblotch disease," *Virology,* 99:145–151, 1979.

Peacock et al., "Highly repeated DNA sequence limited to knob heterochromatin in maize," *Proc. Natl. Acad. Sci. U.S.A.* 78, 4490–4494, 1981.

Pelissier et al., *Genetica,* 97:141, 1996.

Pelissier et al., *Plant Mol. Biol.,* 26:441, 1995.

Perkins, "The detection of linkage in tetrad analysis," *Genetics,* 38, 187–197, 1953.

Perlak et al., *Proc. Natl. Acad. Sci. USA,* 88:3324–3328, 1991.

Perriman et al., "Extended target-site specificity for a hammerhead ribozyme," *Gene,* 113:157–163, 1992.

Peterson et al., "Production of transgenic mice with yeast artificial chromosomes," Trends Genet. 13: 61–66, 1997.

Phi-Van et al., *Mol. Cell. Biol.,* 10:2302–2307. 1990.

Piatkowski et al., *Plant Physiol.,* 94:1682–1688, 1990.

Potrykus et al., *Mol. Gen. Genet.,* 199:183–188, 1985.

Prasher et al., *Biochem. Biophys. Res. Commun.,* 126(3): 1259–1268, 1985.

Preuss et al., "Tetrad analysis possible in *Arabidopsis* with mutation of the QUARTET (QRT) genes," *Science,* 264: 1458, 1994.

Price et al., "Systematic relationships of *Arabidopsis*: a molecular and morpoholical perspective", in: Somerville, C. and Meyerowitz, E. (eds.) *Arabidopsis,* Cold Sping Harbor Press, NY, 1995.

Prody et al., "Autolytic processing of dimeric plant virus satellite RNA." *Science,* 231:1577–1580, 1986.

Prokop et al., *Ann. N.Y. Acad. Sci.* 646, 1991

Puechberty, J. *Genomics* 56:247, 1999

Rathore et al., *Plant Mol Biol,* 21:871–84, 1993

Rattner, "The structure of the mammalian centromere," *Bioassays,* 13(2):51–56, 1991.

Ravatn et al., *Journal of Bacteriology,* 180:5505–14, 1998.

Reed et al., *J. Gen. Microbiology,* 130:1–4, 1984.

Reichel et al., *Proc. Nat'l Acad. Sci. USA,* 93 (12) p. 5888–5893. 1996

Reinhold-Hurek and Shub, "Self-splicing introns in tRNA genes of widely divergent bacteria," *Nature,* 357:173–176, 1992.

Rensburg et al., *J. Plant Physiol.,* 141:188–194, 1993.

Richards and Ausubel, "Isolation of a higher eukaryotic telomere from *Arabidopsis thaliana,*" *Cell,* 8:53(1):127–36, 1988.

Richards et al., "The centromere region of *Arabidopsis thaliana* chromosome 1 contains telomere-similar sequences," *Nucleic Acids Research,* 19(12):3351–3357, 1991.

Rieder, "The formation, structure and composition of the mammalian kinetochore and kinetochore fiber," *Int. Rev. Cytol,* 79:1–58, 1982.

Rogers et al., *Meth. in Enzymol.,* 153:253–277, 1987.

Rosenberg et al., "RFLP subtraction: A method for making libraries of polymorphic markers," *Proc. Natl. Acad. Sci. USA,* 91:6113–6117, 1994.

Round et al., *Genome Res,* 7, 1053, 1997.

Sauer, "Functional expression of the cre-lox site-specific recombination system in the yeast *Saccharomyces cerevisiae,*" *Mol. and Cell. Biol.,* 7: 2087–2096, 1987.

Schmidt et al., *Plant Journal.,* 5:735–44, 1994

Schwartz et al., Cold Spring Harbor *Symp. Quant. Biol.,* 47, 195–198, 1982.

Schweizer et al., "Species specific sequences for the identification of somatic hybrids between *Lycopersicon esculentum* and *Solanum acaule*," Theor. Appl. Genet. 75, 679–684, 1998

Sears et al., "Cytogenetic studies in *Arabidopsis thaliana*," Can. J. Genet. Cytol., 12:217–233, 1970.

Segal, "Biochemical Calculations" 2nd Edition. John Wiley & Sons, New York, 1976.

Setlow et al., *Genetic Engineering: Principles and Methods*, 1979.

Shagan and Bar-Zvi, *Plant Physiol.*, 101:1397–1398, 1993.

Shapiro, In: *Mobile Genetic Elements*, 1983.

Sheen et al., *Plant Journal.*, 8(5):777–784, 1995.

Shingo et al., *Mol. Cell. Biol.*, 6:1787, 1986.

Simoens et al., *Nuc. Acids Res.*, 16:6753, 1988.

Smith, Watson, Bird, Ray, Schuch, Grierson, "Expression of a truncated tomato polygalacturonase gene inhibits expression of the endogenous gene in transgenic plants," *Mol. Gen. Genet.*, 224:447–481, 1990.

Smithies et al., *Nature*, 317:230–234, 1985.

Smythe, "Pollen clusters," *Current Biology*, 4:851–853, 1994.

Somerville, C. and Somerville, S., *Science* 285:380, 1999.

Spielmann et al., *Mol. Gen. Genet.*, 205:34, 1986.

Stalker et al., *Science*, 242:419–422, 1988.

Stiefel et al., *Nature*, 341:343, 1989.

Stinchcomb et al., *Nature*, 282:39–43, 1979.

Stougaard, *The Plant Journal.*, 3:755–761, 1993.

Sullivan, Christensen, Quail, *Mol. Gen. Genet.*, 215(3): 431440, 1989.

Sun et al., *Cell*, 91:1007, 1997.

Sutcliffe, *Proc. Nat'l Acad. Sci. USA*, 75:3737–3741, 1978.

Symington et al., *Cell*, 52:237–240, 1988.

Symons, "Avacado sunblotch viroid: primary sequence and proposed secondary structure." *Nucl. Acids Res.*, 9:6527–6537, 1981.

Symons, "Small catalytic RNAs." *Annu. Rev. Biochem.*, 61:641–671, 1992.

Tarczynski et al., "Expression of a bacterial mtlD gene in transgenic tobacco leads to production and accumulation of mannitol," *Proc. Natl. Acad. Sci. USA*, 89:1–5, 1992.

Tarczynski et al., "Stress Protection of Transgenic Tobacco by Production of the Osmolyte Mannitol," *Science*, 259: 508–510, 1993.

Thillet et al., *J. Biol. Chem.*, 263:12500–12508, 1988.

Thomas et al., *Cell*, 44:419–428, 1986.

Thomas et al., *Proc. Natl. Acad. Sci. USA*, 71:4579, 1974.

Thompson et al., "Decreased expression of BRCA1 accelerates growth and is often present during sporadic breast cancer progression," *Nature Genet.*, 9:444–450, 1995.

Thompson et al., *Nuc. Acids Res.*, 24:3017, 1996.

Tian, Sequin, Charest, *Plant Cell Rep.*, 16:267–271, 1997.

Tominaga, *Microbiology*, 143:2057–63, 1997

Toriyama et al., *Theor Appl. Genet.*, 73:16, 1986.

Tsay et al., *Science*, 260:342, 1993.

Tugal et al., *Plant Physiol.*, 120:309, 1999

Twell et al., *Genes Dev* 5:496–507, 1991

Twell et al., *Plant Physiol* 91:1270–1274, 1989.

Tyler-Smith et al., "Mammalian chromosome structure," *Current Biology*, 3:390–397, 1993.

Uchimiya et al., *Mol. Gen. Genet.*, 204:204, 1986.

Vahedian et al., "Genomic organization and evolution of the soybean SB92 satellite sequence," Plant Mol. Biol. 29: 857–862, 1997.

Van der Krol, Mur, Beld, Mol, Stuitje, "Flavonoid genes in petunia: addition of a limiting number of copies may lead to a suppression of gene expression," *Plant Cell*, 2:291–99, 1990.

Van't Hof, Kuniyuki, Bjerkens, "The size and number of replicon families of chromosomal DNA of *Arabidopsis thaliana*," *Chromosoma*, 68: 269–285, 1978.

Vasil et al., "Herbicide-resistant fertile transgenic wheat plants obtained by microprojectile bombardment of regenerable embryogenic callus," *Biotechnology*, 10:667–674, 1992.

Vasil, *Biotechnology*, 6:397, 1988.

Vernon and Bohnert, *The EMBO J*, 11:2077–2085, 1992.

Voytas and Ausubel, *Nature*, 336:242, 1988.

Wagner et al., "Coupling of adenovirus to transferrin-polylysine/DNA complexes greatly enhances receptor-mediated gene delivery and expression of transfected genes," *Proc. Nat'l Acad. Sci. USA* 89(13):6099–6103, 1992.

Walker et al., *Proc. Nat'l Acad. Sci. USA*, 84:6624–6628, 1987.

Wang et al., *Molecular and Cellular Biology*, 12(8):3399–3406, 1992.

Watrud et al., In: *Engineered Organisms and the Environment*, 1985.

Watson et al., *Recombinant DNA: A Short Course*, 1983.

Weide et al., "Paracentromeric sequences on tomato chromosome 6 show homology to human satellite III and to the mammalian CENP-B binding box," Mol. Gen. Genet. 259 (2): 190–197, 1998.

Weinsink et al., *Cell*, 3:315–325, 1974.

Wevrick et al., "Partial deletion of alpha satellite DNA association with reduced amounts of the centromere protein CENP-B in a mitotically stable human chromosome rearrangement," *Mol Cell Biol.*, 10:6374–6380, 1990.

Whitehouse, *Nature*, No. 4205: 893, 1950.

Wigler et al., *Cell*, 11:223, 1977.

Willard, H., *Nature Genetics* 15:345–354, 1997

Willard, H., "Centromeres of mammalian chromosomes" *Trends Genet.*, 6:410–416, 1990.

Wolter et al., *The EMBO J.*, 4685–4692, 1992.

Wong et al., "Electric field mediated gene transfer," *Biochim. Biophys. Res. Commun.* 107(2):584–587, 1982.

Wright et al., *Genetics*, 142:569, 1996.

Xia, X. et al., "Structure and evolution of a highly repetitive DNA sequence from *Brassica napus*," Plant Mol. Biol. 21:213–224, 1993.

Xia, X. et al., "Genomic organization of the canrep repetitive DNA in *Brassica juncea*," Plant Mol. Biol. 26:817–832, 1994.

Xiang and Guerra, *Plant Physiol.*, 102:287–293, 1993.

Xu et al., *Plant Physiol.*, 110:249–257, 1996.

Yamada et al., *Plant Cell Rep.*, 4:85, 1986.

Yamaguchi-Shinozaki et al., *Plant Cell Physiol.*, 33:217–224, 1992.

Yang and Russell, *Proc. Nat'l Acad. Sci. USA*, 87:4144–4148, 1990.

Yen, *Embo J.* 10(5), 1245–1254, 1991.

Young et al., In: *Eukaryotic Genetic Systems ICN-UCLA Symposia on Molecular and Cellular Biology*, VII, 315–331, 1977.

Yuan and Altman, "Selection of guide sequences that direct efficient cleavage of mRNA by human ribonuclease P," *Science*, 263:1269–1273, 1994.

Yuan et al., "Targeted cleavage of mRNA by human RNase P," *Proc. Nat. Acad. Sci. USA*, 89:8006–8010, 1992.

Zatloukal et al., "Transferrinfection: a highly efficient way to express gene constructs in eukaryotic cells," *Ann. N.Y. Acad. Sci*, 660:136–153, 1992.

Zhang et al., *Gene*, 202:139–46, 1997

Zhang et al., *Zea mays* B chromosome centromere repeat sequence Zea_mays_MBsC216 pMBsC216 unpublished Zukowsky et al., *Proc. Nat'l Acad. Sci. USA*, 80:1101–1105, 1983.

The invention claimed is:

1. A *Glycine max* plant cell comprising a minichromosome that (i) is not integrated into the plant cell genome and (ii) comprises a centromere sequence,
wherein the centromere sequence is (a) from *Glycine max* genomic DNA (b) confers the ability to segregate to daughter cells and (c) comprises at least 5 repeated nucleotide sequences, wherein the repeated nucleotide sequence is about 75 base pairs to about 210 base pairs in length.

2. The *Glycine max* plant cell of claim 1, further comprising an integrated exogenous structural gene.

3. A *Glycine max* plant comprising the *Glycine max* plant cell of claim 1.

4. A *Glycine max* seed comprising the *Glycine max* plant cell of claim 1.

5. A method of using a plant of claim 3, the method comprising growing the plant to produce a recombinant protein encoded by a structural gene of the minichromosome.

6. The *Glycine max* plant cell of claim 1, wherein the repeated nucleotide sequence hybridizes to SEQ ID NO: 6 under selective conditions comprising 0.02 M to 0.15 M NaCl at a temperature of about 70° C.

7. The *Glycine max* plant cell of claim 1, wherein the repeated nucleotide sequence comprises SEQ ID NO: 6.

* * * * *

UNITED STATES PATENT AND TRADEMARK OFFICE
CERTIFICATE OF CORRECTION

PATENT NO.         : 7,227,057 B2                                       Page 1 of 1
APPLICATION NO.    : 11/049537
DATED              : June 5, 2007
INVENTOR(S)        : Jennifer M. Mach et al.

It is certified that error appears in the above-identified patent and that said Letters Patent is hereby corrected as shown below:

On the Title Page:

Item (73), 3$^{rd}$ named Inventor, "James Jin" should be -- RongGuan Jin --.

Signed and Sealed this

Twenty-seventh Day of May, 2008

JON W. DUDAS
*Director of the United States Patent and Trademark Office*